(12) United States Patent  
Semingson et al.

(10) Patent No.: US 12,369,952 B2
(45) Date of Patent: Jul. 29, 2025

(54) BONE TIE AND PORTAL

(71) Applicant: Spinal Elements, Inc., Carlsbad, CA (US)

(72) Inventors: Taylor Semingson, San Diego, CA (US); Megan Monier, Vista, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 18/062,979

(22) Filed: Dec. 7, 2022

(65) Prior Publication Data
US 2023/0181226 A1 Jun. 15, 2023

Related U.S. Application Data

(60) Provisional application No. 63/288,234, filed on Dec. 10, 2021.

(51) Int. Cl.
*A61B 17/56* (2006.01)
*A61B 17/00* (2006.01)
*A61B 17/70* (2006.01)

(52) U.S. Cl.
CPC ...... *A61B 17/7053* (2013.01); *A61B 17/7083* (2013.01); *A61B 2017/00477* (2013.01); *A61B 2017/564* (2013.01)

(58) Field of Classification Search
CPC ............ A61B 17/7053; A61B 17/7062; A61B 17/7064; A61B 17/82; A61B 17/8861; A61B 17/8869
See application file for complete search history.

(56) References Cited

U.S. PATENT DOCUMENTS

| | | |
|---|---|---|
| 86,016 A | 1/1869 | Howell |
| 1,630,239 A | 5/1927 | Binkley et al. |
| 1,822,280 A | 9/1931 | Ervay |
| 1,822,330 A | 9/1931 | Anslie |
| 2,486,303 A | 10/1949 | Longfellow |
| 2,706,023 A | 4/1955 | Merritt |
| 2,967,282 A | 1/1961 | Schwartz et al. |

(Continued)

FOREIGN PATENT DOCUMENTS

| | | |
|---|---|---|
| CA | 2 437 575 | 4/2009 |
| DE | 93 04 368 | 5/1993 |

(Continued)

OTHER PUBLICATIONS

3rd Party Lab Notebook, "Facet Cartilage Repair," dated May 20, 2003 in 2 pages.

(Continued)

*Primary Examiner* — Eduardo C Robert
*Assistant Examiner* — Holly Joanna Lane
(74) *Attorney, Agent, or Firm* — Knobbe, Martens, Olson & Bear, LLP

(57) ABSTRACT

Various systems and methods for treating the spine are provided. A portal system can be provided for treating the spine. The portal system can include a portal comprising a proximal end and a distal end, a first passageway extending between the proximal end and the distal end, a second passageway extending between the proximal end and the distal end, and a latch. The bone tie can include a head, a body section comprising one or more gears, and a fastener section comprising a ratchet.

19 Claims, 59 Drawing Sheets

(56) References Cited

U.S. PATENT DOCUMENTS

| | | | |
|---|---|---|---|
| 3,111,945 A | 11/1963 | Von Solbrig |
| 3,149,808 A | 9/1964 | Weckesser |
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,164,793 A | 8/1979 | Swanson |
| 4,166,292 A | 9/1979 | Bokros |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,557,259 A | 12/1985 | Wu |
| 4,570,303 A | 2/1986 | Richmond |
| 4,570,618 A | 2/1986 | Wu |
| 4,573,458 A | 3/1986 | Lower |
| 4,573,459 A | 3/1986 | Litton |
| 4,634,445 A | 1/1987 | Helal |
| 4,643,178 A | 2/1987 | Nastari et al. |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,852,558 A | 8/1989 | Outerbridge |
| 4,863,477 A | 9/1989 | Monson |
| 4,880,429 A | 11/1989 | Stone |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,955,913 A | 9/1990 | Robinson |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,092,868 A | 3/1992 | Mehdian |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,192,327 A | 3/1993 | Brantigan |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,304,178 A | 4/1994 | Stahurski |
| 5,306,275 A | 4/1994 | Bryan |
| 5,306,308 A | 4/1994 | Gross et al. |
| 5,306,309 A | 4/1994 | Wagner et al. |
| 5,326,364 A | 7/1994 | Clift, Jr. et al. |
| 5,330,479 A | 7/1994 | Whitmore |
| 5,360,431 A | 11/1994 | Puno et al. |
| 5,368,596 A | 11/1994 | Burkhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,142 A | 3/1996 | Fodor et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,698 A | 7/1996 | Preissman |
| 5,540,703 A | 7/1996 | Barker, Jr. et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,609,634 A | 3/1997 | Voydeville |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |
| 5,797,916 A | 8/1998 | McDowell |
| 5,810,854 A * | 9/1998 | Beach ............... A61B 17/064 |
| | | 24/17 AP |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |

(56) References Cited

U.S. PATENT DOCUMENTS

| | | |
|---|---|---|
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,918,604 A | 7/1999 | Whelan |
| 5,941,881 A | 8/1999 | Barnes |
| 5,951,555 A | 9/1999 | Rehak et al. |
| 5,964,765 A | 10/1999 | Fenton et al. |
| 5,993,452 A | 11/1999 | Vandewalle |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,768 A | 2/2000 | Wenstrom, Jr. et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gill et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| 6,409,765 B1 | 6/2002 | Bianchi et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,423,071 B1 | 7/2002 | Lawson |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,447,544 B1 | 9/2002 | Michelson |
| 6,470,207 B1 | 10/2002 | Simon et al. |
| 6,475,220 B1 | 11/2002 | Whiteside |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,178 B1 | 12/2003 | Veldhuizen et al. |
| 6,656,195 B2 | 12/2003 | Peters et al. |
| 6,669,697 B1 | 12/2003 | Pisharodi |
| 6,669,729 B2 | 12/2003 | Chin |
| 6,679,914 B1 | 1/2004 | Gabbay |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| 7,004,971 B2 | 2/2006 | Serhan et al. |
| D517,404 S | 3/2006 | Schluter |
| 7,008,429 B2 | 3/2006 | Golobek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Schluter |
| 7,371,238 B2 | 5/2008 | Sololeski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,695,472 B2 | 4/2010 | Young |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 | 3/2012 | Pieske |
| 8,163,016 B2 | 4/2012 | Linares |
| 8,172,877 B2 | 5/2012 | Winslow et al. |
| 8,177,810 B2 | 5/2012 | Ferree |
| 8,192,468 B2 | 6/2012 | Biedermann et al. |
| 8,216,275 B2 | 7/2012 | Fielding et al. |
| 8,231,661 B2 | 7/2012 | Carls |
| 8,246,655 B2 | 8/2012 | Jackson et al. |
| 8,267,966 B2 | 9/2012 | McCormack et al. |
| 8,292,954 B2 | 10/2012 | Robinson et al. |
| 8,306,307 B2 | 11/2012 | Koike et al. |
| 8,382,801 B2 | 2/2013 | Lamborne et al. |
| 8,394,125 B2 | 3/2013 | Assell |
| 8,460,346 B2 | 6/2013 | Ralph et al. |
| 8,486,078 B2 | 7/2013 | Carl et al. |
| 8,496,691 B2 | 7/2013 | Blain |
| 8,579,903 B2 | 11/2013 | Carl |
| 8,652,137 B2 * | 2/2014 | Blain ............ A61B 17/1608 606/167 |
| 8,740,942 B2 | 6/2014 | Blain |
| 8,740,949 B2 | 6/2014 | Blain |
| 8,753,345 B2 | 6/2014 | McCormack et al. |
| 8,784,423 B2 | 7/2014 | Kowarsch et al. |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,028,522 B1 | 5/2015 | Prado |
| 9,060,787 B2 | 6/2015 | Blain et al. |
| 9,101,410 B1 | 8/2015 | Urrea |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |

(56) References Cited

U.S. PATENT DOCUMENTS

| | | |
|---|---|---|
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,439,686 B2 | 9/2016 | Rooney et al. |
| 9,456,855 B2 | 10/2016 | Blain et al. |
| 9,517,077 B2 * | 12/2016 | Blain ............. A61B 17/7064 |
| D777,921 S | 1/2017 | Blain et al. |
| D780,315 S | 2/2017 | Blain et al. |
| 9,572,602 B2 | 2/2017 | Blain et al. |
| D784,536 S | 4/2017 | Freudenthal |
| 9,615,861 B2 | 4/2017 | Perez-Cruet et al. |
| D790,062 S | 6/2017 | Blain et al. |
| 9,675,387 B2 | 6/2017 | Blain |
| 9,743,937 B2 | 8/2017 | Blain et al. |
| D799,037 S | 10/2017 | Kubiak et al. |
| 9,808,294 B2 | 11/2017 | Blain |
| 9,820,784 B2 | 11/2017 | Blain et al. |
| 9,839,450 B2 | 12/2017 | Blain et al. |
| D810,942 S | 2/2018 | Blain et al. |
| D812,754 S | 3/2018 | Blain et al. |
| 9,931,142 B2 | 4/2018 | Blain |
| 9,936,984 B2 | 4/2018 | Blain |
| 10,022,161 B2 | 7/2018 | Blain |
| 10,039,578 B2 * | 8/2018 | Anderson ......... A61B 17/7085 |
| 10,085,776 B2 | 10/2018 | Blain |
| D834,194 S | 11/2018 | Blain et al. |
| 10,194,955 B2 | 2/2019 | Blain et al. |
| 10,251,679 B2 | 4/2019 | Blain et al. |
| D848,623 S | 5/2019 | Franche |
| D857,900 S | 8/2019 | Blain et al. |
| 10,368,921 B2 | 8/2019 | Blain |
| 10,426,524 B2 | 10/2019 | Blain |
| 10,456,267 B2 * | 10/2019 | Michielli ........... A61B 17/0401 |
| 10,610,364 B2 | 4/2020 | Dee |
| 10,624,680 B2 | 4/2020 | Blain |
| D884,896 S | 5/2020 | Blain et al. |
| 10,758,361 B2 | 9/2020 | Blain |
| D926,982 S | 8/2021 | Blain et al. |
| 11,272,961 B2 | 3/2022 | Blain et al. |
| 11,304,733 B2 | 4/2022 | Blain et al. |
| D958,366 S | 7/2022 | Blain et al. |
| 11,457,959 B2 | 10/2022 | Semingson |
| 11,464,551 B2 | 10/2022 | Blain |
| 11,464,552 B2 | 10/2022 | Semingson et al. |
| 11,478,275 B2 | 10/2022 | Smith et al. |
| 11,517,354 B2 | 12/2022 | Blain et al. |
| D979,062 S | 2/2023 | Blain et al. |
| 11,918,258 B2 | 3/2024 | Blain et al. |
| 11,998,240 B2 | 6/2024 | Smith et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0099444 A1 | 7/2002 | Boyd et al. |
| 2002/0120335 A1 | 8/2002 | Angelucci et al. |
| 2002/0123806 A1 | 9/2002 | Reiley |
| 2002/0138077 A1 | 9/2002 | Ferree |
| 2002/0151895 A1 | 10/2002 | Soboleski et al. |
| 2002/0173800 A1 | 11/2002 | Dreyfuss et al. |
| 2002/0173813 A1 * | 11/2002 | Peterson ............. A61B 17/1604 606/167 |
| 2002/0198527 A1 | 12/2002 | Muckter |
| 2003/0004572 A1 | 1/2003 | Goble |
| 2003/0028250 A1 | 2/2003 | Reiley et al. |
| 2003/0028251 A1 * | 2/2003 | Mathews ............. A61M 25/10 623/23.62 |
| 2003/0040797 A1 | 2/2003 | Fallin et al. |
| 2003/0093152 A1 | 5/2003 | Pedersen et al. |
| 2003/0093154 A1 | 5/2003 | Estes et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0181979 A1 | 9/2003 | Ferree |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059333 A1 | 3/2004 | Carl et al. |
| 2004/0059429 A1 | 3/2004 | Amin et al. |
| 2004/0087954 A1 | 5/2004 | Allen et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0172019 A1 | 9/2004 | Ferree |
| 2004/0176844 A1 | 9/2004 | Zubok et al. |
| 2004/0195727 A1 | 10/2004 | Stoy |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0090833 A1 * | 4/2005 | DiPoto ............. A61B 17/3439 606/99 |
| 2005/0107879 A1 | 5/2005 | Christensen et al. |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0154463 A1 | 7/2005 | Trieu |
| 2005/0159746 A1 | 7/2005 | Grab et al. |
| 2005/0171547 A1 | 8/2005 | Aram |
| 2005/0197700 A1 | 9/2005 | Boehem et al. |
| 2005/0204515 A1 | 9/2005 | Hewes |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1 | 1/2006 | Alamin et al. |
| 2006/0036323 A1 | 2/2006 | Carl et al. |
| 2006/0041311 A1 | 2/2006 | McLeer |
| 2006/0079908 A1 * | 4/2006 | Lieberman ......... A61B 17/1757 606/99 |
| 2006/0084985 A1 | 4/2006 | Kim |
| 2006/0085006 A1 | 4/2006 | Ek et al. |
| 2006/0085072 A1 | 4/2006 | Funk et al. |
| 2006/0106381 A1 | 5/2006 | Ferree et al. |
| 2006/0111782 A1 | 5/2006 | Petersen |
| 2006/0116684 A1 | 6/2006 | Whelan |
| 2006/0122620 A1 * | 6/2006 | Kim ................... A61B 17/3468 606/90 |
| 2006/0149289 A1 | 7/2006 | Winslow et al. |
| 2006/0149375 A1 | 7/2006 | Yuan et al. |

(56) References Cited

U.S. PATENT DOCUMENTS

| | | |
|---|---|---|
| 2006/0190081 A1 | 8/2006 | Kraus et al. |
| 2006/0200137 A1 | 9/2006 | Soboleski et al. |
| 2006/0241597 A1 | 10/2006 | Mitchell et al. |
| 2006/0241601 A1 | 10/2006 | Trautwein et al. |
| 2006/0241758 A1 | 10/2006 | Peterman et al. |
| 2006/0241778 A1 | 10/2006 | Ogilvie |
| 2006/0247650 A1 | 11/2006 | Yerby et al. |
| 2006/0293691 A1 | 12/2006 | Mitra et al. |
| 2007/0055236 A1 | 3/2007 | Hudgins et al. |
| 2007/0055252 A1 | 3/2007 | Blain et al. |
| 2007/0055373 A1 | 3/2007 | Hudgins et al. |
| 2007/0073293 A1* | 3/2007 | Martz .................. A61L 27/365 606/86 A |
| 2007/0078464 A1 | 4/2007 | Jones et al. |
| 2007/0100452 A1 | 5/2007 | Prosser |
| 2007/0118218 A1 | 5/2007 | Hooper |
| 2007/0123863 A1 | 5/2007 | Winslow et al. |
| 2007/0135814 A1 | 6/2007 | Farris |
| 2007/0149976 A1 | 6/2007 | Hale et al. |
| 2007/0179619 A1 | 8/2007 | Grab |
| 2007/0250166 A1 | 10/2007 | McKay |
| 2007/0255414 A1 | 11/2007 | Melkent et al. |
| 2007/0270812 A1 | 11/2007 | Peckham |
| 2008/0009866 A1 | 1/2008 | Alamin et al. |
| 2008/0033552 A1 | 2/2008 | Lee et al. |
| 2008/0046083 A1 | 2/2008 | Hewko |
| 2008/0058929 A1 | 3/2008 | Whelan |
| 2008/0082103 A1 | 4/2008 | Hutton et al. |
| 2008/0082172 A1 | 4/2008 | Jackson |
| 2008/0114357 A1 | 5/2008 | Allard et al. |
| 2008/0161853 A1 | 7/2008 | Arnold et al. |
| 2008/0177264 A1 | 7/2008 | Alamin et al. |
| 2008/0177326 A1 | 7/2008 | Thompson |
| 2008/0183209 A1 | 7/2008 | Robinson et al. |
| 2008/0183211 A1 | 7/2008 | Lamborne et al. |
| 2008/0228225 A1 | 9/2008 | Trautwein et al. |
| 2008/0255664 A1 | 10/2008 | Hogendijk et al. |
| 2008/0262549 A1 | 10/2008 | Bennett et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024165 A1 | 1/2009 | Ferree |
| 2009/0024166 A1 | 1/2009 | Carl et al. |
| 2009/0036926 A1 | 2/2009 | Hestad |
| 2009/0072006 A1 | 3/2009 | Clauson et al. |
| 2009/0076617 A1 | 3/2009 | Ralph et al. |
| 2009/0105766 A1 | 4/2009 | Thompson et al. |
| 2009/0125030 A1* | 5/2009 | Tebbe ................. A61B 17/3468 606/191 |
| 2009/0125066 A1 | 5/2009 | Kraus et al. |
| 2009/0138048 A1 | 5/2009 | Baccelli et al. |
| 2009/0171357 A1* | 7/2009 | Justin .................... A61B 17/82 606/74 |
| 2009/0171360 A1 | 7/2009 | Whelan |
| 2009/0198282 A1 | 8/2009 | Fielding et al. |
| 2009/0198339 A1 | 8/2009 | Kleiner et al. |
| 2009/0248077 A1 | 10/2009 | Johns |
| 2009/0248082 A1 | 10/2009 | Crook et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0292317 A1 | 11/2009 | Belliard |
| 2009/0306716 A1 | 12/2009 | Beger et al. |
| 2009/0326589 A1 | 12/2009 | Lemoine et al. |
| 2010/0004657 A1 | 1/2010 | Dudasik |
| 2010/0010548 A1 | 1/2010 | Hermida Ochoa |
| 2010/0036442 A1 | 2/2010 | Lauryssen |
| 2010/0063550 A1 | 3/2010 | Felix et al. |
| 2010/0076503 A1 | 3/2010 | Beyar et al. |
| 2010/0087859 A1 | 4/2010 | Jackson, Jr. |
| 2010/0106194 A1 | 4/2010 | Bonutti et al. |
| 2010/0121387 A1 | 5/2010 | Belliard |
| 2010/0131008 A1 | 5/2010 | Overes et al. |
| 2010/0168864 A1 | 7/2010 | White et al. |
| 2010/0179553 A1 | 7/2010 | Ralph et al. |
| 2010/0185241 A1 | 7/2010 | Malandain et al. |
| 2010/0191286 A1 | 7/2010 | Butler |
| 2010/0204700 A1 | 8/2010 | Falahee |
| 2010/0204732 A1 | 8/2010 | Aschmann et al. |
| 2010/0234894 A1 | 9/2010 | Alamin et al. |
| 2010/0256680 A1 | 10/2010 | Pasquet et al. |
| 2010/0274289 A1 | 10/2010 | Carls et al. |
| 2010/0292698 A1 | 11/2010 | Hulliger et al. |
| 2010/0298829 A1 | 11/2010 | Schaller et al. |
| 2010/0318133 A1 | 12/2010 | Tornier |
| 2011/0015744 A1 | 1/2011 | Squires et al. |
| 2011/0022050 A1 | 1/2011 | McClellan et al. |
| 2011/0034956 A1 | 2/2011 | Mazda et al. |
| 2011/0040332 A1 | 2/2011 | Culbert |
| 2011/0060366 A1 | 3/2011 | Heim et al. |
| 2011/0082504 A1 | 4/2011 | Singhatat et al. |
| 2011/0098816 A1 | 4/2011 | Jacob et al. |
| 2011/0106163 A1 | 5/2011 | Hochschuler et al. |
| 2011/0106259 A1 | 5/2011 | Lindenmann et al. |
| 2011/0160772 A1 | 6/2011 | Arcenio et al. |
| 2011/0172712 A1 | 7/2011 | Chee et al. |
| 2011/0245875 A1 | 10/2011 | Karim |
| 2011/0295318 A1 | 12/2011 | Alamin et al. |
| 2011/0301644 A1 | 12/2011 | Belliard |
| 2011/0320000 A1 | 12/2011 | O'Neil et al. |
| 2012/0022591 A1 | 1/2012 | Baccelli et al. |
| 2012/0022649 A1 | 1/2012 | Robinson et al. |
| 2012/0035658 A1 | 2/2012 | Goble et al. |
| 2012/0041441 A1 | 2/2012 | Bernstein et al. |
| 2012/0046749 A1 | 2/2012 | Tatsumi |
| 2012/0101502 A1 | 4/2012 | Kartalian et al. |
| 2012/0150231 A1 | 6/2012 | Alamin et al. |
| 2012/0221060 A1 | 8/2012 | Blain |
| 2012/0245586 A1 | 9/2012 | Lehenkari et al. |
| 2012/0245637 A1 | 9/2012 | Kraus et al. |
| 2012/0271354 A1 | 10/2012 | Baccelli et al. |
| 2012/0277801 A1 | 11/2012 | Marik et al. |
| 2013/0023878 A1 | 1/2013 | Belliard et al. |
| 2013/0041410 A1 | 2/2013 | Hestad et al. |
| 2013/0072983 A1 | 3/2013 | Lindquist et al. |
| 2013/0079778 A1 | 3/2013 | Azuero et al. |
| 2013/0123923 A1 | 5/2013 | Pavlov et al. |
| 2013/0197643 A1 | 8/2013 | Greenberg et al. |
| 2013/0204250 A1 | 8/2013 | McDevitt et al. |
| 2013/0253649 A1 | 9/2013 | Davis |
| 2013/0261625 A1 | 10/2013 | Koch et al. |
| 2013/0325065 A1 | 12/2013 | Malandain et al. |
| 2014/0012318 A1 | 1/2014 | Goel |
| 2014/0018816 A1 | 1/2014 | Fenn et al. |
| 2014/0066758 A1 | 3/2014 | Marik et al. |
| 2014/0214084 A1 | 7/2014 | Jackson et al. |
| 2014/0257397 A1 | 9/2014 | Akbarnia et al. |
| 2014/0277149 A1 | 9/2014 | Rooney et al. |
| 2014/0309699 A1 | 10/2014 | Houff |
| 2014/0336653 A1 | 11/2014 | Bromer |
| 2014/0378976 A1 | 12/2014 | Garcia |
| 2015/0045794 A1 | 2/2015 | Garcia et al. |
| 2015/0119988 A1 | 4/2015 | Assell et al. |
| 2015/0164652 A1 | 6/2015 | Assell et al. |
| 2015/0190149 A1 | 7/2015 | Assell et al. |
| 2015/0209096 A1 | 7/2015 | Gephart |
| 2015/0305792 A1 | 10/2015 | Knueppel |
| 2015/0313656 A1 | 11/2015 | Hulliger |
| 2015/0327872 A1 | 11/2015 | Assell et al. |
| 2015/0342648 A1 | 12/2015 | McCormack et al. |
| 2015/0342657 A1 | 12/2015 | Voisard et al. |
| 2016/0113692 A1 | 4/2016 | Knoepfle |
| 2016/0128838 A1 | 5/2016 | Assell et al. |
| 2017/0239060 A1 | 8/2017 | Blain |
| 2017/0296234 A1 | 10/2017 | Jackson et al. |
| 2017/0333091 A1 | 11/2017 | Taber et al. |
| 2017/0333205 A1 | 11/2017 | Joly et al. |
| 2018/0064461 A1 | 3/2018 | Tran et al. |
| 2018/0132915 A1 | 5/2018 | Esser et al. |
| 2019/0167314 A1 | 6/2019 | Mosnier et al. |
| 2019/0365433 A1 | 12/2019 | Blain et al. |
| 2020/0214746 A1 | 7/2020 | Blain et al. |

(56) References Cited

U.S. PATENT DOCUMENTS

| | | |
|---|---|---|
| 2021/0000608 A1 | 1/2021 | Blain et al. |
| 2021/0251667 A1 | 8/2021 | Blain et al. |
| 2022/0151659 A1 | 5/2022 | Smith et al. |
| 2022/0175424 A1 | 6/2022 | Blain et al. |
| 2022/0218394 A1 | 7/2022 | Blain et al. |
| 2022/0273442 A1 | 9/2022 | Blain et al. |
| 2022/0354547 A1 | 11/2022 | Semingson et al. |
| 2022/0401133 A1 | 12/2022 | Blain |
| 2023/0019908 A1 | 1/2023 | Semingson et al. |
| 2023/0089601 A1 | 3/2023 | Blain |
| 2023/0114473 A1 | 4/2023 | Semingson |
| 2024/0008903 A1 | 1/2024 | Semingson et al. |
| 2024/0180597 A1 | 6/2024 | Blain |
| 2024/0341810 A1 | 10/2024 | Smith et al. |

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 1 201 202 | 5/2002 |
| EP | 1 201 256 | 5/2002 |
| EP | 2 138 122 | 12/2009 |
| EP | 2 919 717 | 9/2015 |
| FR | 2 704 745 | 11/1994 |
| FR | 2 722 980 | 2/1996 |
| GB | 2 366 736 | 3/2002 |
| JP | 53-005889 | 1/1978 |
| JP | 62-270147 | 11/1987 |
| JP | 03-100154 | 4/1991 |
| JP | 03-240660 | 10/1991 |
| JP | 06-319742 | 11/1994 |
| JP | 08-509918 | 10/1996 |
| JP | 10-179622 | 7/1998 |
| JP | 2000-201941 | 7/2000 |
| JP | 2000-210297 | 8/2000 |
| JP | 2003-079649 | 3/2003 |
| JP | 2003-516173 | 5/2003 |
| JP | 2004-508888 | 3/2004 |
| JP | 2004-181236 | 7/2004 |
| JP | 2004-537354 | 12/2004 |
| JP | 2006-230722 | 9/2006 |
| JP | 2006-528540 | 12/2006 |
| JP | 2007-503884 | 3/2007 |
| JP | 2007-513739 | 5/2007 |
| JP | 2007-517627 | 7/2007 |
| JP | 2007-190389 | 8/2007 |
| JP | 2008-508067 | 3/2008 |
| JP | 2008-086827 | 4/2008 |
| JP | 2008-510526 | 4/2008 |
| JP | 2008-522787 | 7/2008 |
| JP | 2008-537498 | 9/2008 |
| JP | 2009-533167 | 9/2009 |
| JP | 2010-510852 | 4/2010 |
| JP | 2010-173739 | 8/2010 |
| JP | 2011-519303 | 7/2011 |
| JP | 2011-522627 | 8/2011 |
| JP | 2012-509740 | 4/2012 |
| JP | 2012-521221 | 9/2012 |
| JP | 2012-523903 | 10/2012 |
| JP | 2012-509719 | 1/2013 |
| JP | 2013-534451 | 9/2013 |
| JP | 2013-535247 | 9/2013 |
| JP | 2014-504905 | 2/2014 |
| JP | 2014-513583 | 6/2014 |
| JP | 2014-523751 | 9/2014 |
| JP | 2015-500701 | 1/2015 |
| JP | 2016-511059 | 4/2016 |
| MX | 6012309 | 1/2007 |
| WO | WO 88/006022 | 8/1988 |
| WO | WO 93/014721 | 8/1993 |
| WO | WO 94/004088 | 3/1994 |
| WO | WO 97/047246 | 12/1997 |
| WO | WO 98/048717 | 11/1998 |
| WO | WO 99/023963 | 5/1999 |
| WO | WO 00/038582 | 7/2000 |
| WO | WO 00/053126 | 9/2000 |
| WO | WO 01/030248 | 5/2001 |
| WO | WO 02/045765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2006/023980 | 3/2006 |
| WO | WO 2006/096803 | 9/2006 |
| WO | WO 2008/008522 | 1/2008 |
| WO | WO 2008/146185 | 12/2008 |
| WO | WO 2009/013397 | 1/2009 |
| WO | WO 2009/015100 | 1/2009 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/116266 | 8/2012 |
| WO | WO 2012/116267 | 8/2012 |
| WO | WO 2012/154265 | 11/2012 |
| WO | WO 2013/022880 | 2/2013 |
| WO | WO 2013/138655 | 9/2013 |
| WO | WO 2014/078541 | 5/2014 |
| WO | WO 2020/030656 | 2/2020 |
| WO | WO 2023/108007 | 6/2023 |

OTHER PUBLICATIONS

ArthroTek, "CurvTek® Bone Tunneling System," Surgical Technique, 2000, pp. 6.

ArthroTek, "CurvTek® Bone Tunneling System," User's Manual, 2000, pp. 20.

Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.

Beaman, MD et al., "Substance P Innervation of Lumbar Spine Facet Joints", SPINE, 1993, vol. 18, No. 8, pp. 1044-1049.

Butterman, et al., "An Experimental Method for Measuring Force on the Spinal Facet Joint: Description and Application of the Method", Journal of Biomechanical Engineering, Nov. 1991, vol. 113, pp. 375-386.

Cruess et al., "The Response of Articular Cartilage to Weight-Bearing Against Metal", The Journal of Bone and Joint Surgery, Aug. 1984, vol. 66-B, No. 4, pp. 592-597.

Dalldorf et al., "Rate of Degeneration of Human Acetabular Cartilage after Hemiarthroplasty", The Journal of Bone and Joint Surgery, Jun. 1995, vol. 77. No. 6, pp. 877-882.

E-mail from 3rd Party citing U.S. Appl. No. 60/749,000; U.S. Appl. No. 60/749,000 and U.S. Appl. No. 60/749,000, initial e-mail dated May 11, 2009, reply e-mail dated May 18, 2009.

Frost, Harold M., "From Wolff's Law to the Utah Paradigm: Insights About Bone Physiology and Its Clinical Applications", The Anatomical Record, 2001, vol. 262, pp. 398-419.

King et al., "Mechanism of Spinal Injury Due to Caudocephalad Acceleration," Symposium on the Lumbar Spine, Orthopedic Clinic of North America, Jan. 1975, vol. 6, pp. 19-31.

Kurtz, PhD et al., "Isoelastic Polyaryletheretherketone Implants for Total Joint Replacement", PEEK Biomaterials Handbook, Ch. 14, 2012, pp. 221-226.

Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.

Panjabi, PhD et al., "Articular Facets of the Human Spine: Quantitative Three-Dimensional Anatomy", SPINE, 1993, vol. 18, No. 10, pp. 1298-1310.

(56) References Cited

OTHER PUBLICATIONS

PARTEQ Innovations, "Facet Joint Implants & Resurfacing Devices," Technology Opportunity Bulletin, Tech ID 1999-012, Queen's University, Ontario Canada, pp. 2.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (Injury), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Sharpe Products, "Metal Round Disks", https://web.archive.org/web/20170705214756/https://sharpeproducts.com/store/metal-round-disks, as archived Jul. 5, 2017 in 3 pages.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. 2013237744, dated Sep. 2, 2014.
Notice of Acceptance in Australian Application No. 2013237744, dated Apr. 23, 2015.
Official Communication in Australian Application No. 2015205875, dated Apr. 2, 2016.
Official Communication in Australian Application No. 2015205875, dated Jun. 15, 2016.
Official Communication in Australian Application No. 2016231622, dated Dec. 5, 2017.
Official Communication in Australian Application No. 2016231622, dated Nov. 22, 2018.
Notice of Acceptance in Australian Application No. 2016231622, dated Dec. 4, 2018.
Official Communication in Australian Application No. 2019201539, dated Jun. 25, 2019.
Official Communication in Australian Application No. 2019201539, dated Apr. 3, 2020.
Official Communication in Australian Application No. 2020244544, dated Nov. 15, 2021.
Official Communication in Australian Application No. 2020244544, dated Apr. 27, 2022.
Official Communication in Australian Application No. 2020244544, dated Jun. 8, 2022.
Official Communication in Canadian Application No. 2,555,355, dated Sep. 2, 2011.
Official Communication in Canadian Application No. 2,803,783, dated Sep. 29, 2014.
Official Communication in Canadian Application No. 2,803,783, dated Aug. 5, 2015.
Official Communication in Canadian Application No. 2,803,783, dated Jul. 7, 2016.
Official Communication in Canadian Application No. 2,803,783, dated Apr. 5, 2017.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in European Application No. 14175088.5, dated Nov. 18, 2015.
Official Communication in European Application No. 16180368.9, dated Mar. 31, 2017.
Official Communication in European Application No. 16180368.9, dated Jan. 11, 2018.
Official Communication in European Application No. 19158915.9, dated Jul. 1, 2019.
Official Communication in European Application No. 19158915.9, dated Nov. 16, 2022.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
Official Communication in Japanese Application No. 2012-272106, dated Feb. 23, 2015.
Official Communication in Japanese Application No. 2012-272106), dated Nov. 2, 2015.
International Search Report and Written Opinion in International Application No. PCT/US2005/003753, dated Dec. 5, 2006.
International Preliminary Report on Patentability and Written Opinion in International Application No. PCT/US2005/003753, dated Jan. 9, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability and Written Opinion in International Application No. PCT/US2008/054607, dated Sep. 3, 2009.
Official Communication in Australian Application No. 2011292297, dated Jul. 10, 2013.
Official Communication in Australian Application No. 2014277721, dated Sep. 8, 2016.
Official Communication in Australian Application No. 2014277721, dated Jan. 9, 2017.
Official Communication in Canadian Application No. 2,804,223, dated Jun. 5, 2017.
Official Communication in Canadian Application No. 2,804,223, dated Mar. 14, 2018.
Official Communication in European Application No. 11818586.7, dated Nov. 6, 2014.
Official Communication in European Application No. 11818586.7, dated Feb. 3, 2017.
Official Communication in European Application No. 11818586.7, dated Apr. 8, 2021.
Official Communication in Japanese Application No. 2013-524882, dated Mar. 2, 2015.
Official Communication in Japanese Application No. 2013-524882, dated Nov. 16, 2015.
Official Communication in Japanese Application No. 2015-242990, dated Dec. 12, 2016.
Official Communication in Japanese Application No. 2015-242990, dated May 8, 2017.
Official Communication in Japanese Application No. 2015-242990, dated Aug. 21, 2017.

(56) References Cited

OTHER PUBLICATIONS

International Search Report and Written Opinion in International Application No. PCT/US2011/047432, dated Dec. 12, 2011.
International Preliminary Report on Patentability and Written Opinion in International Application No. PCT/US2011/047432, dated Feb. 28, 2013.
Official Communication in Australian Application No. 2012222229, dated Aug. 21, 2015.
Official Communication in Australian Application No. 2012222229, dated May 11, 2016.
Official Communication in Australian Application No. 2012222230, dated Aug. 21, 2015.
Official Communication in European Application No. EP12749447.4, dated Jan. 4, 2017.
Official Communication in European Application No. EP12749447.4, dated Apr. 4, 2017.
Official Communication in European Application No. EP12749447.4, dated Nov. 14, 2018.
Official Communication in European Application No. EP12749447.4, dated Aug. 18, 2021.
Official Communication in European Application No. 12749251.0, dated Jan. 4, 2017.
Official Communication in European Application No. 12749251.0, dated May 9, 2017.
Official Communication in European Application No. 12749251.0, dated Aug. 16, 2019.
Official Communication in European Application No. 12749251.0, dated Oct. 24, 2022.
Official Communication in Japanese Application No. 2013-555591, dated Jan. 4, 2016.
Official Communication in Japanese Application No. 2013-555591, dated Nov. 21, 2016.
Official Communication in Japanese Application No. 2016-246368, dated Oct. 30, 2017.
Official Communication in Japanese Application No. 2016-246368, dated Jul. 2, 2018.
Official Communication in Japanese Application No. 2013-555592, dated Dec. 7, 2015.
Official Communication in Japanese Application No. 2013-555592, dated Aug. 8, 2016.
Official Communication in Japanese Application No. 2013-555592, dated Jan. 5, 2018.
Official Communication in Japanese Application No. 2016-237460, dated Oct. 23, 2017.
Official Communication in Japanese Application No. 2016-237460, dated Apr. 16, 2018.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
Official Communication in Australian Application No. 2014241989, dated Aug. 31, 2017.
Official Communication in Australian Application No. 2014241989, dated Jun. 20, 2018.
Official Communication in Australian Application No. 2014241989, dated Aug. 17, 2018.
Official Communication in Australian Application No. 2018279003, dated Jan. 9, 2020.
Official Communication in Australian Application No. 2018279003, dated Sep. 18, 2020.
Official Communication in Australian Application No. 2018279003, dated Jan. 12, 2021.
Official Communication in Australian Application No. 2021202409, dated Jul. 9, 2022.
Official Communication in Canadian Application No. 2,903,999, dated Dec. 9, 2019.
Official Communication in Canadian Application No. 2,903,999, dated Aug. 31, 2020.
Official Communication in European Application No. 14774714.1, dated Oct. 21, 2016.
Official Communication in European Application No. 14774714.1, dated May 23, 2019.
Official Communication in European Application No. 22180771.2, dated Jan. 2, 2023.
Official Communication in Japanese Application No. 2016-500490, dated Nov. 27, 2017.
Official Communication in Japanese Application No. 2016-500490, dated May 7, 2018.
International Search Report and Written Opinion in International Application No. PCT/US2014/019302, dated May 18, 2015.
Official Communication in Australian Application No. 2014241994, dated Oct. 30, 2017.
Official Communication in Australian Application No. 2014241994, dated Jan. 31, 2020.
Official Communication in Australian Application No. 2021203165, dated Jun. 8, 2022.
Official Communication in Canadian Application No. 2,904,280, dated Dec. 9, 2019.
Official Communication in Canadian Application No. 2,904,280, dated Sep. 1, 2020.
Official Communication in Canadian Application No. 2,904,280, dated Jun. 7, 2021.
Official Communication in Canadian Application No. 2,904,280, dated Apr. 1, 2022.
Official Communication in European Application No. 14776445.0, dated Nov. 7, 2016.
Official Communication in European Application No. 14776445.0, dated Jun. 10, 2021.
Official Communication in European Application No. 14776445.0, dated May 20, 2022.
Official Communication in Japanese Application No. 2016-500498, dated Jan. 5, 2018.
Official Communication in Japanese Application No. 2016-500498, dated Jul. 2, 2018.
Official Communication in Japanese Application No. 2016-500498, dated Mar. 4, 2019.
Official Communication in Japanese Application No. 2016-500498, dated Aug. 9, 2019.
Official Communication in Japanese Application No. 2019-163133, dated Oct. 5, 2020.
Official Communication in Japanese Application No. 2019-163133, dated Jun. 7, 2021.
International Search Report and Written Opinion in International Application No. PCT/US2014/019325, dated Jun. 17, 2014.
International Preliminary Report on Patentability and Written Opinion in International Application No. PCT/US2014/019325, dated Sep. 24, 2015.
Official Communication in Australian Application No. 2014327083, dated May 31, 2018.
Notice of Acceptance in Australian Application No. 2014327083, dated Apr. 3, 2019.
Official Communication in Australian Application No. 2019206045, dated Sep. 8, 2020.
Official Communication in Australian Application No. 2019206045, dated Sep. 9, 2020.
Official Communication in Australian Application No. 2019206045, dated Jul. 16, 2021.
Official Communication in Canadian Application No. 2,923,623, dated Dec. 8, 2020.
Official Communication in European Application No. 14850082.0, dated Aug. 31, 2016.
Official Communication in European Application No. 14850082.0, dated Sep. 15, 2020.
Official Communication in Japanese Application No. 2016-517392, dated Jun. 4, 2018.
Official Communication in Japanese Application No. 2016-517392, dated Apr. 22, 2019.

(56) References Cited

OTHER PUBLICATIONS

Official Communication in Japanese Application No. 2016-517392, dated Dec. 2, 2019.
Official Communication in Japanese Application No. 2019-236855, dated Nov. 24, 2020.
Official Communication in Japanese Application No. 2019-236855, dated Jun. 28, 2021.
Official Communication in Japanese Application No. 2019-236855, dated Dec. 17, 2021.
Official Communication in Japanese Application No. 2019-236855, dated Sep. 12, 2022.
Official Communication in Japanese Application No. 2021-176650, dated Sep. 20, 2022.
International Search Report and Written Opinion in International Application No. PCT/US2014/056598, dated Dec. 29, 2014.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Preliminary Report on Patentability and Written Opinion in International Application No. PCT/US2015/050441, dated Mar. 30, 2017.
Official Communication in Australian Application No. 2016212009, dated Sep. 6, 2019.
Official Communication in Australian Application No. 2016212009, dated May 26, 2020.
Official Communication in Australian Application No. 2016212009, dated Jul. 14, 2020.
Official Communication in Australian Application No. 2020281016, dated Nov. 24, 2021.
Official Communication in Australian Application No. 2020281016, dated Aug. 26, 2022.
Official Communication in Australian Application No. 2020281016, dated Oct. 7, 2022.
Official Communication in Australian Application No. 2020281016, dated Nov. 16, 2022.
Official Communication in Australian Application No. 2020281016, dated Nov. 23, 2022.
Official Communication in Canadian Application No. 2,972,788, dated Jan. 31, 2022.
Official Communication in Canadian Application No. 2,972,788, dated Oct. 31, 2022.
Official Communication in European Application No. 16743832.4, dated Jul. 24, 2018.
Official Communication in Japanese Application No. 2017-557269, dated Oct. 21, 2019.
Official Communication in Japanese Application No. 2017-557269, dated Jul. 13, 2020.
Official Communication in Japanese Application No. 2017-557269, dated Nov. 1, 2021.
Official Communication in Japanese Application No. 2020-181320, Sep. 21, 2021.
International Search Report and Written Opinion in International Application No. PCT/US2016/013062, dated Mar. 16, 2016.
International Preliminary Report on Patentability and Written Opinion in International Application No. PCT/US2016/013062, dated Aug. 10, 2017.
International Search Report and Written Opinion in International Application No. PCT/US2020/014985, dated Apr. 24, 2020.
International Preliminary Report on Patentability and Written Opinion in International Application No. PCT/US2020/014985, dated Dec. 2, 2021.
Invitation to Pay Additional Search Fees in International Application No. PCT/US2021/072351, dated Jan. 13, 2022.
International Search Report and Written Opinion in International Application No. PCT/US2021/072351, dated Mar. 18, 2022.
International Search Report and Written Opinion in International Application No. PCT/US2021/017643, dated Apr. 28, 2021.
International Search Report and Written Opinion in International Application No. PCT/US2022/070851, dated May 13, 2022.
Official Communication in European Application No. EP12749447.4, dated Mar. 23, 2023.
Official Communication in Japanese Application No. 2021-165476, dated Feb. 6, 2023.
Official Communication in Australian Application No. 2021282492, dated Feb. 6, 2023.
Official Communication in European Application No. 16743832.4, dated Jan. 26, 2023.
Official Communication in Japanese Application No. 2020-181320, Feb. 13, 2023.
International Preliminary Report on Patentability and Written Opinion in International Application No. PCT/US2021/072351, dated Jun. 1, 2023.
Invitation to Pay Additional Search Fees in International Application No. PCT/US2022/081096, dated Mar. 14, 2023.
International Search Report and Written Opinion in International Application No. PCT/US2022/081096, dated Jun. 1, 2023.
International Preliminary Report on Patentability and Written Opinion in International Application No. PCT/US2022/070851, dated Sep. 14, 2023.
Official Communication in Japanese Application No. 2019-236855, dated Mar. 4, 2024.
International Preliminary Report on Patentability and Written Opinion in International Application No. PCT/US2022/081096, dated Jun. 20, 2024.

* cited by examiner

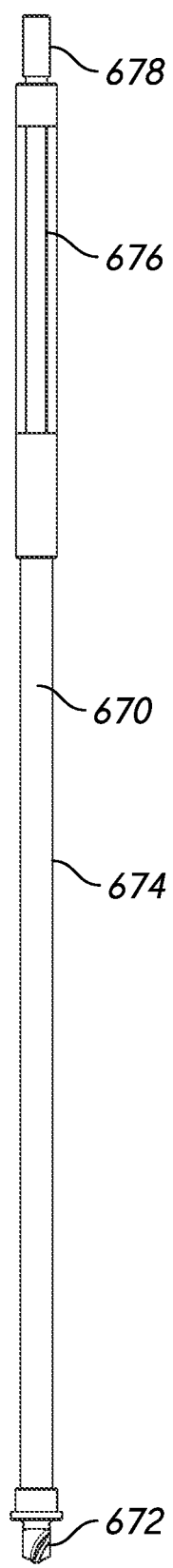
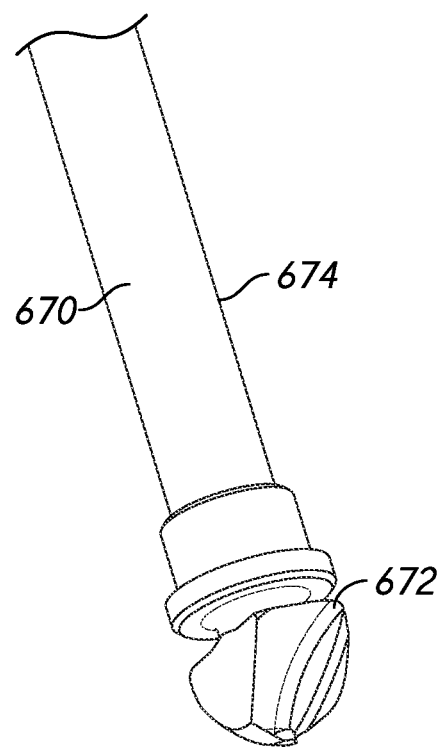
FIG. 40
FIG. 41

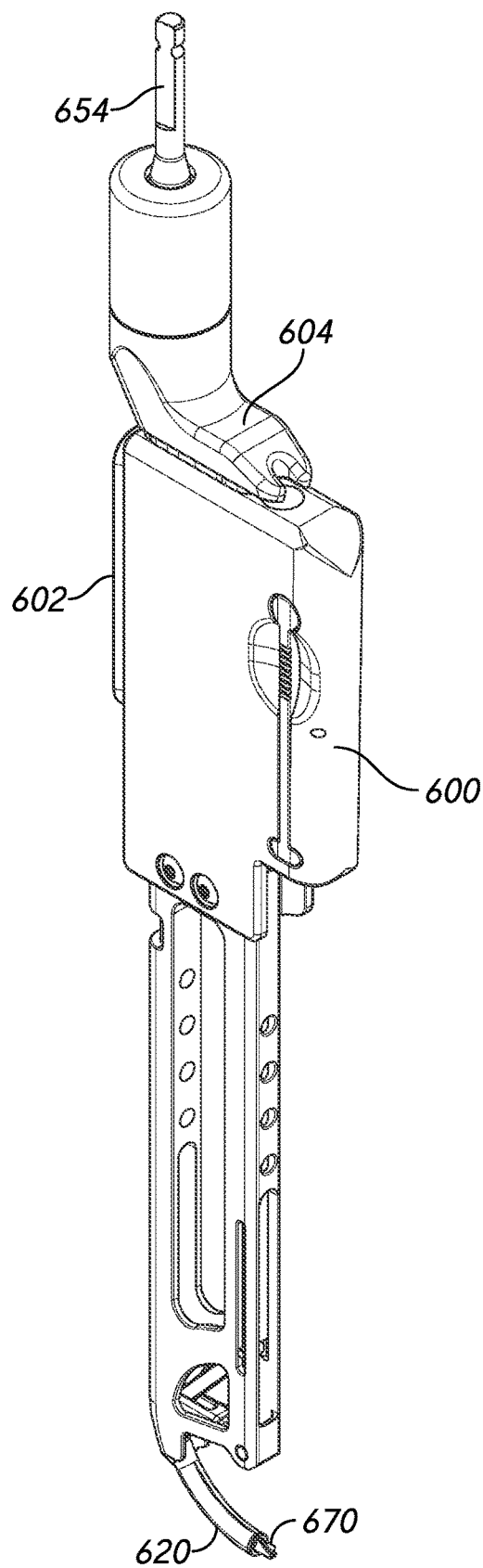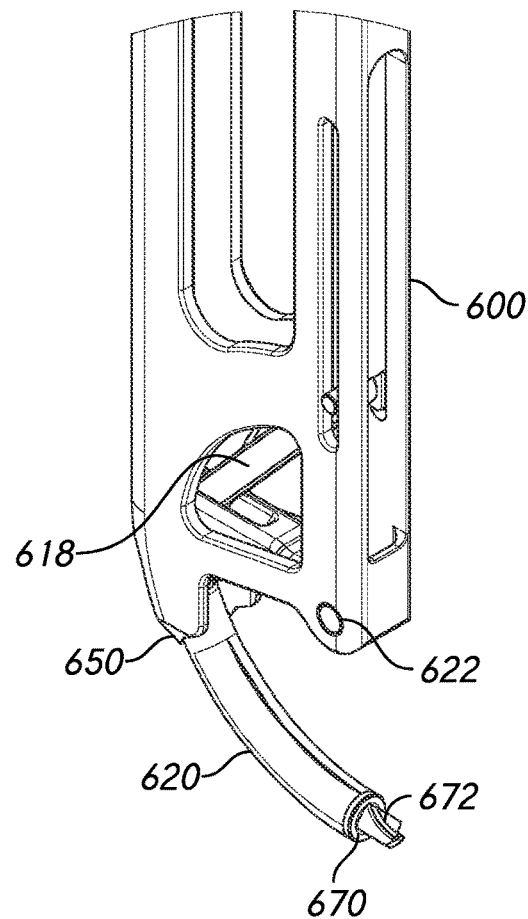
FIG. 43
FIG. 42

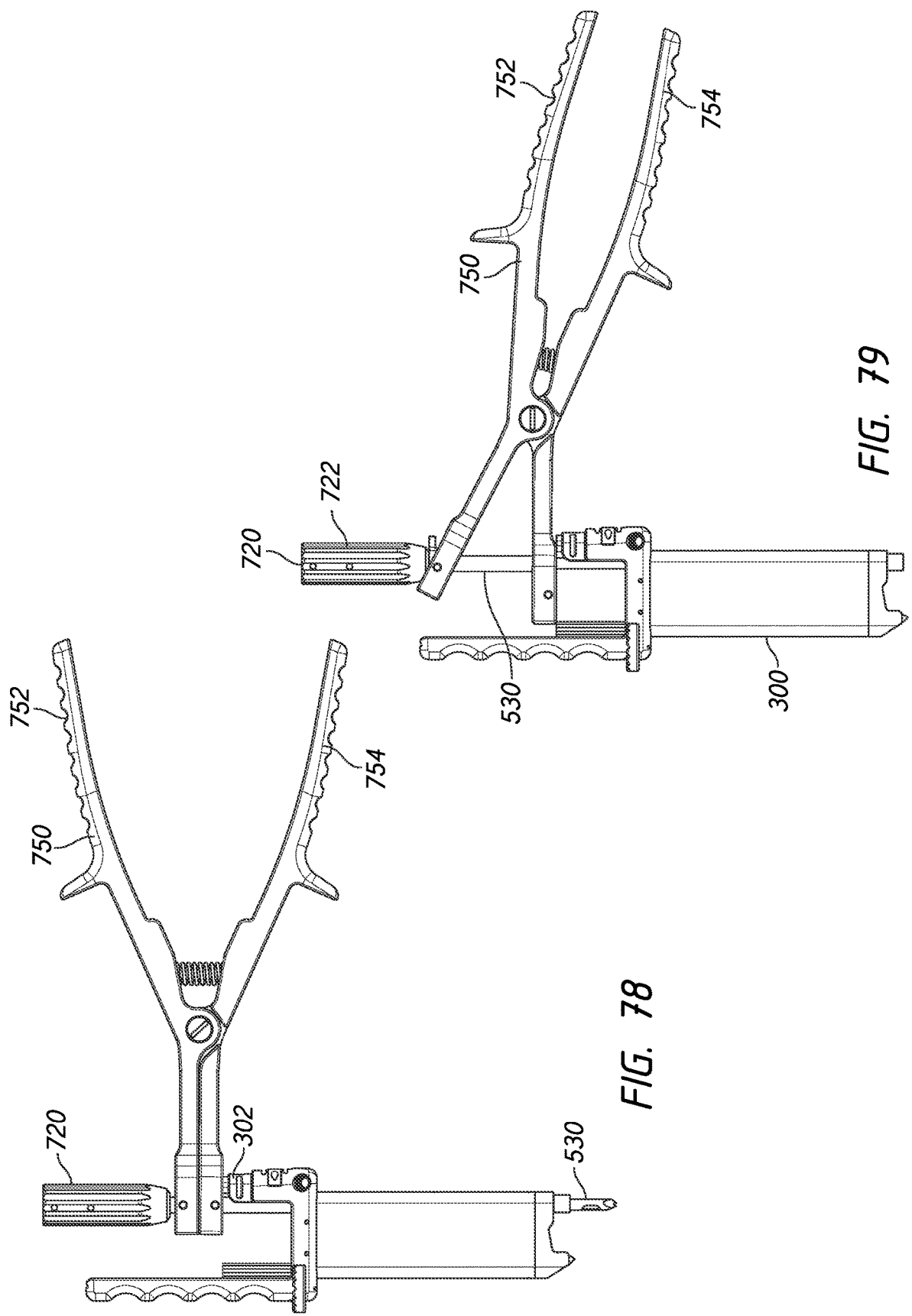

BONE TIE AND PORTAL

CROSS-REFERENCE TO RELATED APPLICATIONS

This application claims priority benefit to U.S. Provisional Patent Application No. 63/288,234, filed Dec. 10, 2021, the entirety of which is hereby incorporated by reference herein.

BACKGROUND

Field

Some embodiments described herein relate generally to systems and methods for performing spinal fusion and in particular to bone ties and portals.

Description of the Related Art

Traumatic, inflammatory, and degenerative disorders of the spine can lead to severe pain and loss of mobility. According to some studies, back and spinal musculoskeletal impairments are the leading causes of lost work productivity in the United States. Pain resulting from spinal impairment may have its source in a variety of pathologies or clinical conditions.

One source of back pain is related to degeneration of the spine, including degeneration of the discs or facets of the spine. Stabilization of the spine, including the discs and facets, may help alleviate back pain and facilitate repair of the spine.

While many technological advances have focused on the spinal disc and artificial replacement or repair of the disc, little advancement in facet repair and stabilization has been made. Issues with the facet joints and discs frequently occur together. Thus, there is a need to address the clinical concerns raised by these issues.

SUMMARY

Devices and methods are disclosed for treating the vertebral column. In some embodiments, a trephine is provided. In some embodiments, a portal is provided. In some embodiments, a tissue splitter is provided. In some embodiments, an awl is provided. In some embodiments, a drill is provided. In some embodiments, a bone tie for securing or fusing facets is provided. In some embodiments, an awl jack is provided. In some embodiments, a flush cutter is provided. In some embodiments, a head pusher is provided. In some embodiments, a tensioner is provided. In some embodiments, a method of use to treat the spine is provided.

In some embodiments, a portal system for treating the spine is provided. The portal system can include a portal. The portal can include a proximal end and a distal end. The portal can include a first passageway extending between the proximal end and the distal end. The portal can include a second passageway extending between the proximal end and the distal end. The portal can include a latch. The portal system can include a bone tie. The bone tie can include a head. The bone tie can include a body section comprising one or more gears. The bone tie can include a fastener section comprising a ratchet.

In some embodiments, the portal system can include a k-wire, wherein the first passageway is configured to receive the k-wire. In some embodiments, the portal system can include a trephine, wherein the trephine comprises a trephine shaft and a trephine blade. In some embodiments, the trephine shaft is configured to engage a shaft lock to limit or prevent translation of the trephine shaft relative to a trephine handle of the trephine. In some embodiments, the portal comprises one or more arm mounts. In some embodiments, the portal comprises a latch release button configured to disengage the latch. In some embodiments, the portal comprises a sliding feature comprising a dovetail groove. In some embodiments, the portal system can include a tissue splitter, wherein the first passageway and the second passageway are configured to receive a blade of the tissue splitter. In some embodiments, the blade is configured to retract into a tissue splitter handle when the tissue splitter engages the portal. In some embodiments, the tissue splitter comprises an indicator configured to indicate the relative position of the blade relative to the portal. In some embodiments, the tissue splitter comprises one or more latch arms configured to engage one or more alignment features of the portal. In some embodiments, the portal system can include an awl, wherein the first passageway is configured to receive the awl. In some embodiments, the latch is configured to engage a pocket of the awl to limit rotation and translation of the awl relative to the portal. In some embodiments, the awl comprises a retriever portion configured to receive the head of the bone tie. In some embodiments, the portal system can include an implant catcher configured to slide relative to the awl to retain the head of the bone tie. In some embodiments, the portal system can include an awl jack configured to retract the awl from bone. In some embodiments, the portal system can include a drill, wherein the second passageway is configured to receive the drill when the first passageway receives an awl. In some embodiments, the drill comprises a swing arm and a drill bit, wherein the swing arm and the drill bit are configured to advance to drill a curved lumen in bone. In some embodiments, the swing arm is aligned with a retriever portion of the awl when the awl and the drill are coupled to the portal. In some embodiments, the portal system can include a tensioner configured to apply tension to a free end of the bone tie after the one or more gears engage the ratchet to form a loop.

In some embodiments, a method for treating the spine is provided. The method can include positioning a portal. In some embodiments, the portal comprises a portal body comprising a lumen. In some embodiments, the portal body engages the anatomy of a patient. The method can include inserting a drill into the portal. The method can include forming a curved lumen with the drill inserted into the portal. The method can include passing a bone tie through the curved lumen.

In some embodiments, the method can include positioning a JAMSHIDI needle into a pedicle. In some embodiments, the method can include positioning a k-wire into cannulation of a JAMSHIDI needle. In some embodiments, the method can include preparing hypertrophic facets. In some embodiments, the method can include positioning a trephine relative to a k-wire. In some embodiments, the method can include rotating a trephine to seat a trephine blade on a facet joint. In some embodiments, the method can include coupling the portal and a tissue splitter. In some embodiments, the method can include inserting a tissue splitter and the portal until the tissue splitter and the portal bottom out on a pedicle. In some embodiments, the method can include confirming the position of the portal. In some embodiments, the method can include sliding an awl over a k-wire and through the portal. In some embodiments, the method can include advancing an awl into a pedicle. In some embodiments, inserting the drill into the portal further comprises locking the drill. In some embodiments, forming a curved lumen further comprises forming a curved lumen from a lamina to a pedicle. In some embodiments, the method can include inserting an implant shuttle into the portal. In some embodiments, the method can include feeding the bone tie through the curved lumen. In some embodiments, the method can include sliding an implant catcher relative to an awl. In some embodiments, the method can include advancing the bone tie until a head of the bone tie is positioned within an awl. In some embodiments, the method can include tensioning the bone tie. In some embodiments, the method can include engaging one or more gears of the bone tie with a ratchet of the bone tie to form a loop. In some embodiments, the method can include applying tension to a free end of the bone tie after the bone tie forms a loop.

BRIEF DESCRIPTION OF THE DRAWINGS

The structure and method of use will be better understood with the following detailed description of embodiments, along with the accompanying illustrations, in which:

FIG. 40 is a front view of a drill bit.
FIG. 41 is a distal view of the drill bit of FIG. 40.
FIG. 42 is a perspective view of the drill of FIG. 34 and the drill bit of FIG. 40.
FIG. 43 is a distal view of the drill of FIG. 34 and the drill bit of Figure
FIGS. 67-84 illustrate methods.

DETAILED DESCRIPTION

Figure 1:
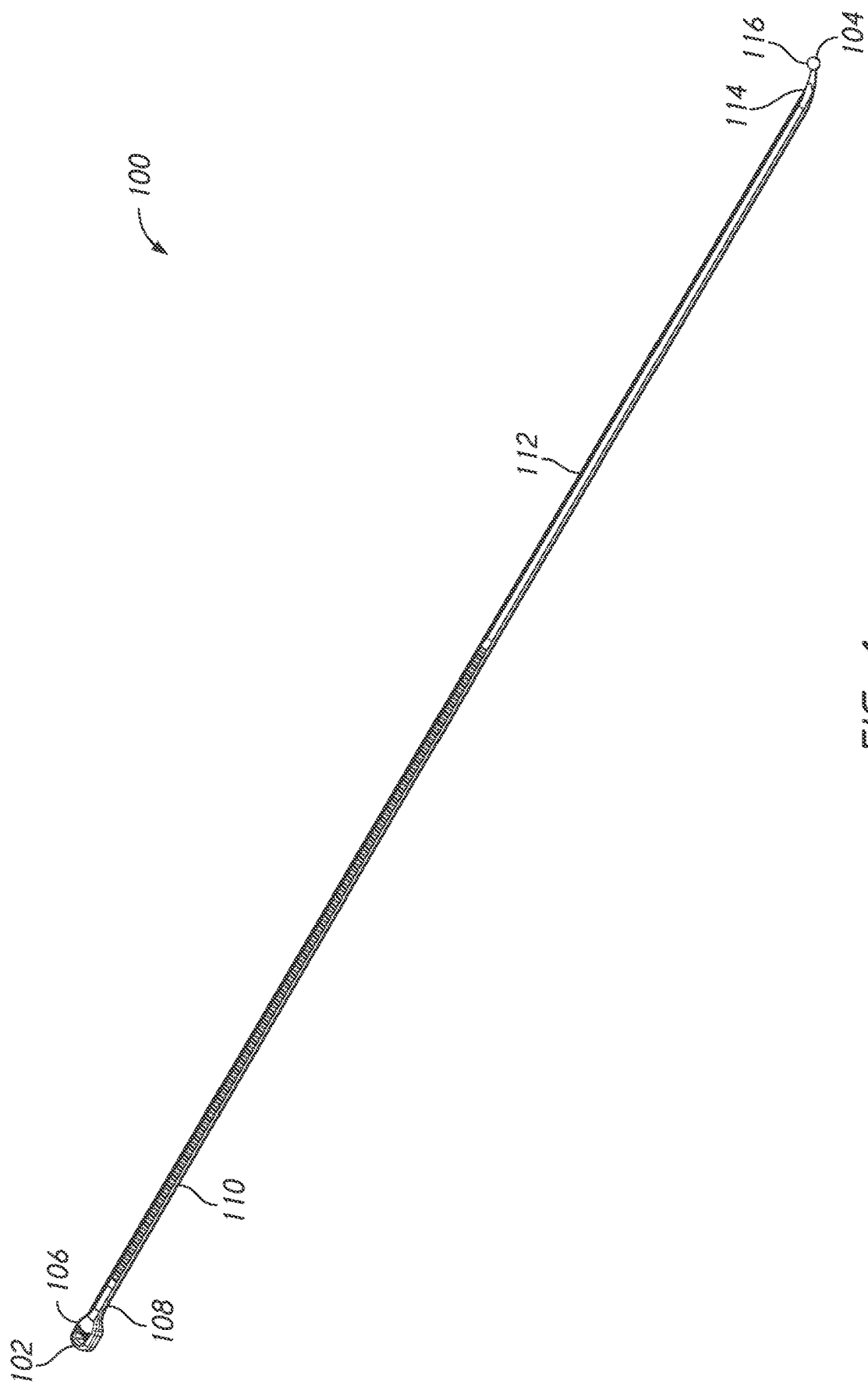
FIG. 1 is a perspective front view of an embodiment of a bone tie.

Although certain preferred embodiments and examples are disclosed below, it will be understood by those in the art that the disclosure extends beyond the specifically disclosed embodiments and/or uses of the invention and obvious modifications and equivalents thereof. Thus, it is intended that the scope should not be limited by the particular disclosed embodiments described below.

The systems and methods described herein relate to embodiments of bone ties, embodiments of portal and associated components, embodiments of drills and associated components, and methods of use. The assemblies described herein can facilitate insertion of a bone tie, as described herein. The bone tie can be inserted within a bone lumen, such as a bone lumen between adjacent vertebrae. The vertebrae can be prepared by one or more components. Various components can be positioned relative to the vertebrae. The bone lumen can be drilled and the bone tie can be passed through the lumen. One or more components described herein can facilitate the preparation of the vertebrae. One or more components described herein can facilitate the positioning of the bone tie. One or more components described herein can facilitate the fusion of the vertebrae.

1. Anatomy of the Spine

The vertebral column comprises a series of alternating vertebrae and fibrous discs that provide axial support and movement to the upper portions of the body. The vertebral column typically comprises thirty-three vertebrae, with seven cervical (C1-C7), twelve thoracic (T1-T12), five lumbar (L1-L5), five fused sacral (S1-S5) and four fused coccygeal vertebrae. Each typical thoracic vertebra includes an anterior body with a posterior arch. The posterior arch comprises two pedicles and two laminae that join posteriorly to form a spinous process. Projecting from each side of the posterior arch is a transverse, superior and inferior articular process. The facets of the superior and inferior articular processes form facet joints with the articular processes of the adjacent vertebrae. The facet joints are true synovial joints with cartilaginous surfaces and a joint capsule.

The orientation of the facet joints varies depending on the level of the vertebral column. In the C1 and C2 vertebrae, the facet joints are parallel to the transverse plane. In the C3 to C7 vertebrae, the facets are oriented at a 45-degree angle to the transverse plane and parallel to the frontal plane, respectively. This orientation allows the facet joints of the cervical vertebrae to flex, extend, lateral flex, and rotate. At a 45-degree angle in the transverse plane, the facet joints of the cervical spine can guide, but do not limit, the movement of the cervical vertebrae. For the thoracic vertebrae, the facets are oriented at a 60-degree angle to the transverse plane and a 20-degree angle to the frontal plane, respectively. This orientation can provide lateral flexion and rotation, but only limited flexion and extension. For the lumbar region, the facet joints are oriented at 90-degree angles to the transverse plane and a 45-degree angle to the frontal plane, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, *Orthop. Clin. North Am.*, 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

2. Bone Tie

Figure 2:
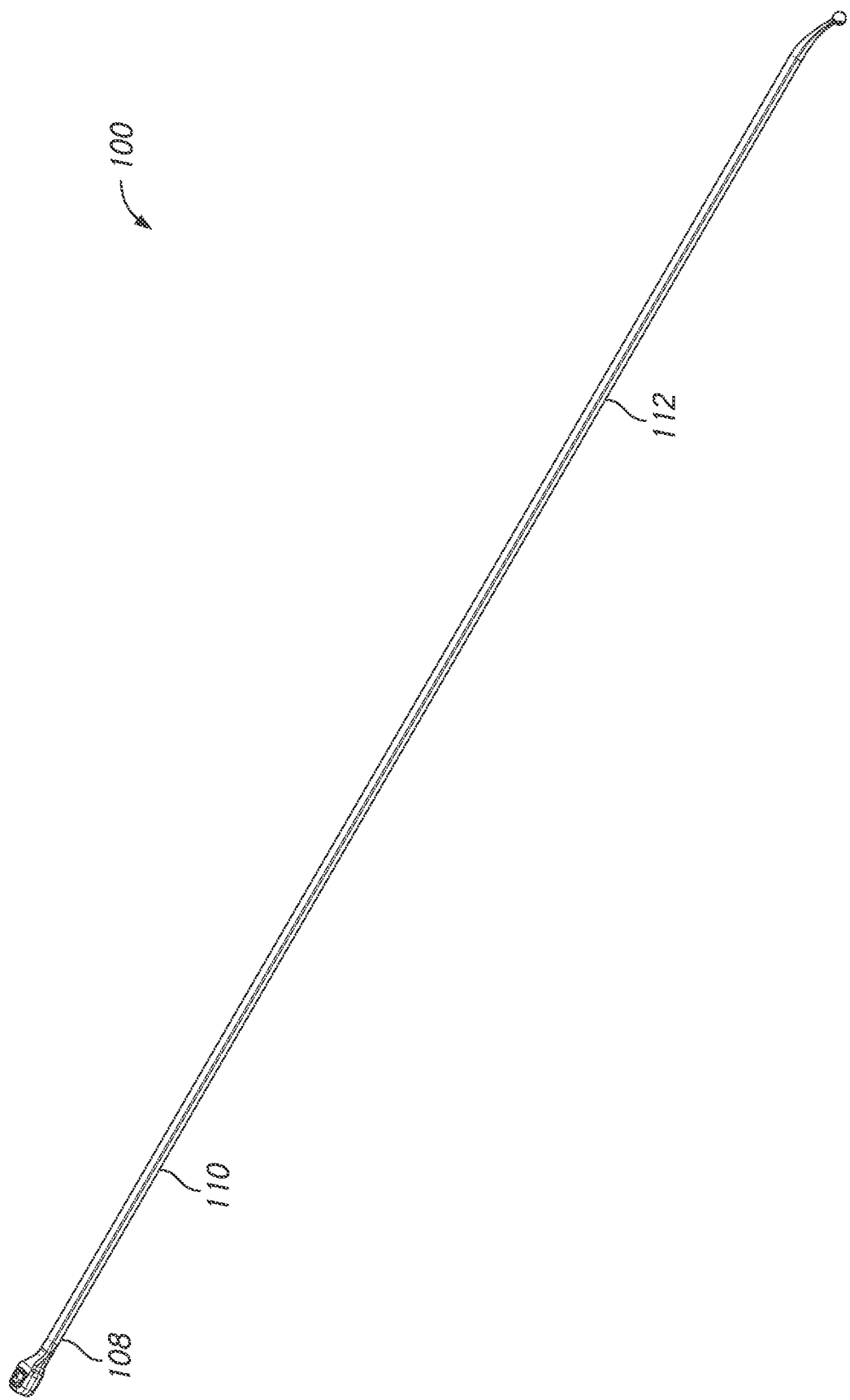
FIG. 2 is a perspective back view of the bone tie of FIG. 1.
Figure 3:
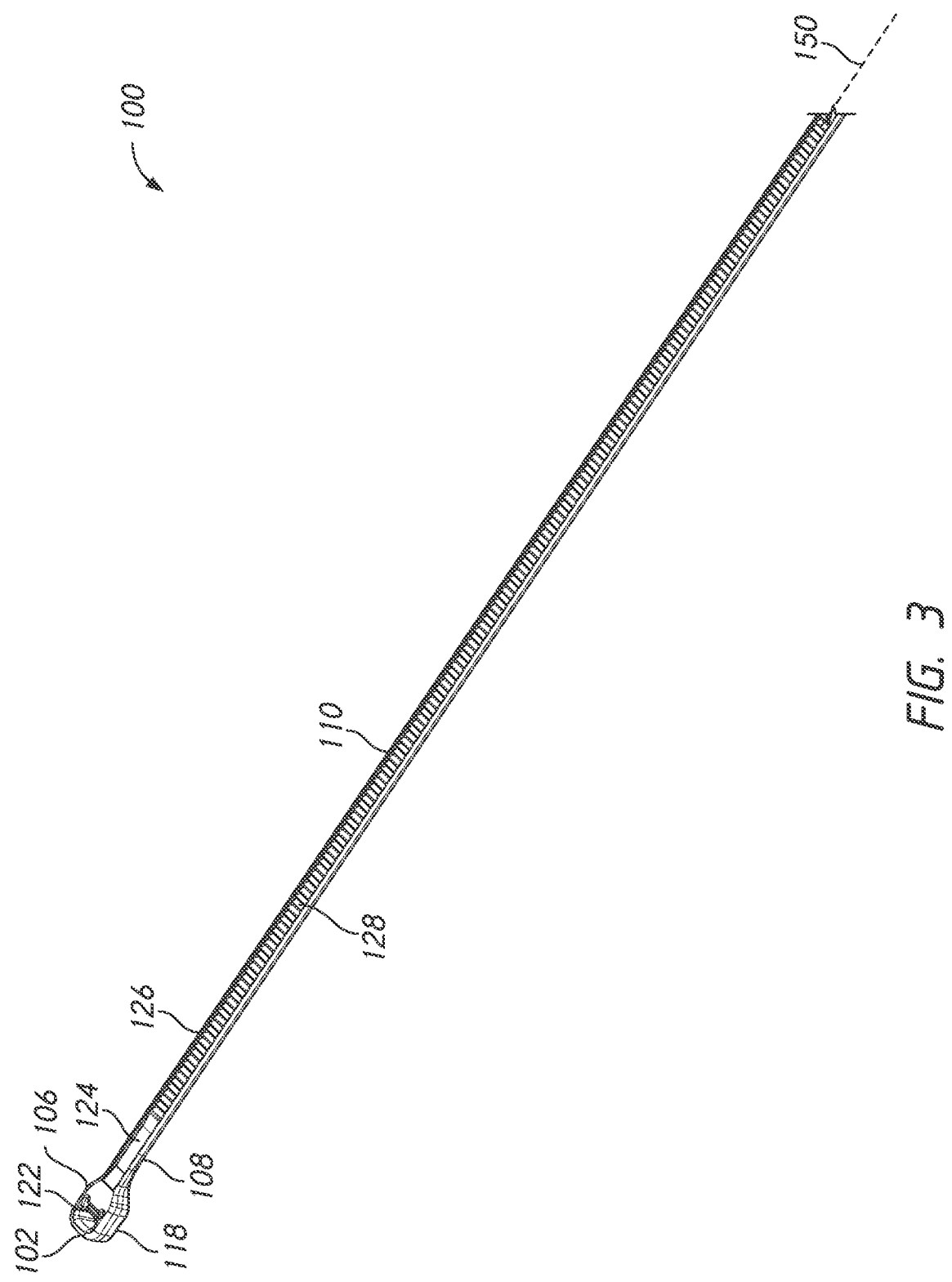
FIG. 3 is a perspective view of a proximal portion of the bone tie of FIG. 1.
Figure 4:
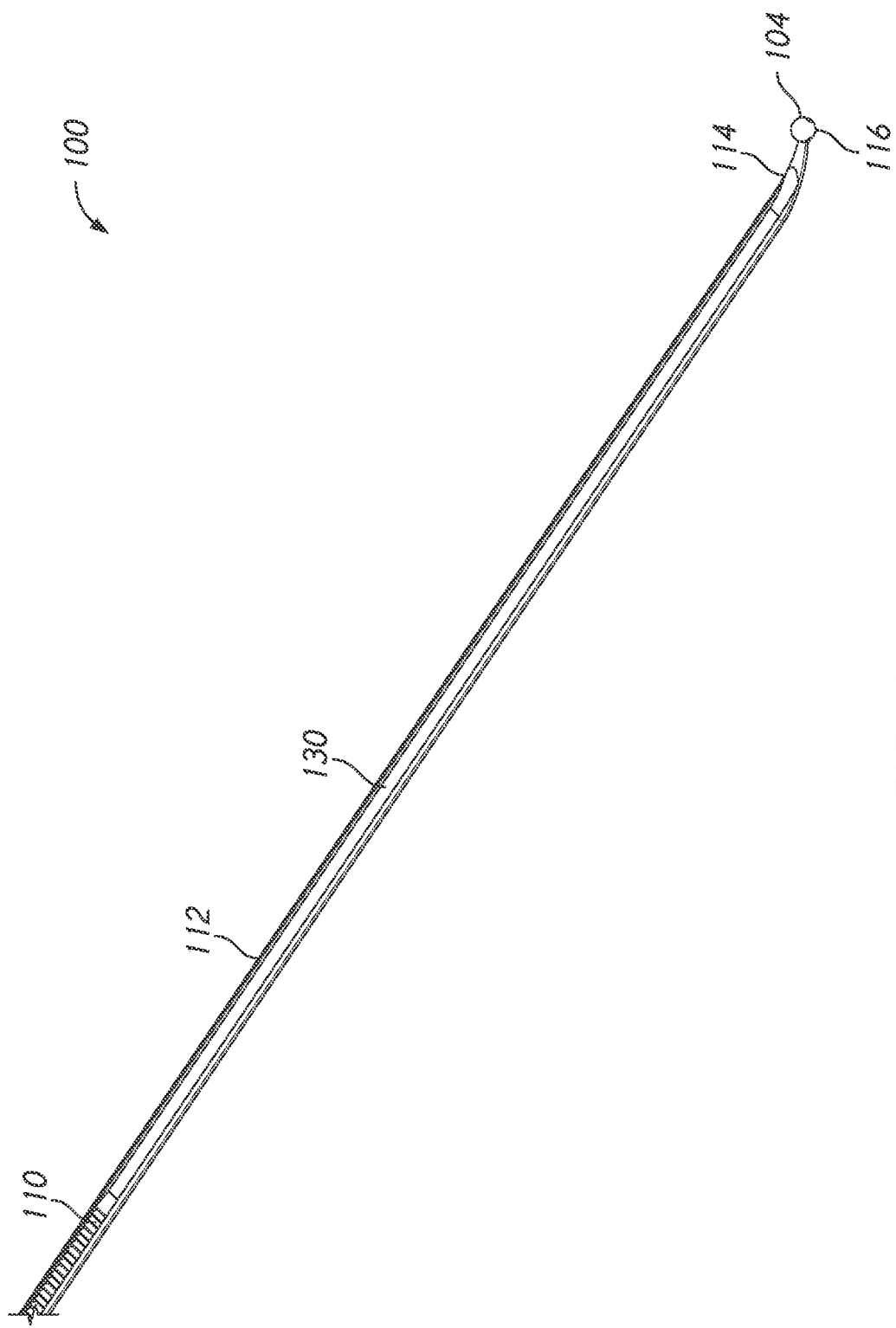
FIG. 4 is a perspective view of a distal portion of the bone tie of FIG. 1.
Figure 5:
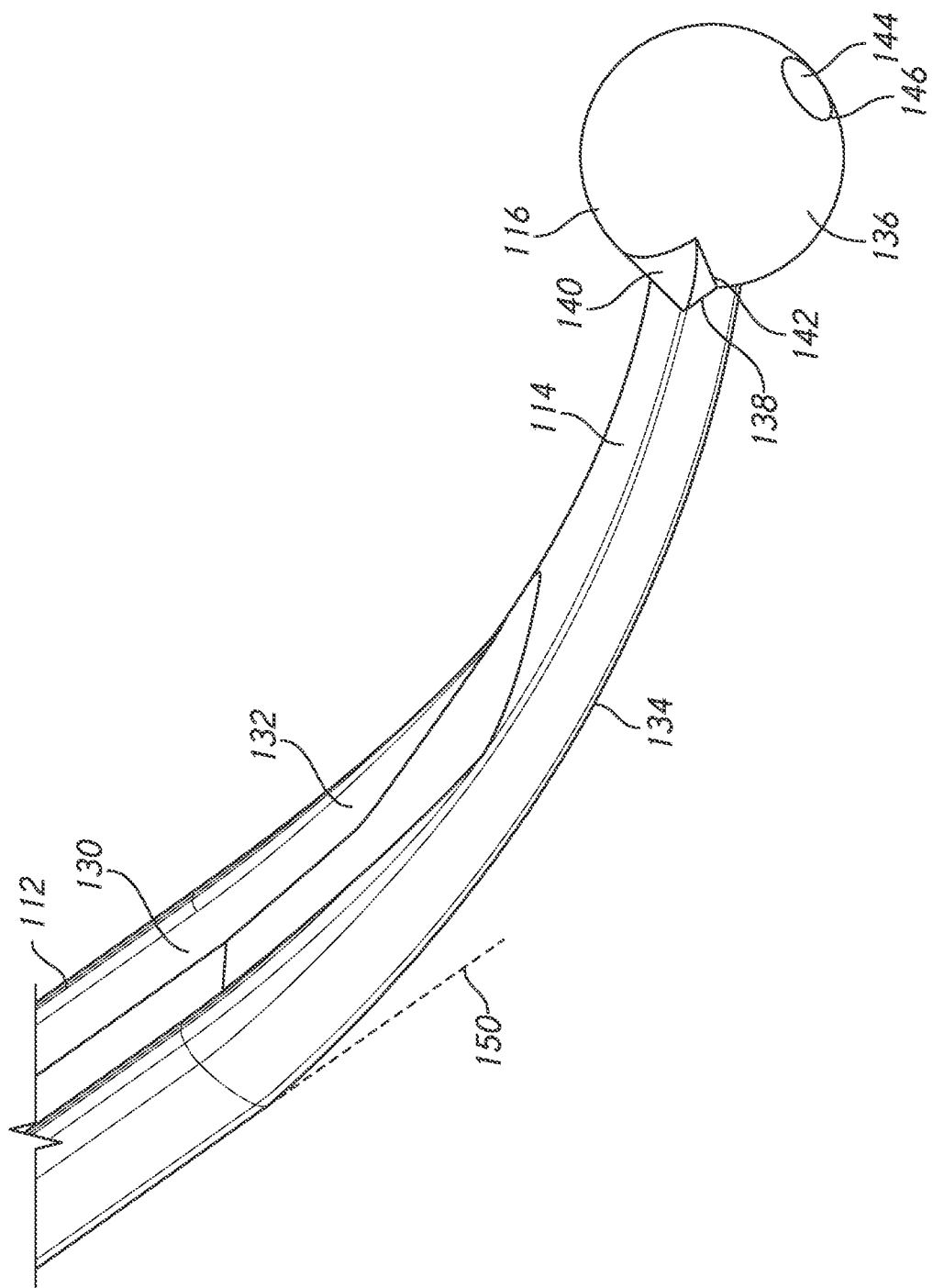
FIG. 5 is an enlarged perspective view of a distal portion of the bone tie of FIG. 1.

FIGS. 1-5 depict views of an embodiment of a bone tie 100. FIG. 1 illustrates a perspective front view. FIG. 2 illustrates a perspective back view. FIG. 3 illustrates a perspective view of a proximal portion of the bone tie 100. FIG. 4 illustrates a perspective view of a distal portion of the bone tie 100. FIG. 5 illustrates an enlarged perspective view of a distal portion of the bone tie 100.

The bone tie 100 can be a generally elongate member. The bone tie 100 can comprise a proximal end 102 and a distal end 104. The bone tie 100 can include a length between the proximal end 102 and the distal end 104. The proximal end 102 can be configured to be near the hands of the user when the user is manipulating the bone tie, as described herein. The distal end 104 can be configured to be inserted into a bone lumen, as described herein. The distal end 104 can be configured to be the first portion of the bone tie 100 that is inserted into a lumen, as described herein. The distal end 104 can be the leading end of the bone tie 100. In some methods of use, the proximal end 102 extends away from the vertebrae during insertion of the bone tie 100. In some methods of use, the proximal end 102 is held by the user. In some methods of use, the proximal end 102 is unconstrained during insertion of the bone tie 100. In some methods of use, the bone tie 100 near the distal end 104 can be fed through a bone lumen as described herein. In some methods of use, a portion of the bone tie 100 near the proximal end 102 extends beyond bone lumen.

The bone tie 100 can include one or more sections along the length of the bone tie 100. The sections can have a different shape, configuration, or function than an adjacent section of the bone tie 100. In some embodiments, one or more non-adjacent sections can have the same shape, configuration, or function as another section of the bone tie 100. In some embodiments, one or more additional sections are provided. In some embodiments, one or more of the sections provided herein are omitted.

The bone tie 100 can include a fastener section 106. The fastener section 106 can be located at or near the proximal end 102. The fastener section 106 can include any mechanism configured to secure the fastener section 106 to another section of the bone tie 100. The fastener section 106 can include a mechanism that allows the bone tie 100 to be secured in a single direction of travel such as a ratchet. The fastener section 106 can include a mechanism that allows the bone tie 100 to be secured in two directions of travel such as a pair of gears.

The bone tie 100 can include a first section 108. The first section 108 can be closer to the proximal end 102 than the distal end 104. The first section 108 can have a first cross-sectional shape. The first section 108 can extend distally from the fastener section 106. The bone tie 100 can include a second section 110. The second section 110 can be closer to the proximal end 102 than the distal end 104. The second section 110 can have a second cross-sectional shape. The second section 110 can extend distally from the first section 108. The bone tie 100 can include a third section 112. The third section 112 can be closer to the distal end 104 than the proximal end 102. The third section 112 can have a third cross-sectional shape. The third section 112 can extend distally from the second section 110.

The bone tie 100 can include a neck section 114. The neck section 114 can be closer to the distal end 104 than the proximal end 102. The neck section 114 can taper from the third section 112 toward the distal end 104. The neck section 114 can extend distally from the third section 112. The neck section 114 can facilitate rotation of the distal portion of the bone tie 100. The neck section 114 can be shaped to interface with a portion of an awl, as described herein. The neck section 114 can be shaped to extend from the awl, as described herein.

The bone tie 100 can include a head section 116. The head section 116 can be located at or near the distal end 104. The neck section 114 can taper toward the head section 116. The head section 116 can extend distally from the neck section 114. The head section 116 can facilitate retention of the distal portion of the bone tie 100 by the awl, as described herein. The head section 116 and the neck section 114 can be shaped to pivot and/or rotate relative to the awl.

FIG. 2 is a perspective back view of the bone tie 100. The bone tie 100 can have a smooth surface along the first section 108, the second section 110, and the third section 112. The bone tie 100 can have a continuous surface along the first section 108, the second section 110, and the third section 112.

FIG. 3 illustrates a perspective view of a proximal portion of the bone tie 100. The bone tie can include the proximal end 102, the fastener section 106, first section 108, and the second section 110.

The fastener section 106 can include a lumen 118. The lumen 118 can be oriented perpendicular to a longitudinal axis 150 of the bone tie 100. The bone tie 100 can include a ratchet 122 disposed within the lumen 118. The ratchet 122 is configured to deflect to allow one or gears to travel through the lumen 118 in one direction, but limit or prevent travel in another direction. The fastener section 106 can form an enlarged end of the bone tie 100. The fastener section 106 can be generally rectangular or cuboid. The fastener section 106 can have a width larger than the first section 108. The fastener section 106 can have a thickness larger than the first section 108. The fastener section 106 can include rounded edges or corners. The fastener section 106 can have any shape to accommodate the ratchet 122 disposed therewithin. The fastener section 106 can have any shape to accommodate any fastener mechanism described herein.

The first section 108 can have the first cross-sectional shape. The first cross-sectional shape can be generally rectangular or cuboid. The first cross-sectional shape can have rounded edges or corners. The first section 108 can include a width and a thickness. The first section 108 can include a groove 124. The groove 124 can reduce the thickness of the first section 108. The groove 124 can taper from the fastener section 106. The groove 124 can taper to the second section 110.

The second section 110 can have the second cross-sectional shape. The second cross-sectional shape can be generally rectangular or cuboid. The second cross-sectional shape can have rounded edges or corners. The second section 110 can include a groove 126. The groove 124 of the first section 108 can extend to the groove 126 of the second section 110. The second section 110 can include one or more gears 128. The gears 128 can be ramped surfaces. The gears 128 can form a rack. The gears 128 can be wedge surfaces. The gears 128 can be inclined upward toward the proximal end 102. The gears 128 can be inclined downward toward the distal end 104. The gears 128 can be disposed within the groove 126 of the second section 110. The first section 108 and the second section 110 can include a constant width. The first section 108 and the second section 110 can include a constant thickness. The first section 108 and the second section 110 can include a constant thickness measured along the edges of the first section 108 and the second section 110.

FIG. 4 illustrates a perspective view of a distal portion of the bone tie 100. The bone tie can include the second section 110, the third section 112, the neck section 114, the head section 116, and the distal end 104.

The third section 112 can have a third cross-sectional shape. The third cross-sectional shape can be generally rectangular or cuboid. The third cross-sectional shape can have rounded edges or corners. In some embodiments, the first cross-sectional shape and the third cross-sectional shape are the same or similar. The third section 112 can include a width and a thickness. The third section 112 can include a groove 130. The groove 130 can reduce the thickness of the third section 112. The groove 130 can taper from the second section 110. The groove 130 can taper to the neck section 114.

Two or more of the first section 108, the second section 110, and the third section 112 can include a constant width. Two or more of the first section 108, the second section 110, and the third section 112 can include a constant thickness. Two or more of the first section 108, the second section 110, and the third section 112 can include a constant thickness measured along the edges of the respective sections. The bone tie 100 can have a constant width along a substantial portion of the length. The bone tie 100 can have a constant thickness along a substantial portion of the length.

FIG. 5 illustrates an enlarged view of the distal portion of the bone tie 100. The bone tie 100 can include the neck section 114. The neck section 114 tapers along the width. The neck section 114 tapers from a larger width near the third section 112 to a smaller width near the head section 116. The neck section 114 can include a groove 132. The groove 132 can reduce the thickness of the neck section 114. The groove 132 of the neck section 114 can extend from the groove 130 of the third section 112.

The neck section 114 can lie in a plane along the longitudinal axis 150 of the bone tie 100 or the neck section 114 can include a curve 134. The curve 134 can have a constant radius of curvature. The curve 134 can match the curvature formed by a drill, as described herein. The curve 134 can facilitate the passage of the head section 116 along a curved bone lumen. The curve 134 can facilitate the passage of the head section 116 toward an awl, as described herein. Two or more of the first section 108, the second section 110, and the third section 112 can be planar. The bone tie 100 can lie in a plane along a substantial portion of the length. The curve 134 can extend from the plane of the bone tie. The curve 134 can extend upward from the grooves 124, 126, 130, 132 of the bone tie 100. The curve 134 can extend upward from the gears 128 of the second section 110. The curve 134 can extend away from the longitudinal axis 150 of the bone tie 100.

The bone tie 100 can include the head section 116. The head section 116 can include a head 136. The head 136 can be rounded. The head 136 can be spherical. The head 136 can extend to the distal end 104 of the bone tie 100. The head section 116 can include a flange 138. The flange 138 can be positioned on the head 136. The flange 138 can be a rounded bill that extends from the head 136. The flange 138 can include a first tapered surface 140 and a second tapered surface 142. The first tapered surface 140 and the second tapered surface 142 can have different slopes. The second tapered surface 142 can form a ledge by which the head section 116 or head 136 can be grasped. The first tapered surface 140 and the second tapered surface 142 extend to the neck section 114.

The bone tie 100 can include a marker 144. The marker 144 can facilitate visualization of the bone tie 100, or a portion thereof. The marker 144 can facilitate visualization that the head 136 is disposed relative to the awl, as described herein. In the illustrated embodiment, the head 136 can include the marker 144. The head 136 can include a bore 146. The bore 146 can extend from an edge of the head 136 inward toward or past the center of the head 136. The marker 144 can be disposed within the bore 146. The marker 144 can be a radiopaque marker. The marker 144 can be formed of a metal or other radiopaque material. The marker 144 can identify the distal end 104 of the bone tie 100. In some embodiments, the bone tie 100 comprises a non-radiopaque material. In some embodiments, one or more radiopaque markers can be embedded in or on the bone tie 100 to assist in placement or monitoring of the bone tie 100 under radiographic visualization.

The bone tie 100 can be a flexible fastening band. The bone tie 100 can include the proximal end portion 102 and the distal end portion 104. The distal end portion 104 can be passed through the bone lumen. The head 136 can be captured. The head section 116 and the neck section 114 can rotate as the head section 116 is pulled proximally. The proximal end portion 102 and the distal end portion 104 can extend from the bone lumen. A portion of the bone tie 100 can be disposed within the bone lumen. In some embodiments, the head section 116 can be removed, as described herein. The neck section 114 can be advanced through the lumen 118 of the fastener section 106. When the neck section 114 is advanced, the ratchet 122 can extend into the groove 132. The third section 112 can be advanced through the lumen 118 of the fastener section 106. When the third section 112 is advanced, the ratchet 122 can extend into the groove 130. The second section 110 can be advanced through the lumen 118 of the fastener section 106. When the second section 110 is advanced, the ratchet 122 can extend into the groove 126. The ratchet 122 can engage the gears 128. The ratchet 122 can allow the second section 110 to travel through the lumen 118 in one direction, but limit travel through the lumen 118 in the opposite direction. The bone tie 100 can form a loop. A portion of the bone tie 100 can be disposed within the bone lumen and the loop can become smaller as the sections 108, 110, 112 are passed through the lumen 118 of the fastener section 106. The third section 112 can form a free end. The second section 110, or a portion thereof, can form the free end. The free end of the bone tie 100 can be trimmed, leaving the loop formed by the bone tie 100.

The bone tie 100 can be configured for altering the motion at the facet joints of the vertebral column. In some embodiments, the bone tie 100 can prevent motion of the facet joint. In some embodiments, the bone tie 100 can limit or reduce motion of the facet joint. In some embodiments, the bone tie 100 can limit motion to a range depending on the tightening of the loop of the bone tie 100. In some methods of use, the bone tie 100 promotes fusion of the facet joints.

The bone tie 100 can be configured for altering the spacing at the facet joints of the vertebral column. In some embodiments, the bone tie 100 can reduce the spacing. In some embodiments, the bone tie 100 can maintain the anatomical spacing. The bone tie 100 can be a retaining member for anchoring a prosthesis or implant within the facet joint. In some embodiments, the bone tie 100 can pass through a central opening of the prosthesis or implant when the prosthesis or implant is inserted within the facet joint space. The bone tie 100 can be adapted for securing the location of the prosthesis or implant with respect to at least one of the articular surfaces.

The prosthesis or implant can have any shape or configuration. The prosthesis or implant can be substantially disc shaped. The first side of the prosthesis or implant can be concave, convex, or flat. The second side of the prosthesis or implant can be concave, convex, or flat. The shape can be determined based on a shape of a bone portion that the first side and the second side are configured to contact. In some embodiments, the prosthesis or implant fits entirely within the joint disc space. The prosthesis or implant can include any biocompatible material, e.g., stainless steel, titanium, PEEK, nylon, etc.

The bone tie 100 can have a width of 0.5 mm, 1 mm, 1.5 mm, 2 mm, 2.5 mm, 3 mm, 3.5 mm, 4 mm, or any range of two of the foregoing values. The width of the bone tie 100 can vary along the length of the bone tie 100. The bone tie 100 can have a thickness of 0.5 mm, 1 mm, 1.5 mm, 2 mm, 2.5 mm, 3 mm, 3.5 mm, 4 mm, or any range of two of the foregoing values. The thickness of the bone tie 100 can vary along the length of the bone tie 100. The bone tie 100 can have a length of 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, or any range of two of the foregoing values. For example, the bone tie 100 can have a length of 175 mm. In some embodiments, the second section 110 or the gears 128 can have a length of 5 mm, 10 mm, 15 mm, 20 mm, 25 mm, 30 mm, 35 mm, 40 mm, 45 mm, 50 mm, 60 mm, 65 mm, 70 mm, 75 mm, 80 mm, or any range of two of the foregoing values.

The bone tie 100 can be manufactured from any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the materials described herein. The bone tie 100 can include any biocompatible material, e.g., stainless steel, titanium, PEEK, nylon, etc. In some embodiments, the bone tie 100 comprises at least two materials. The bone tie 100 can include a reinforcement piece disposed within the bone tie 100. By selecting a particular configuration and the one or more materials for the bone tie 100, the bone tie 100 can be designed to have the desired flexibility and resiliency.

In some embodiments, the bone tie 100 can form a unitary structure. The bone tie 100 can be integrally formed from the proximal end 102 to the distal end 104. In some embodiments, the bone tie 100 can include one or more unitarily formed sections along the length of the bone tie 100. One or more of the fastener section 106, the first section 108, the second section 110, the third section 112, the neck section 114, and the head section 116 can be unitarily formed. In some embodiments, the bone tie 100 can include one or more separately formed sections along the length of the bone tie 100. One or more of the fastener section 106, the first section 108, the second section 110, the third section 112, the neck section 114, and the head section 116 can be separately formed. In some embodiments, the marker 144 is separately formed. In some embodiments, the bone tie 100 can form a monolithic structure. The bone tie 100 can be monolithically formed or separately formed. The bone tie 100 can be formed of the same or similar material. The sections of the bone tie 100 can be formed of the same or similar construction. In some embodiments, the bone tie 100 is formed from an injection molding process.

In some embodiments, the shape of the first section 108, the second section 110, and/or the third section 112 can be determined based on the shape of an artificial lumen formed through vertebrae. In some embodiments, the shape of the artificial lumen is cylindrical and the shape of the head 136 can be rounded or spherical to allow the head 136 to slideably advance through the artificial lumen. In some embodiments, the shape of the artificial lumen has a cross-sectional dimension or diameter greater than the cross-sectional dimension or diameter of the head 136 to allow the head 136 to slideably advance through the artificial lumen. The head 136 can have a larger cross-sectional dimension or diameter than the first section 108, the second section 110, the third section 112, and the neck section 114 to allow the first section 108, the second section 110, the third section 112, and the neck section 114 to easily slide within the artificial lumen.

In some embodiments, the characteristic of the bone tie 100 can vary along the length of the bone tie 100. The characteristics can vary between one or more of the fastener section 106, the first section 108, the second section 110, the third section 112, the neck section 114, and the head section 116. In some embodiments, each section has different characteristics. In some embodiments, the flexibility of the bone tie 100 varies along the length of the bone tie 100. In some embodiments, the torsional strength of the bone tie 100 varies along the length of the bone tie 100. In some embodiments, the resistance to deformation or elongation of the bone tie 100 varies along the length of the bone tie 100. In some embodiments, the characteristics of the bone tie 100 vary based, at least in part, on the shape of the various sections.

In some embodiments, the characteristics of the bone tie 100 vary based on the material of the various sections. In some embodiments, the characteristics of the bone tie 100 vary along the length based, at least in part, on a reinforcement piece. The reinforcement piece can be separately formed from or integrally formed with the bone tie 100. The reinforcement piece can comprise a different material or material property. In some embodiments, the reinforcement piece is disposed within a section of the bone tie 100. The reinforcement piece can be disposed within the fastener section 106, the first section 108, the second section 110, the third section 112, the neck section 114, the head section 116, any combination of the foregoing, or disposed only within one or more sections of the foregoing. The reinforcement piece can increase the strength of a section of the bone tie 100. In some embodiments, the reinforcement piece has a substantially uniform shape. The shape, material, or other characteristics of the reinforcement piece can be selected depending on the desired bending and/or torsion characteristics of the material chosen. The reinforcement piece can increase or decrease bending strength. The reinforcement piece can increase or decrease torsion strength. Any shape, material, or other property of the reinforcement piece can be selected to achieve the desired bending and/or torsion strength of the bone tie 100. In some embodiments, the reinforcement piece is radiopaque. In some embodiments, the reinforcement piece is radiolucent.

3. Vertebrae Preparation

Figure 6:
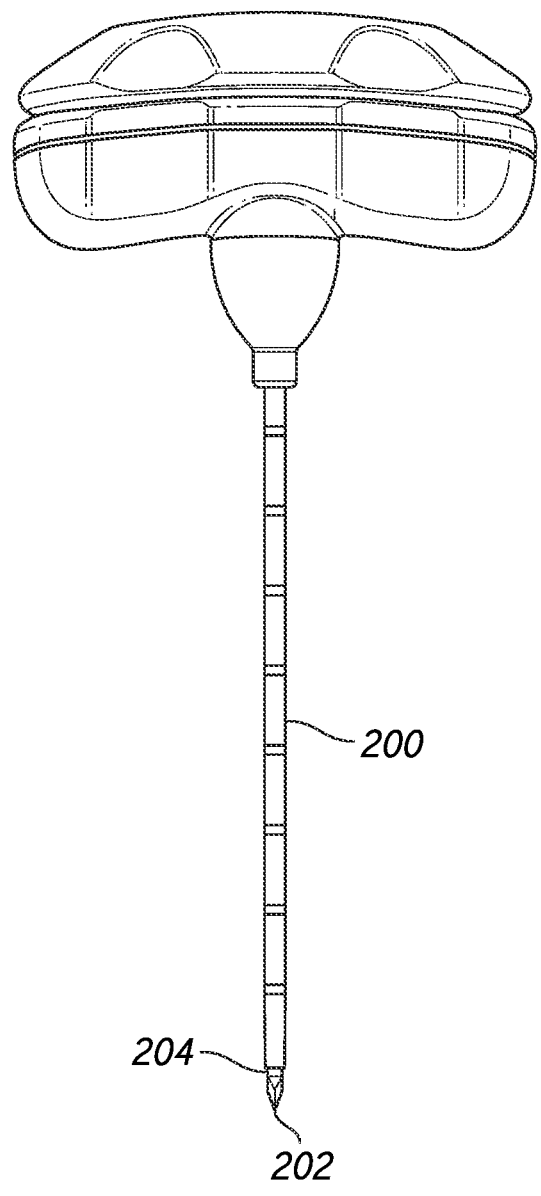
FIG. 6 is a front view of a JAMSHIDI needle.
Figure 7:
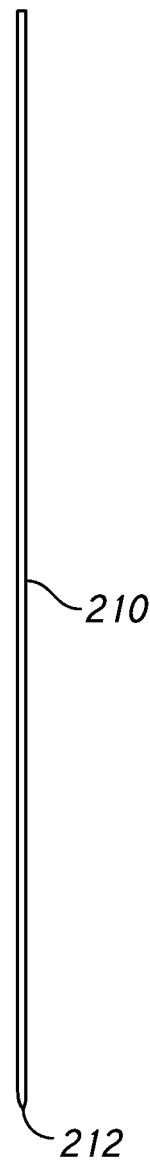
FIG. 7 is a front view of a k-wire.
Figure 8:
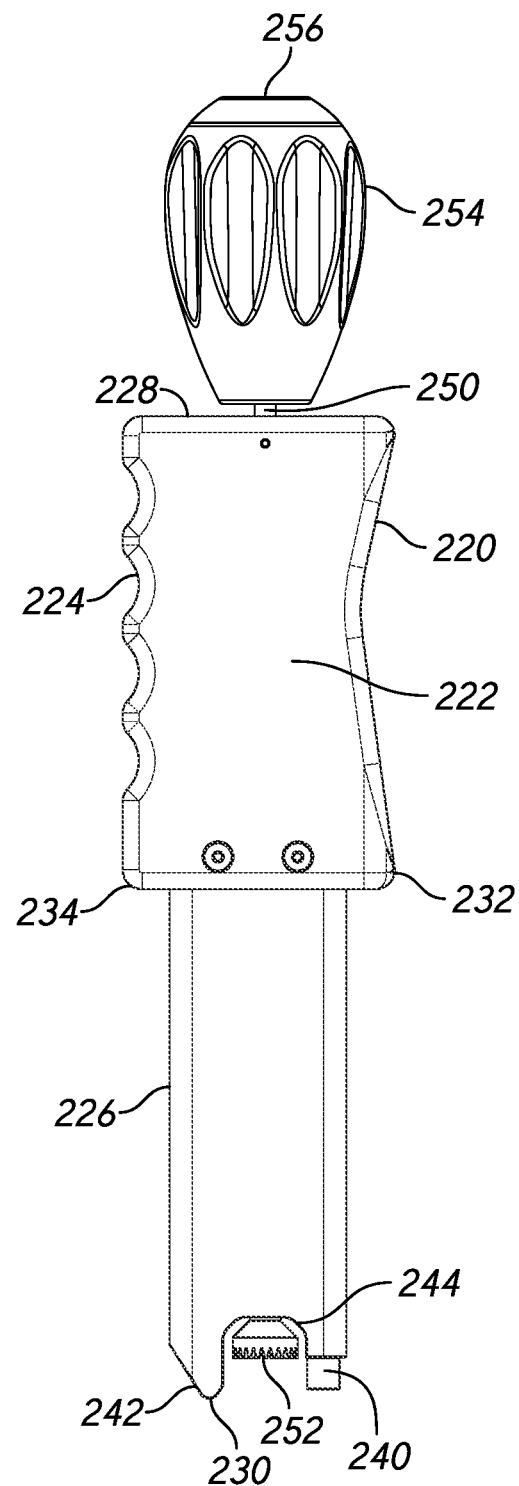
FIG. 8 is a front view of a trephine.
Figure 9:
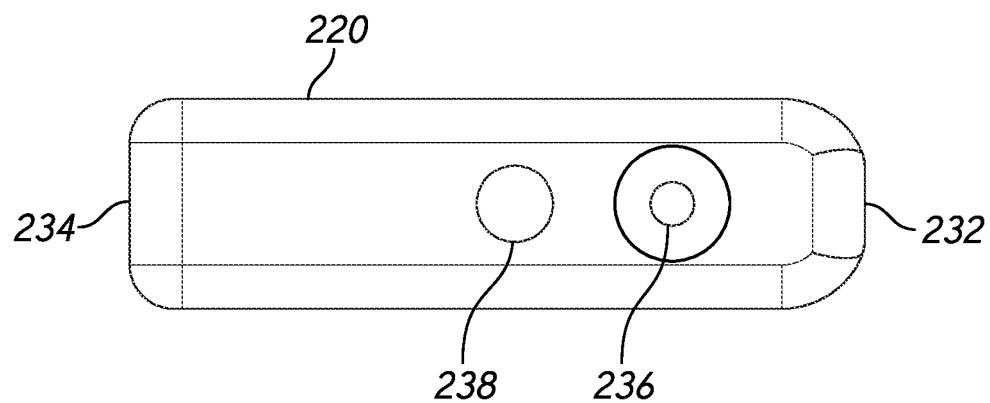
FIG. 9 is a proximal view of the trephine of FIG. 8.
Figure 10:
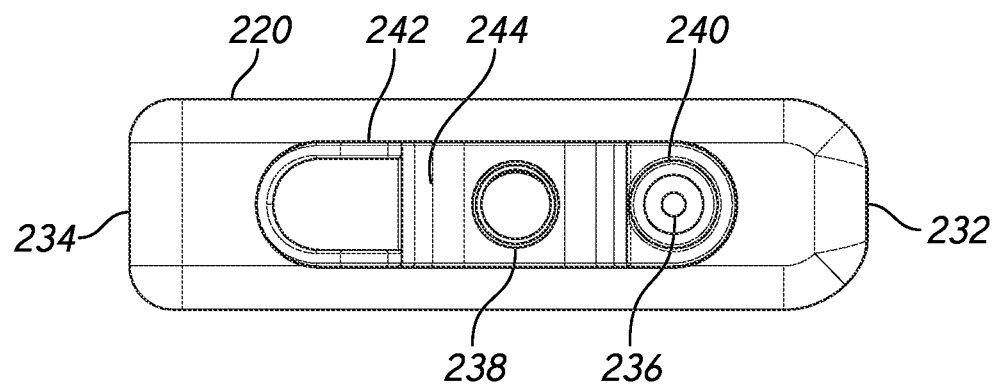
FIG. 10 is a distal view of the trephine of FIG. 8.
Figure 11:
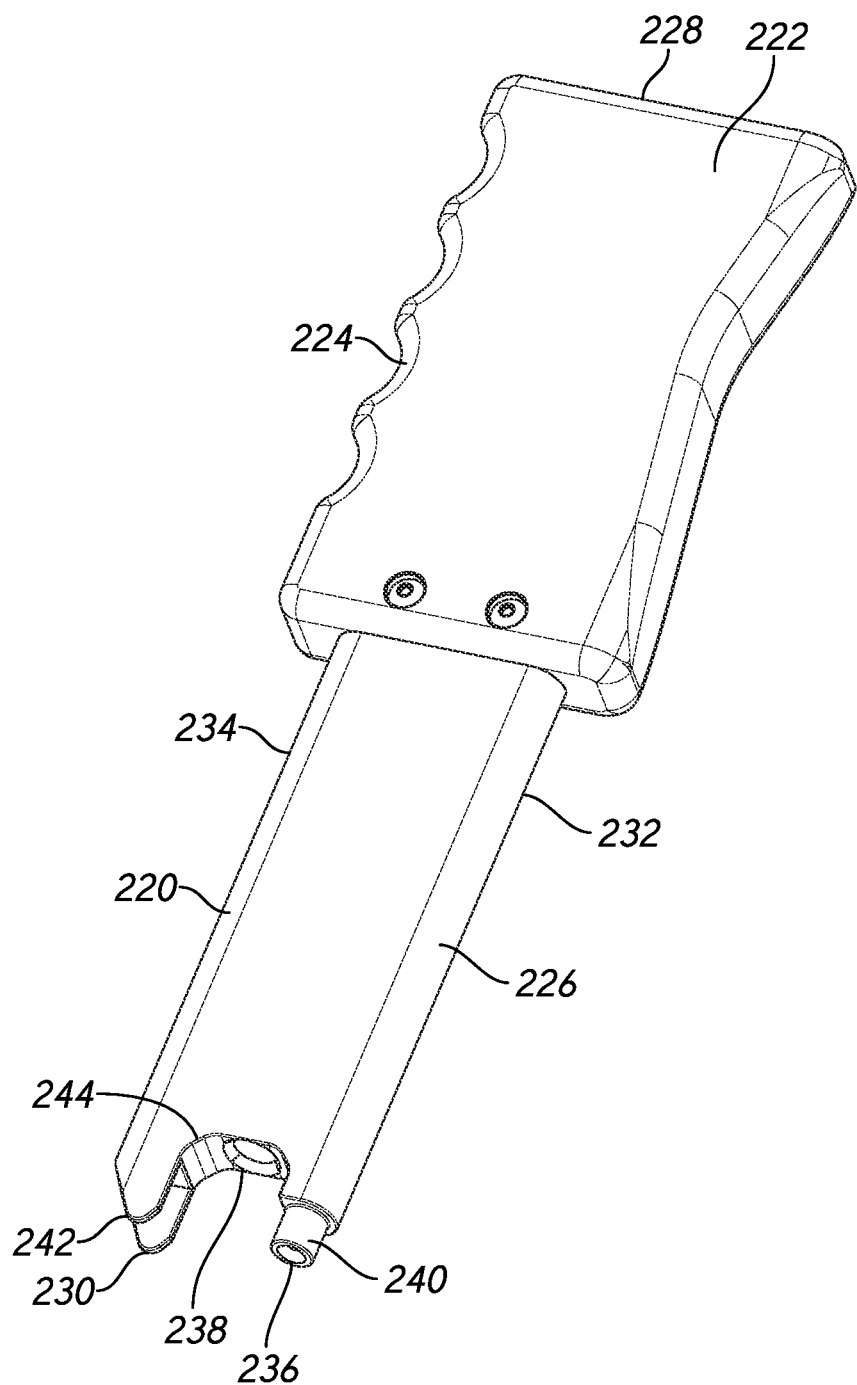
FIG. 11 is a perspective view of the trephine of FIG. 8.
Figure 13:
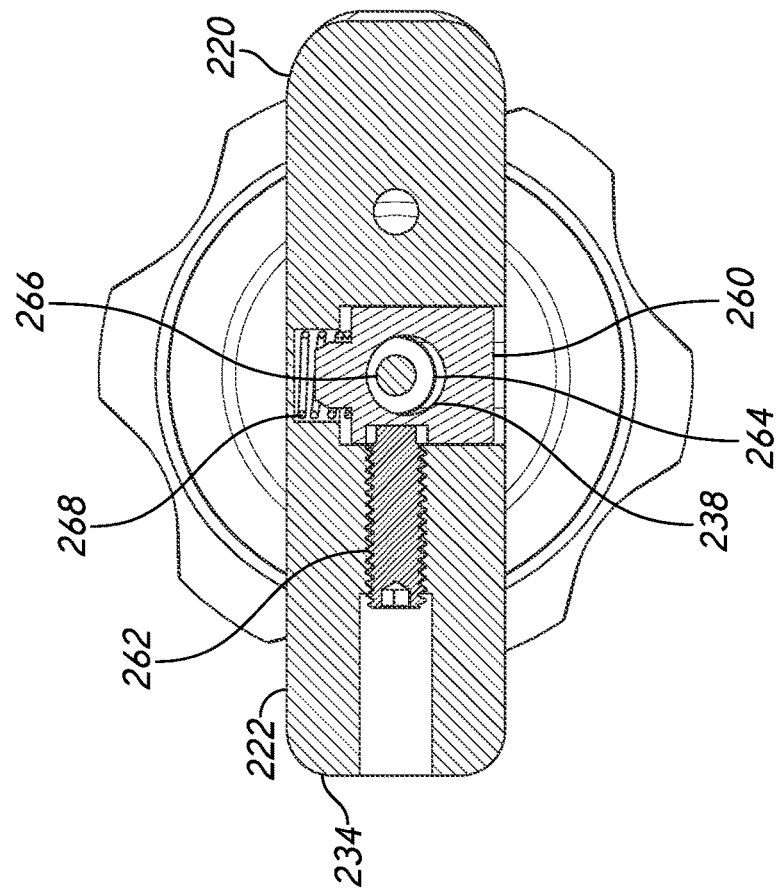
FIG. 13 is a cross-sectional view of a shaft lock of the trephine of FIG. 8.
Figure 12:
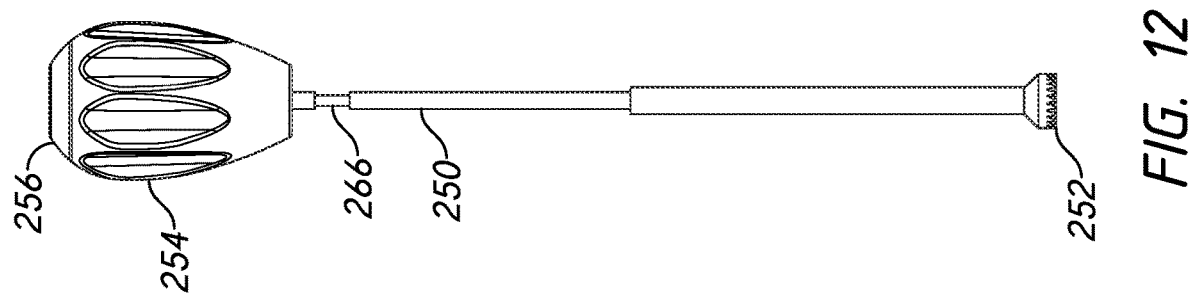
FIG. 12 is a front view of a trephine shaft of the trephine of FIG. 8.

FIGS. 6-13 depict views of components for positioning, targeting, access, and preparation. FIG. 6 illustrates a front view of a JAMSHIDI needle 200. FIG. 7 illustrates a front view of a k-wire 210. FIG. 8 illustrates a front view of a trephine 220. FIG. 9 illustrates a proximal view of the trephine 220. FIG. 10 illustrates a distal view of the trephine 220. FIG. 11 illustrates a perspective view of the trephine 220. FIG. 12 illustrates a front view of a trephine shaft 250. FIG. 13 illustrates a cross-sectional view of a shaft lock 260.

The JAMSHIDI needle 200 can include a cylindrical shape. The JAMSHIDI needle 200 can be hollow. The JAMSHIDI needle 200 can include a longitudinal lumen for receiving objects therethrough. The JAMSHIDI needle 200 can include a tip 202. The tip 202 can include a tapered cutting edge. The tip 202 can facilitate penetration of bone. The tip 202 can facilitate penetration of the pedicle in methods described herein. The JAMSHIDI needle 200 can include an inner trocar 204. The trocar 204 can be disposed within the longitudinal lumen. The trocar 204 can facilitate penetration of bone. The trocar 204 can facilitate penetration of the pedicle. The trocar 204 can prevent bone from entering the longitudinal lumen during penetration.

The JAMSHIDI needle 200 can include a handle 206. The JAMSHIDI handle 206 can be a T-handle. The JAMSHIDI handle 206 can be a two-piece design. The JAMSHIDI needle 200 can provide tactile feedback during insertion. The trocar 204 can be removed by proximal movement of the trocar 204 through the JAMSHIDI handle 206. The JAMSHIDI needle 200 can be positioned relative to the pedicle of the patient. The JAMSHIDI needle 200 can provide access to the pedicle for anchoring.

The k-wire 210 can be a thin metallic wire or pin. The k-wire 210 can include a tip 212. The tip 212 can be pointed or sharpened. The k-wire 210 can be drilled through bone. The k-wire 210 can be impacted into bone. The k-wire 210 can have a diameter of 0.9 mm, 1.0 mm, 1.1 mm, 1.2 mm, 1.3 mm, 1.4 mm, 1.5 mm, or any range of two of the foregoing values. The k-wire 210 can be sized to fit within the longitudinal lumen of the JAMSHIDI needle 200. The k-wire 210 can be passed through the JAMSHIDI needle 200 distally. The k-wire 210 can be advanced so that the tip 212 penetrates the pedicle of the patient. The JAMSHIDI needle 200 can facilitate placement of the k-wire 210 relative to the pedicle. The JAMSHIDI needle 200 can be removed once the k-wire is placed. The JAMSHIDI needle 200 can be removed by proximal movement of the JAMSHIDI needle 200 relative to the k-wire 210.

The trephine 220 can include a trephine handle 222. The trephine handle 222 can include finger grips 224. The finger grips 224 can facilitate holding or gripping the trephine handle 222. The trephine 220 can include a trephine body 226. The trephine handle 222 can be coupled to the trephine body 226. The trephine handle 222 and the trephine body 226 can be coupled with one or more fasteners. The trephine handle 222 can integrally formed with the trephine body 226. The trephine handle 222 and the trephine body 226 can comprise the same material. The trephine handle 222 and the trephine body 226 can comprise different materials. In some embodiments, the trephine body 226 comprises a more rigid material such as one or more metals and the trephine handle 222 comprises a more flexible material such as one or more polymers.

The trephine 220 can include a proximal end 228 and a distal end 230. The trephine 220 includes a length between the proximal end 228 and the distal end 230. The length can be along the direction of insertion of the trephine 220. The trephine handle 222 can include the proximal end 228. One or more components can extend past the trephine handle 222. The trephine body 226 can include the distal end 230.

The trephine 220 can include a first side 232 and a second side 234. The first side 232 can be near the thumb or palm of the user when the user grips the trephine 220. The second side 234 can be near the fingers of the user when the user grips the trephine 220. The trephine 220 can include a width extending between the first side 230 and the second side 232. The trephine 220 can include a width corresponding generally to the width of an incision. The trephine 220 can include a maximum width of 20 mm, 25 mm, 30 mm, 35 mm, 40 mm, 45 mm, 50 mm, or any range of two of the foregoing values.

The trephine 220 can include a thickness. The thickness can correspond to the transverse dimension near the first side 232. The thickness can correspond to the transverse dimension near the second side 234. The trephine 220 can include a maximum thickness of 2 mm, 3 mm, 4 mm, 5 mm, 6 mm, 7 mm, 8 mm, 9 mm, 10 mm, 11 mm, 12 mm, 13 mm, 14 mm, 15 mm, or any range of two of the foregoing values. The width can be greater than the thickness of the trephine 220.

The trephine 220 can be inserted over the k-wire 210. The trephine 220 can include a first lumen 236. The first lumen 236 can extend from the proximal end 228 to the distal end 230. The first lumen 236 can have a larger diameter near the proximal end 228. The first lumen 236 can have a smaller diameter near the distal end 230. The diameter of the first lumen near the distal end 230 can correspond to the diameter of the k-wire 210. The first lumen 236 can have a variable diameter. In other embodiments, the first lumen 236 can have a constant diameter.

The trephine 220 can include a second lumen 238. The second lumen 238 can extend from the proximal end 228 to the distal end 230. The second lumen 238 can have a constant diameter from the proximal end 228 to the distal end 230. In other embodiments, the second lumen 238 can have a variable diameter. The first lumen 236 can be positioned closer to the first side 232. The second lumen 238 can be positioned between the first side 232 and the second side 234. The second lumen 238 can be positioned at or near a midpoint between the first side 232 and the second side 234.

The trephine body 226 can be shaped to engage the anatomy of the patient. The trephine body 226 can include a guide 240. The guide 240 can include a diameter corresponding to the diameter of the JAMSHIDI needle 200. The guide 240 can fit within the cored hole formed by the JAMSHIDI needle 200. The guide 240 can include a smaller diameter than the cored hole formed by the JAMSHIDI needle 200. At least a portion of the guide 240 can be placed on top of the cored hole formed by the JAMSHIDI needle 200. At least a portion of the guide 240 can include a larger diameter than the cored hole formed by the JAMSHIDI needle 200. The guide 240 can include a stepped portion including a portion with a larger diameter and a portion with a smaller diameter. The first lumen 236 can extend through the guide 240. The guide 240 can facilitate positioning the trephine 220 relative to the k-wire 210. The guide 240 can facilitate positioning the trephine 220 relative to the cored hole formed by the JAMSHIDI needle 200.

The trephine body 226 can include a ledge 242. The ledge 242 can include a tapered end. The ledge 242 can be shaped to rest against the pedicle. The ledge 242 can be shaped to rest against the lamina. The ledge 242 can be shaped to engage the anatomy of the patient. The ledge 242 can be shaped to engage a generally horizontal surface of the pedicle and a generally slanted surface of the lamina. The ledge 242 can include a rounded edge. The ledge 242 can be atraumatic. The ledge 242 can stabilize the trephine 220 against the anatomy of the patient. The trephine body 226 can include a recess 244. The recess 244 can be positioned near the second lumen 238. The recess 244 can extend from the distal end 230. The trephine body 226 can include a shaped end for engaging the anatomy of the patient. The trephine body 226 can include a shaped end for positioning relative to the anatomy. The trephine body 226 can include a shaped end for accommodating one or more tools through the second lumen 238.

The trephine 220 can include a trephine shaft 250. The trephine shaft 250 can have two or more diameters along the length of the trephine shaft 250. In other embodiments, the trephine shaft 250 can have a constant diameter. The trephine shaft 250 can include a trephine blade 252. The trephine shaft 250 and the trephine blade 252 can be integrally formed. The trephine shaft 250 and the trephine blade 252 can be separately formed and coupled. The trephine blade 252 can be a cylindrical blade.

The recess 244 in the trephine body 226 can accommodate the trephine blade 252. The trephine blade 252 can have a smaller width than the trephine body 226. The trephine blade 252 can have a greater thickness than the trephine body 226. The trephine blade 252 can have a smaller thickness than the trephine body 226. The recess 244 can allow the trephine blade 252 to extend beyond the thickness of the trephine body 226. The trephine shaft 250 can extend through the trephine body 226. The trephine shaft 250 can extend through the second lumen 238. The trephine shaft 250 can be inserted from the distal end 230 into the second lumen 238. The trephine shaft 250 can be inserted to extend beyond the proximal end 228 of the trephine body 226. The trephine shaft 250 can extend through the trephine body 226. The trephine blade 252 can be disposed within the recess 244.

The trephine 220 can include a trephine shaft handle 254. The trephine shaft handle 254 can be removable. The trephine shaft 250 can be inserted into the trephine body 226 with the trephine shaft handle 254 detached. The trephine shaft handle 254 can be coupled to the trephine shaft 250 after insertion of the trephine shaft 250 through the trephine body 226. The trephine shaft handle 254 can include an impaction cap 256. The trephine shaft handle 254 can transmit force to the trephine shaft 250 to impact the trephine blade 252. The impaction cap 256 can be struck to seat the trephine blade 252.

The trephine shaft handle 254 can transmit torque to the trephine shaft 250 to rotate the trephine blade 252. The trephine shaft 250 can include a keyed shaft. The trephine shaft handle 254 can mate with the keyed shaft such that rotation of the trephine shaft handle 254 causes rotation of the trephine shaft 250. The trephine blade 252 can be configured to smooth a surface of a facet. The trephine blade 252 can reduce facet hypertrophy. The trephine blade 252 can reduce any enlargement of the facet due to degeneration or otherwise. The trephine blade 252 can be configured to alter the surface of the facet upon rotating the trephine shaft 250 clockwise and counterclockwise. The trephine blade 252 can be designed to bore or cut a surface of the facet. The trephine blade 252 can cut or bore a round surface. The trephine shaft handle 254 can rotate the trephine shaft 250. The user can repeatedly rotate the trephine shaft handle 254 approximately a quarter turn clockwise and then a quarter turn counterclockwise. The trephine shaft handle 254 can be rotated by hand. The trephine body 226 can include the ledge 242. The ledge 242 can seat against the anatomy of the patient as bone is removed by the trephine blade 252.

The trephine 220 can include a shaft lock 260. The shaft lock 260 can couple the trephine shaft 250 and the trephine body 226. The shaft lock 260 can prevent or limit longitudinal or axial movement of the trephine shaft 250 relative to the trephine body 226. The shaft lock 260 can allow rotational movement of the trephine shaft 250 relative to the trephine body 226. The trephine shaft 250 can be inserted into the trephine body 226 from the distal end 230. The trephine shaft 250 can extend into the second lumen 238 from the distal end 230. The trephine shaft 250 can be inserted to extend through the trephine body 226.

The trephine shaft 250 can be inserted into the trephine handle 222. The user can depress the shaft lock 260 relative to the trephine body 226. The shaft lock 260 can be depressed to allow the trephine shaft 250 to pass through the shaft lock 260. The trephine shaft 250 can be positioned such that the trephine blade 252 is within the recess 244. The trephine shaft 250 can freely slide within the second lumen 238 when the shaft lock 260 is depressed.

The shaft lock 260 can include a lock set screw 262. The lock set screw 262 can extend from the second side 234 of the trephine handle 222. The lock set screw 262 can retain the shaft lock 260 relative to the trephine handle 222. The lock set screw 262 can allow the shaft lock 260 to be depressed by a user. The shaft lock 260 can slide relative to the tip of lock set screw 262.

The shaft lock 260 can include a shaft lock lumen 264. The shaft lock lumen 264 can align with the second lumen 238 when the shaft lock 260 is depressed. The shaft lock lumen 264 and the second lumen 236 can be coaxial when the shaft lock 260 is depressed, as shown in FIG. 13. The trephine shaft 250 can include an engagement section 266. The engagement section 266 can include a smaller diameter than adjacent sections of the trephine shaft 250. The trephine shaft 250 can slide proximally until the engagement section 266 is disposed within the shaft lock lumen 264.

The shaft lock 260 can be released. The shaft lock 260 can be biased. The shaft lock 260 can include the spring 268. The shaft lock 260 can move transversely. The shaft lock 260 can slide relative to the lock set screw 262. The shaft lock 260 can slide relative to the trephine shaft 250. The engagement section 266 can be disposed with the shaft lock lumen 264. The shaft lock 260 can abut the engagement section 266. The spring 268 can bias the shaft lock 260 into contact with the engagement section 266 of the trephine shaft 250. The trephine shaft 250 can rotate relative to the shaft lock 260 when the shaft lock 260 is released. The shaft lock 260 can prevent or limit axial translation of the trephine shaft 250 relative to the trephine handle 222 when the shaft lock 260 is released. The shaft lock 260 can be biased against the trephine shaft 250 when the shaft lock 260 is released. The shaft lock lumen 264 can be offset from the second lumen 238 when the lock shaft lock 260 is released. The shaft lock 260 abuts the engagement section 266 of the trephine shaft 250.

The shaft lock 260 can provide tactile feedback that the trephine shaft 250 is locked. The trephine shaft 250 can be inserted into the trephine handle 222 and the trephine body 226 until the shaft lock 260 clicks into position. The shaft lock 260 clicks when the engagement section 266 of the trephine shaft 250 is within the shaft lock lumen 264 of the shaft lock 260. The trephine shaft handle 254 can engage the trephine shaft 250 after the trephine shaft 250 engages the shaft lock 260. The trephine shaft handle 254 can be rotated to remove bone, as described herein.

4. Access Preparation

Figure 14:
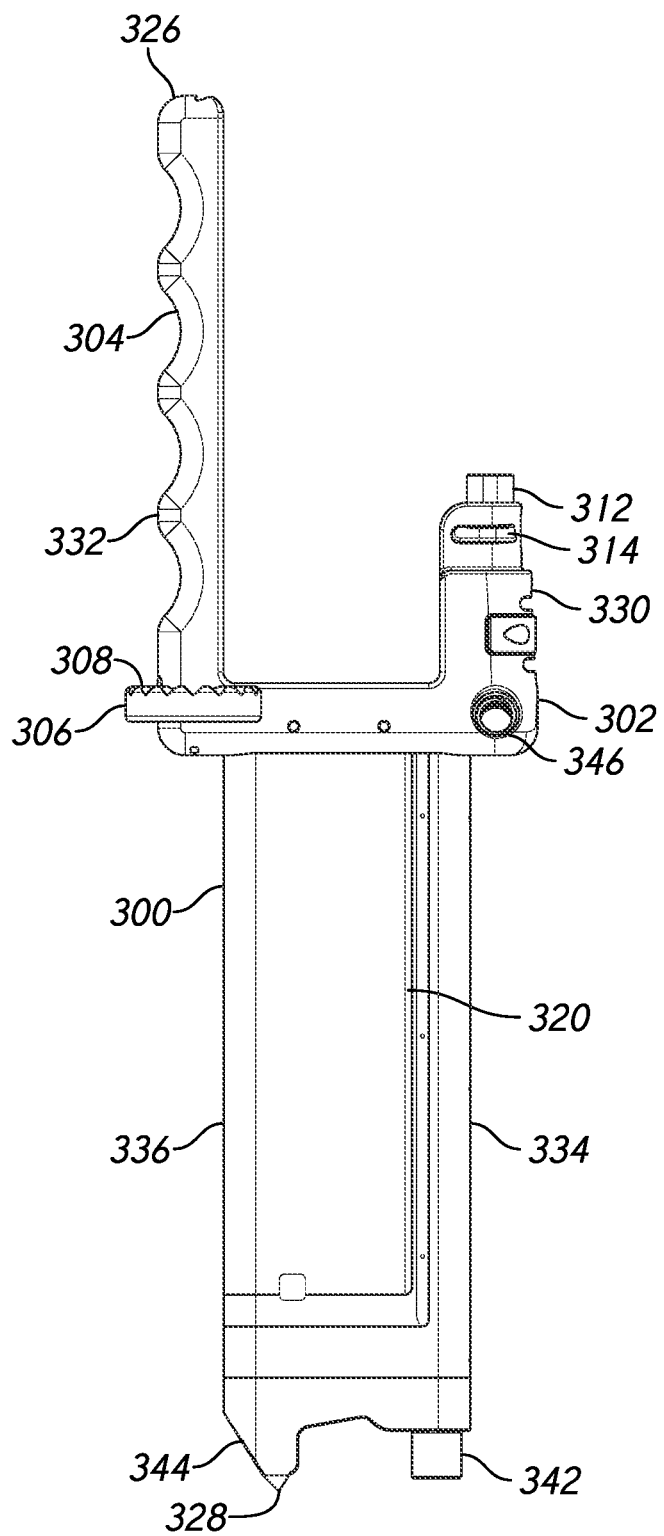
FIG. 14 is a front view of a portal.
Figure 16:
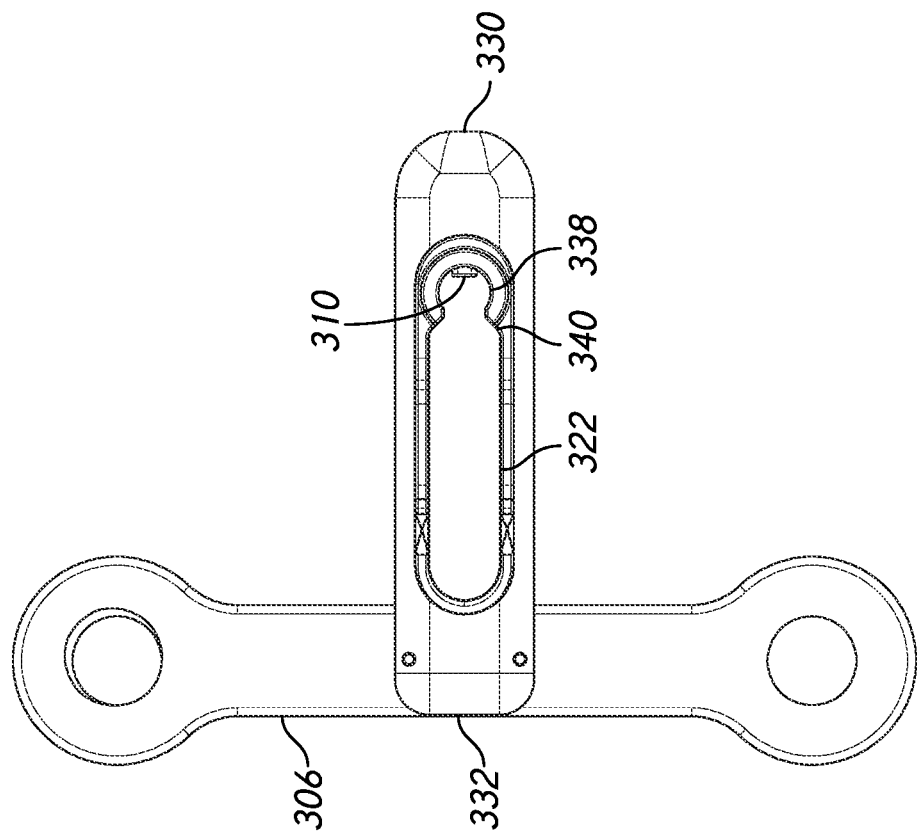
FIG. 16 is a distal view of the portal of FIG. 14.
Figure 15:
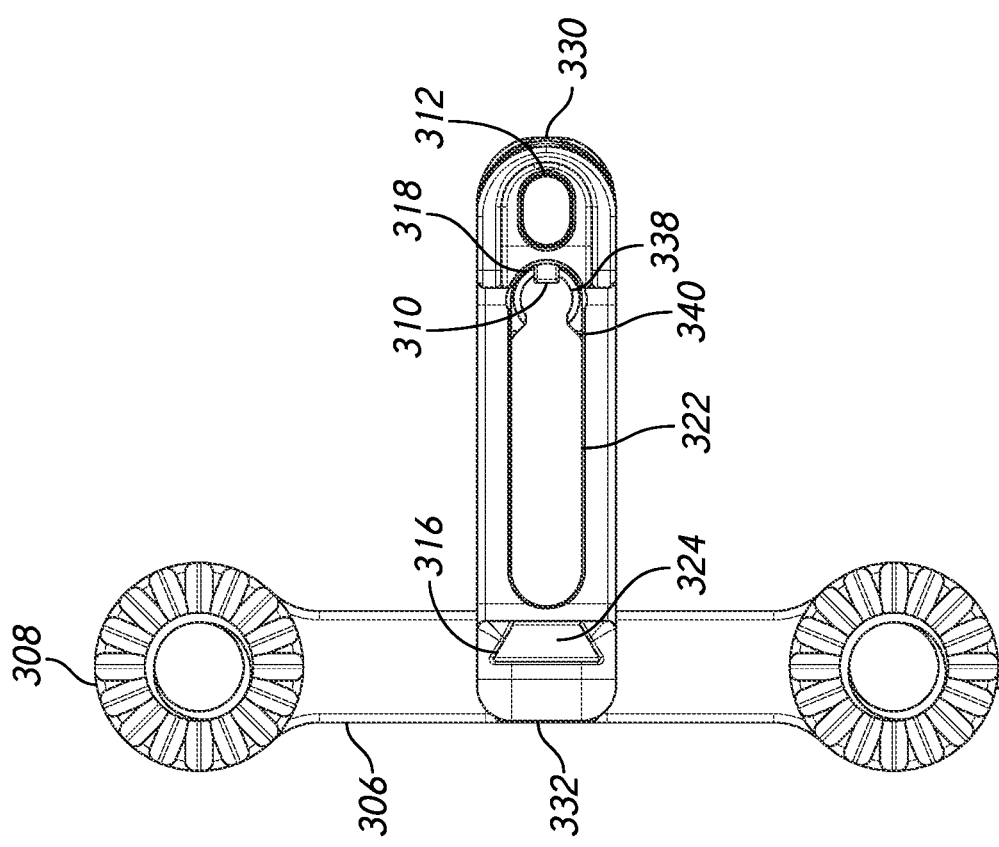
FIG. 15 is a proximal view of the portal of FIG. 14.
Figure 17:
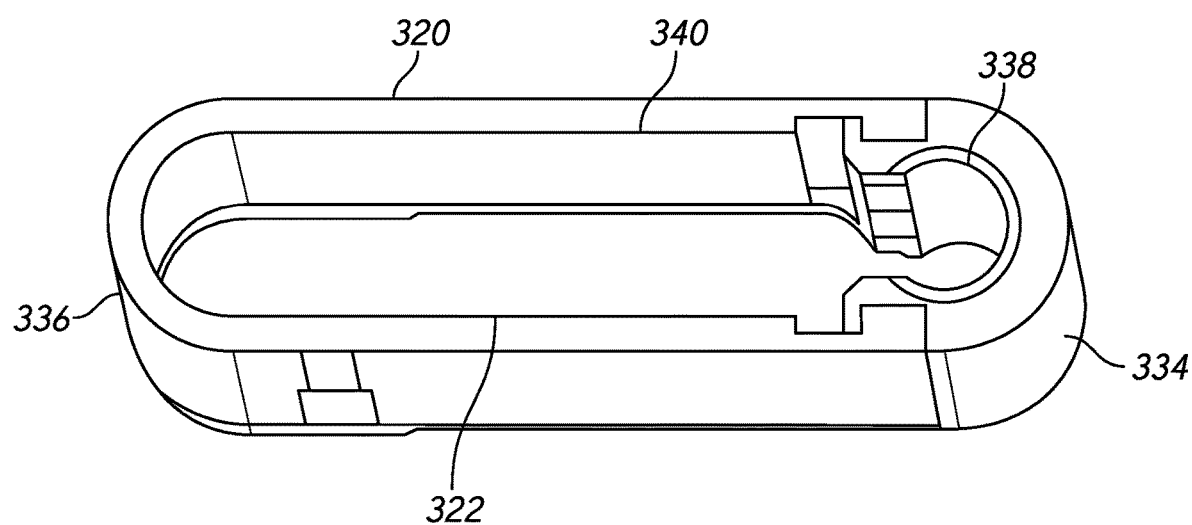
FIG. 17 is a cross-sectional view of the portal of FIG. 14.
Figure 18:
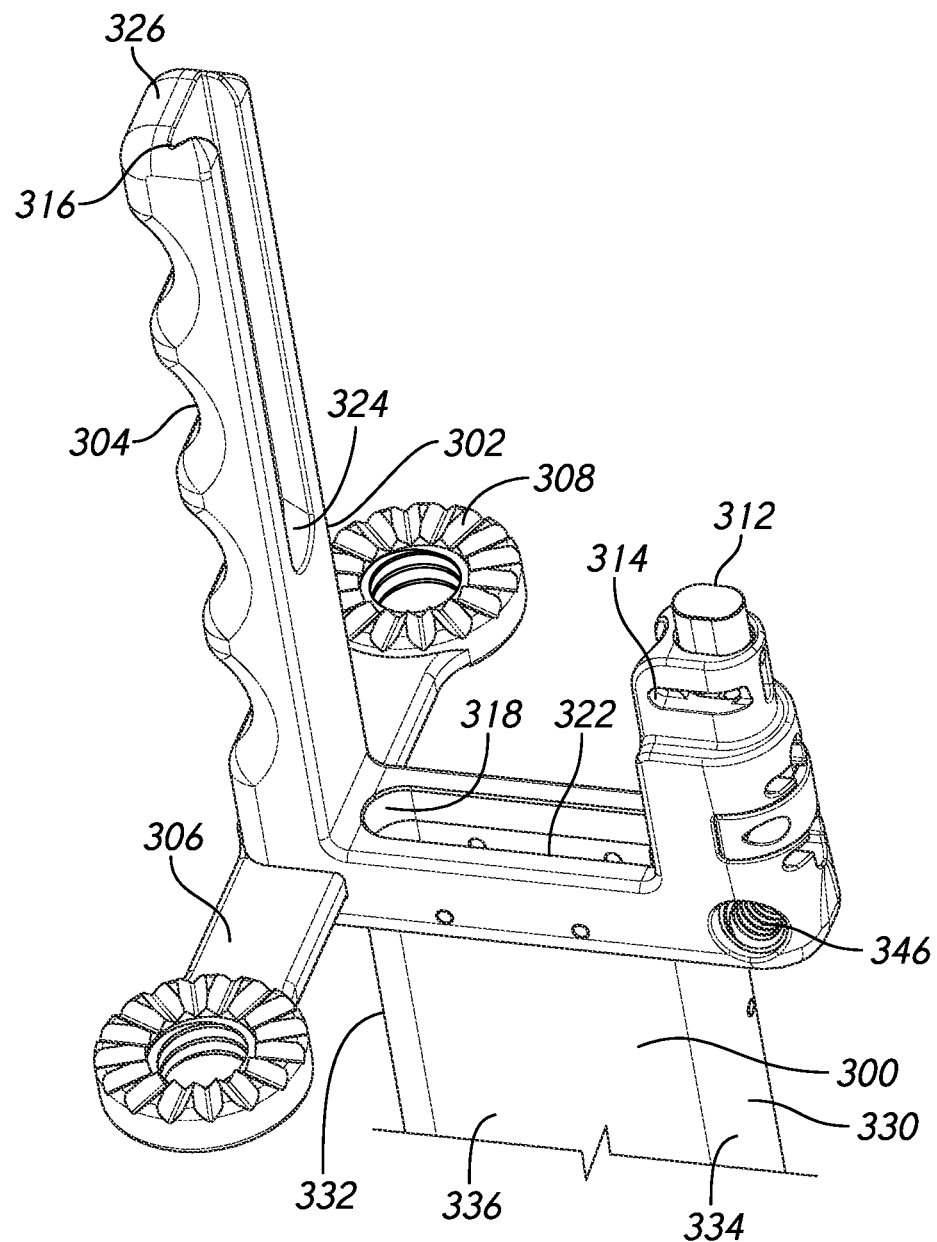
FIG. 18 is a perspective view of the portal of FIG. 14.
Figure 19:
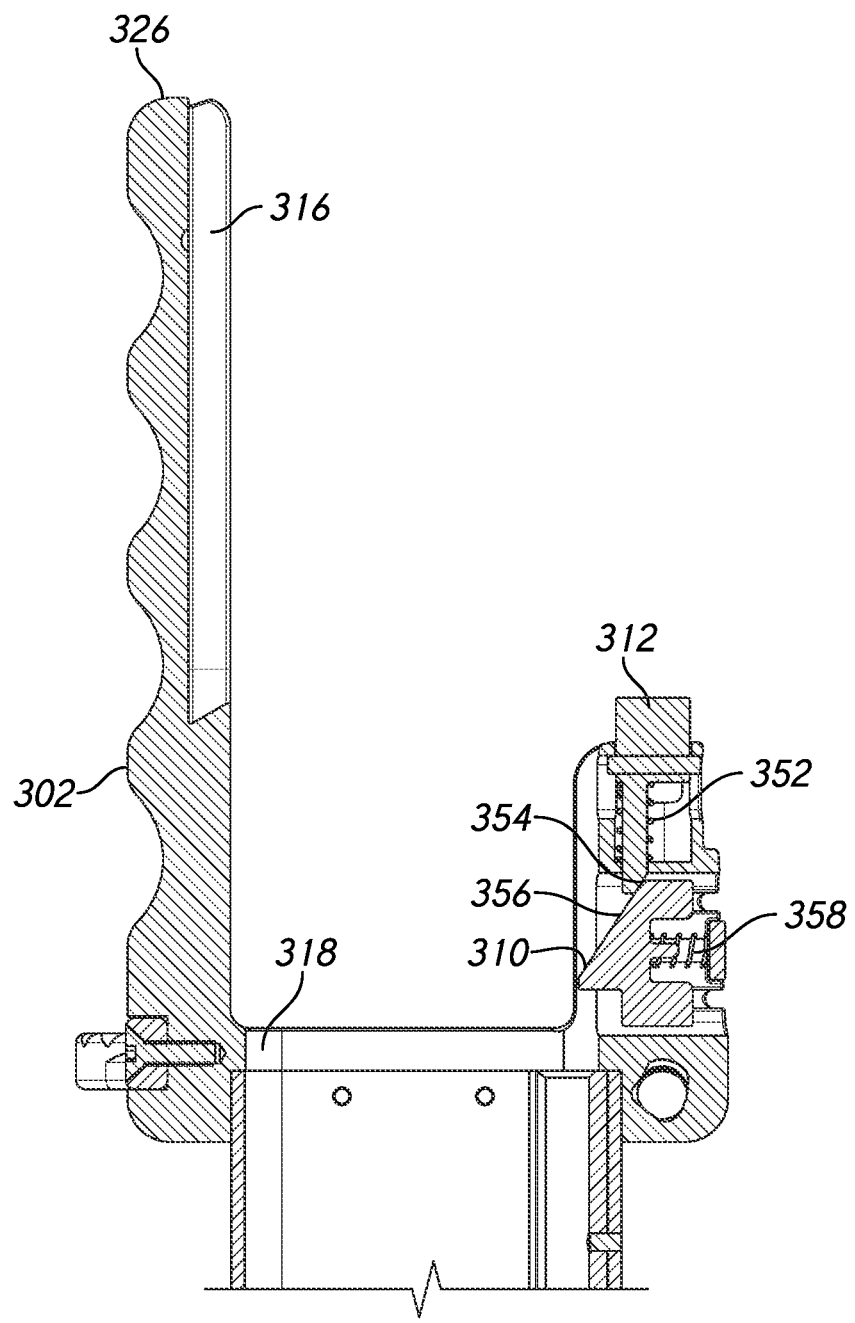
FIG. 19 is a cross-sectional view of the portal of FIG. 14.

FIGS. 14-19 depict views of components for access and anchoring. FIG. 14 illustrates a front view of a portal 300. FIG. 15 illustrates a proximal view of the portal 300. FIG. 16 illustrates a distal view of the portal 300. FIG. 17 illustrates a cross-sectional view of the portal 300. FIG. 18 illustrates a perspective view of the portal 300. FIG. 19 illustrates a cross-sectional view of the portal 300.

The portal 300 can include a portal handle 302. The portal handle 302 can include finger grips 304. The finger grips 304 can facilitate holding or gripping the portal handle 302.

The portal 300 can include an arm mount 306. The arm mount 306 can include one or more mount inserts 308. The arm mount 306 can include one mount insert, two mount inserts, three mount inserts, four mount inserts, or any range of two of the foregoing values. The mount inserts 308 can couple to the surgical arm for positioning and holding the portal 300. The surgical arm can hold the portal 300 in position relative to the anatomy of the patient. The arm mount 306 can include two mount inserts 308, as illustrated. The mount inserts 308 can provide alternative locations for mounting the surgical arm. The mount inserts 308 can be diametrically opposed relative to the portal handle 302. The portal 300 can be maintained in position by a single connection point. The surgical arm can connect to one of the two mount inserts 308. The mount inserts 308 can allow flexibility in positioning the surgical arm relative to the portal 300. The mount inserts 308 can be threaded. The mount inserts 308 can include splines. The mount inserts 308 can include features to limit or prevent movement between the portal 300 and the surgical arm. The arm mount 306 and the portal handle 302 can be separate components. The arm mount 306 and the portal handle 302 can be integrally formed.

The portal 300 can include a latch 310. The latch 310 can engage components relative to the portal handle 302. The latch 310 can couple to an awl, as described herein. The latch 310 can hold a component in a rotational orientation relative to the portal 300. The latch 310 can hold a component in a translational orientation relative to the portal 300. The latch 310 can ensure a fixed relationship between one or more components and the portal 300. The portal 300 can include a latch release button 312. The latch release button 312 can be depressed. The latch release button 312 can retract the latch 310 relative to the portal 300. The latch 310 can be biased. The latch 310 can be biased outward. The latch release button 312 can be depressed to disengage the latch 310. The latch release button 312 can be released to engage the latch 310. The latch 310 can be disposed relative to the portal handle 302. The latch 310 can move inward relative to the portal handle 302.

The portal handle 302 can include one or more alignment features 314. The portal handle 302 can include one alignment feature, two alignment features, three alignment features, four alignment features, or any range of two of the foregoing values. The alignment features 314 can be diametrically opposed. The alignment features 314 can be positioned under the latch release button 312. The alignment features 314 can include a groove. The alignment features 314 can be engaged by one or more corresponding alignment features, as described herein.

The portal handle 302 can include one or more sliding features 316. The portal handle 302 can include one sliding feature, two sliding features, three sliding features, four sliding features, or any range of two of the foregoing values. The sliding feature 316 can be a dovetail groove. The sliding feature 316 can include an undercut. The sliding feature 316 can be a shaped recess. The sliding feature 316 can include a stop 324. The stop 324 can be positioned at the distal end of the sliding feature 316. The sliding feature 316 can be positioned near the finger grips 304. The sliding feature 316 can be engaged by one or more corresponding sliding features, as described herein.

The portal handle 302 can include a lumen 318. The lumen 318 can be an elongate shape. The lumen 318 can be rounded. The lumen 318 can be oval. The lumen 318 can be any shape to allow the passage of one or more components as described herein. The lumen 318 can extend between the sliding feature 316 and the latch release button 312. The latch 310 can extend into the lumen 318.

The portal 300 can include a portal body 320. The portal handle 302 can be coupled to the portal body 320. The portal handle 302 and the portal body 320 can be coupled with one or more fasteners. The portal handle 302 can be integrally formed with the portal body 320. The portal handle 302 and the portal body 320 can comprise the same material. The portal handle 302 and the portal body 320 can comprise different materials.

The portal body 320 can include a lumen 322. The lumen 322 can be an elongate shape. The lumen 322 can be rounded. The lumen 322 can be oval. The lumen 322 can be any shape to allow the passage of one or more components as described herein. The lumen 318 of the portal handle 302 and the lumen 322 of the portal body 320 can be coaxial. The lumen 318 of the portal handle 302 and the lumen 322 of the portal body 320 can be generally aligned. The lumen 318 of the portal handle 302 and the lumen 322 of the portal body 320 can be similarly shaped. The lumen 322 of the portal body 320 can have two passageways, as described herein.

The portal 300 can include a proximal end 326 and a distal end 328. The portal 300 comprises a length between the proximal end 326 and the distal end 328. The length can be along the direction of insertion of the portal 300. The portal handle 302 can include the proximal end 326. The portal body 320 can include the distal end 328.

The portal 300 can include a first side 330 and a second side 332. The first side 330 can be near the thumb or palm of the user when the user grips the portal handle 302. The second side 332 can be near the fingers of the user when the user grips the portal handle 302. The portal 300 can include a width extending between the first side 330 and the second side 332. The portal 300 can include a width corresponding generally to the width of an incision. The portal 300 can include a maximum width of 20 mm, 25 mm, 30 mm, 35 mm, 40 mm, 45 mm, 50 mm, or any range of two of the foregoing values.

The portal 300 can include a thickness. The thickness can correspond to the transverse dimension near the first side 330. The thickness can correspond to the transverse dimension near the second side 332. The portal 300 can include a maximum thickness of 2 mm, 3 mm, 4 mm, 5 mm, 6 mm, 7 mm, 8 mm, 9 mm, 10 mm, 11 mm, 12 mm, 13 mm, 14 mm, 15 mm, or any range of two of the foregoing values. The width can be greater than the thickness of the portal 300.

The portal body 320 can include one or more sections. The portal body 320 can include a first section 334. The first section 334 can extend from the proximal end to the distal end of the portal body 320. The first section 334 can extend along the first side 330. The first section 334 can extend the along the distal end 328. The first section 334 can form a portal tip. The portal 300 can include a second section 336. The second section 336 can extend from the proximal end toward the distal end of the portal body 320. The second section 336 can extend along the second side 332. The first section 334 and the second section 336 can form the lumen 322 of the portal body 320. The first section 334 and the second section 336 can be formed of the same material. The first section 334 and the second section 336 can be formed from different materials. The first section 334 and the second section 336 can be integrally formed. The first section 334 and the second section 336 can be separately formed.

The lumen 322 can be irregularly shaped. The lumen 322 can include a first passageway 338. The first section 334 can form the first passageway 338. The first passageway 338 can form a circular arc. The circular arc can correspond to the diameter of an anchoring tool. The circular arc can correspond to the diameter of an awl, as described herein. The lumen 322 can include a second passageway 340. The second section 336 can form the second passageway 340. The second passageway 340 can be elongate. The second passageway 340 can be rounded. The second passageway 340 can be oval. The second passageway 340 can correspond to the cross-section of one or more components inserted into the portal 300. The lumens 318, 322 can extend from the proximal end 326 to the distal end 328. The first passageway 338 can be positioned closer to the first side 330. The second passageway 340 can be positioned between the first side 330 and the second side 332. The second passageway 340 can be positioned offset from a midpoint between the first side 330 and the second side 332. The second passageway 340 can be positioned closer to the second side 332 than the first side 330.

The portal body 320 can be shaped to engage the anatomy of the patient. The portal body 320 can include a guide 342. The guide 342 can include a diameter corresponding to the diameter of the JAMSHIDI needle 200. The guide 342 can fit within the cored hole formed by the JAMSHIDI needle 200. The guide 342 can facilitate positioning the portal body 320 relative to the k-wire 210. The guide 342 can facilitate positioning the portal body 320 relative to the cored hole formed by the JAMSHIDI needle 200. The first section 334 can form the guide 342.

The portal body 320 can include a ledge 344. The ledge 344 can include a tapered end. The ledge 344 can include a lamina spike. The ledge 344 can be shaped to rest against the pedicle. The ledge 344 can be shaped to rest against the lamina. The ledge 344 can be shaped to engage the anatomy of the patient. The ledge 344 can be shaped to engage a generally horizontal surface of the pedicle and a generally slanted surface of the lamina. The ledge 344 can include a sharpened edge. The ledge 344 can anchor the portal 300. The ledge 344 can stabilize the portal 300 against the anatomy of the patient. The portal body 320 can include a shaped end for anchoring to the anatomy of the patient. The portal body 320 can include a shaped end for engaging the anatomy.

The portal 300 can include one or more threaded openings 346. The portal handle 302 can include the threaded opening 346. The portal 300 can include one threaded opening, two threaded openings, three threaded openings, four threaded openings, or any range of two of the foregoing values. The threaded opening 346 can engage a positioning tool. The positioning tool can engage the threaded opening 346 to allow the user's hands to be away from the portal handle 302. The positioning tool can be an offset handle, described herein. The positioning tool can be threaded into the portal 300 to keep the hands of the user out of the shot for imaging.

The portal 300 can include the latch release button 312. The portal 300 can include a latch release button spring 352. The latch release button spring 352 can bias the latch release button 312 upward. The latch release button 312 can include a wedge 354 near the distal end of the latch release button 312. The wedge 354 of the latch release button 312 can slide relative to the latch 310 when the latch release button 312 is depressed or released. The latch 310 can include a corresponding wedge 356. As the wedge 354 of the latch release button 312 is depressed, the corresponding wedge 356 of the latch 310 moves. The portal 300 can include a latch spring 358. The latch spring 358 can bias the latch 310 inward. The latch release button spring 352 can be perpendicular to the latch spring 358.

The latch 310 can be in a neutral position as shown in FIG. 19. The latch release button 312 is biased upward by the latch release button spring 352. The wedge 354 of the latch release button 312 is at a proximal position. The latch 310 is at an inward position. The latch spring 358 is biasing the latch 310 inward. The latch 310 extends into the lumen 318 of the portal handle 302. The latch 310 extends over the first passageway 338. The corresponding wedge 356 of the latch 310 can be configured to engage an awl disposed within the first passageway 338, as described herein.

The latch release button 312 can be depressed. The latch release button 312 can compress the latch release button spring 352. The latch release button 312 can move distally. The wedge 354 of the latch release button 312 can move distally. The wedge 354 of the latch release button 312 can interact with the corresponding wedge 356 of the latch 310 to move the latch 310. The wedge 354 of the latch release button 312 can move the latch 310 outwardly when the latch release button 312 is depressed. The latch release button 312 can move the latch 310 outwardly. The wedge 354 of the latch release button 312 can slide relative to the corresponding wedge 356 of the latch 310. The wedge 354 of the latch release button 312 and the corresponding wedge 356 of the latch 310 can interact to retract the latch 310. The outward movement of the latch 310 can compress the latch spring 358. The latch 310 can retract into the portal handle 302. The latch 310 retracts relative to the first passageway 338. The latch release button 312 can be activated to retract the latch 310. The neutral position of the latch 310 can extend into the first passageway 338. The latch 310 can be biased by the latch spring 358. The corresponding wedge 356 of the latch 310 can be biased into engagement with tools in the first passageway 338. The latch release button 312 can be released to engage the latch 310 with tools in the first passageway 338. The latch 310 can move relative to the portal handle 302. The latch 310 can engage components to prevent rotation and translation of components relative to the portal 300.

5. Tissue Preparation

Figure 20:
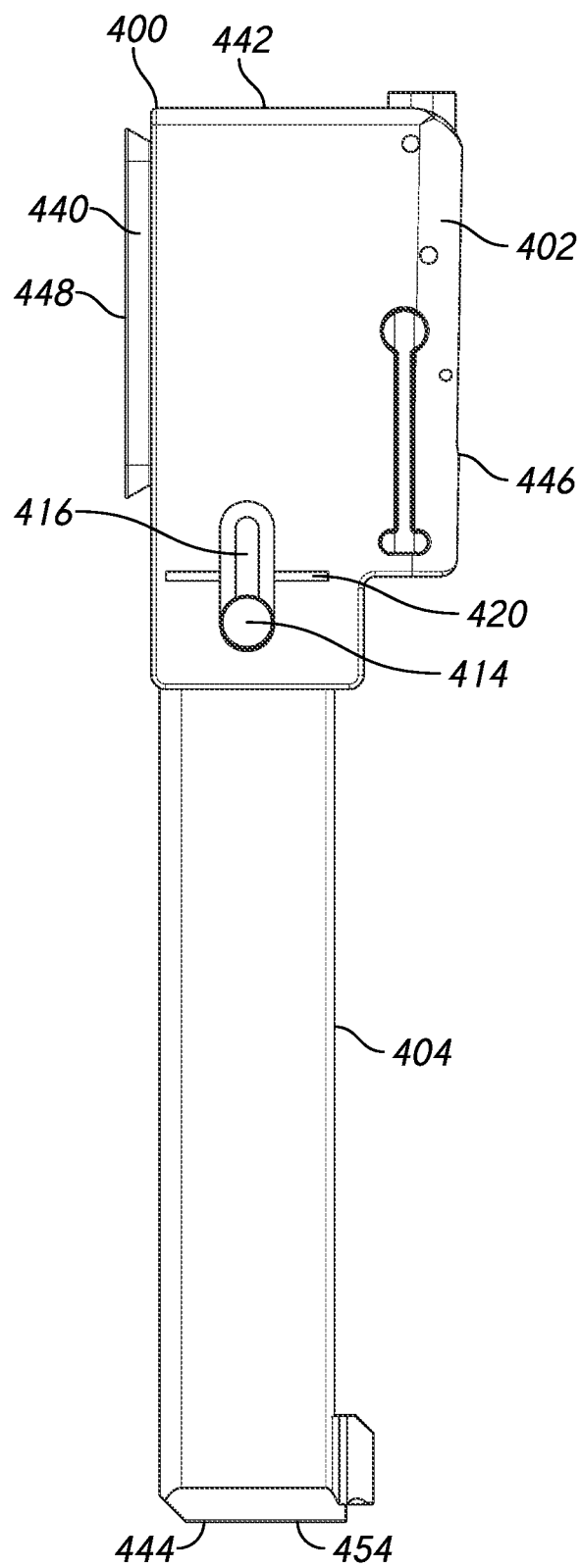
FIG. 20 is a front view of a tissue splitter.
Figure 21:
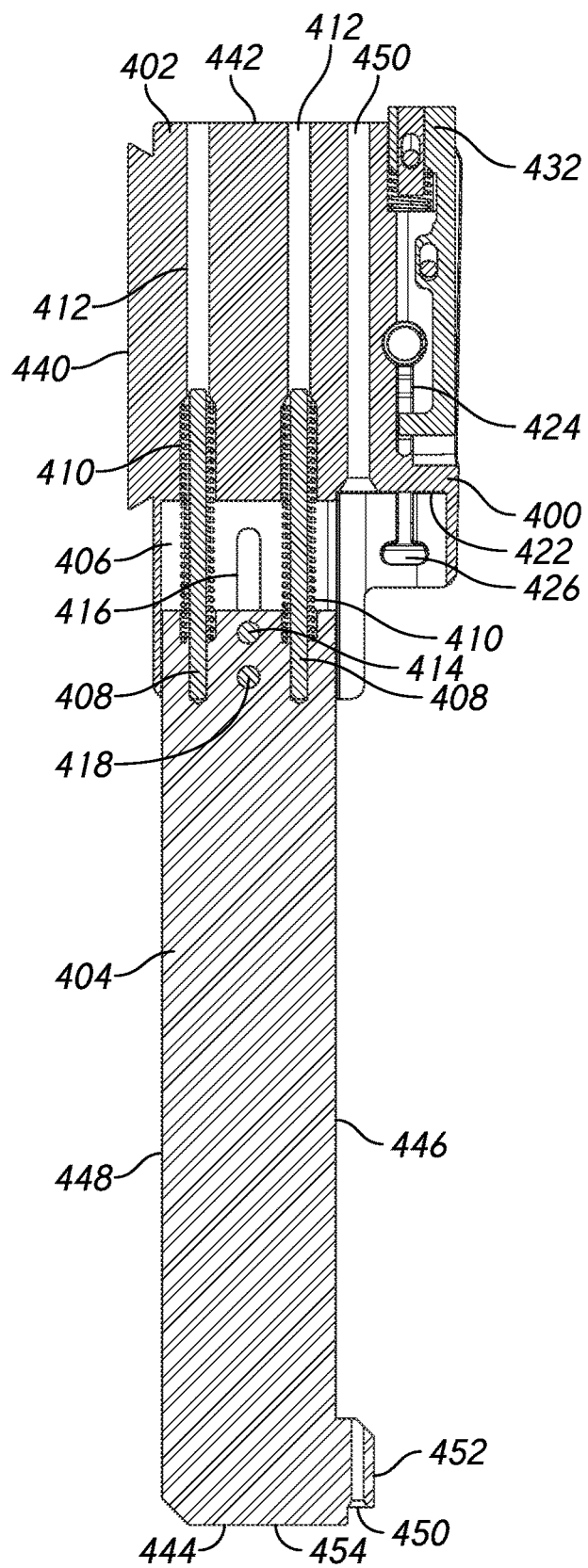
FIG. 21 is a cross-sectional view of the tissue splitter of FIG. 20.
Figure 22:
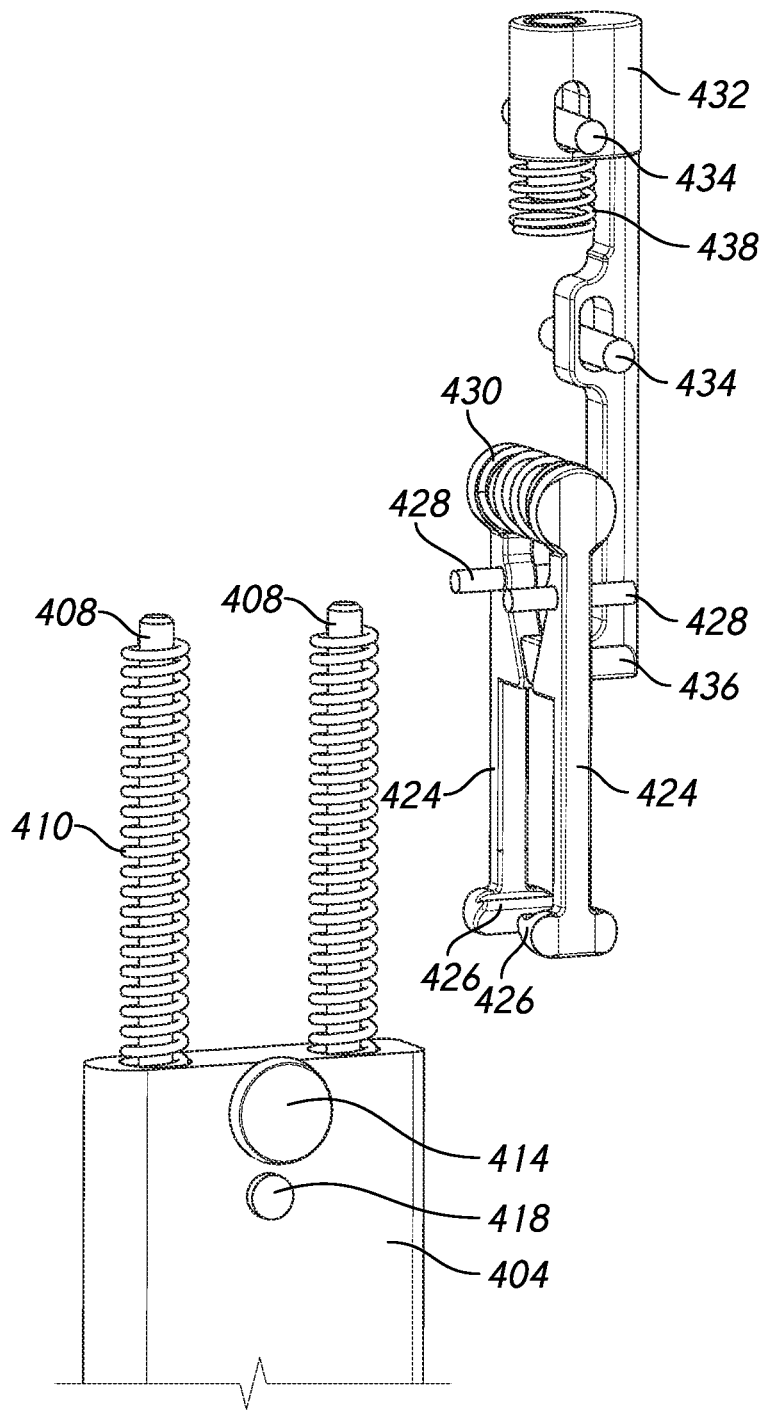
FIG. 22 is a view of internal components of the tissue splitter of Figure
Figure 23:
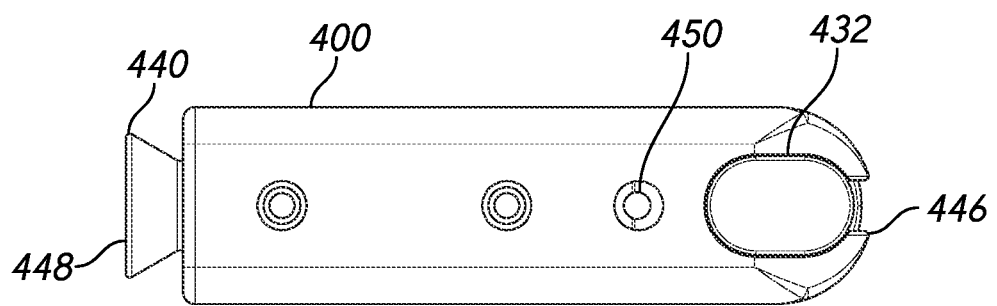
FIG. 23 is a proximal view of the tissue splitter of FIG. 20.
Figure 24:
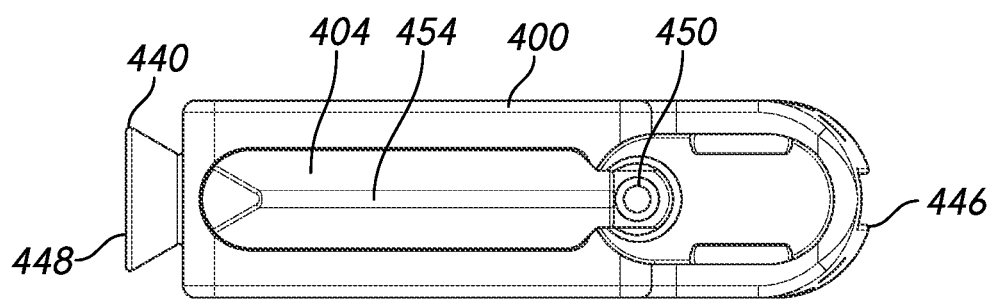
FIG. 24 is a distal view of the tissue splitter of FIG. 20.
Figure 25:
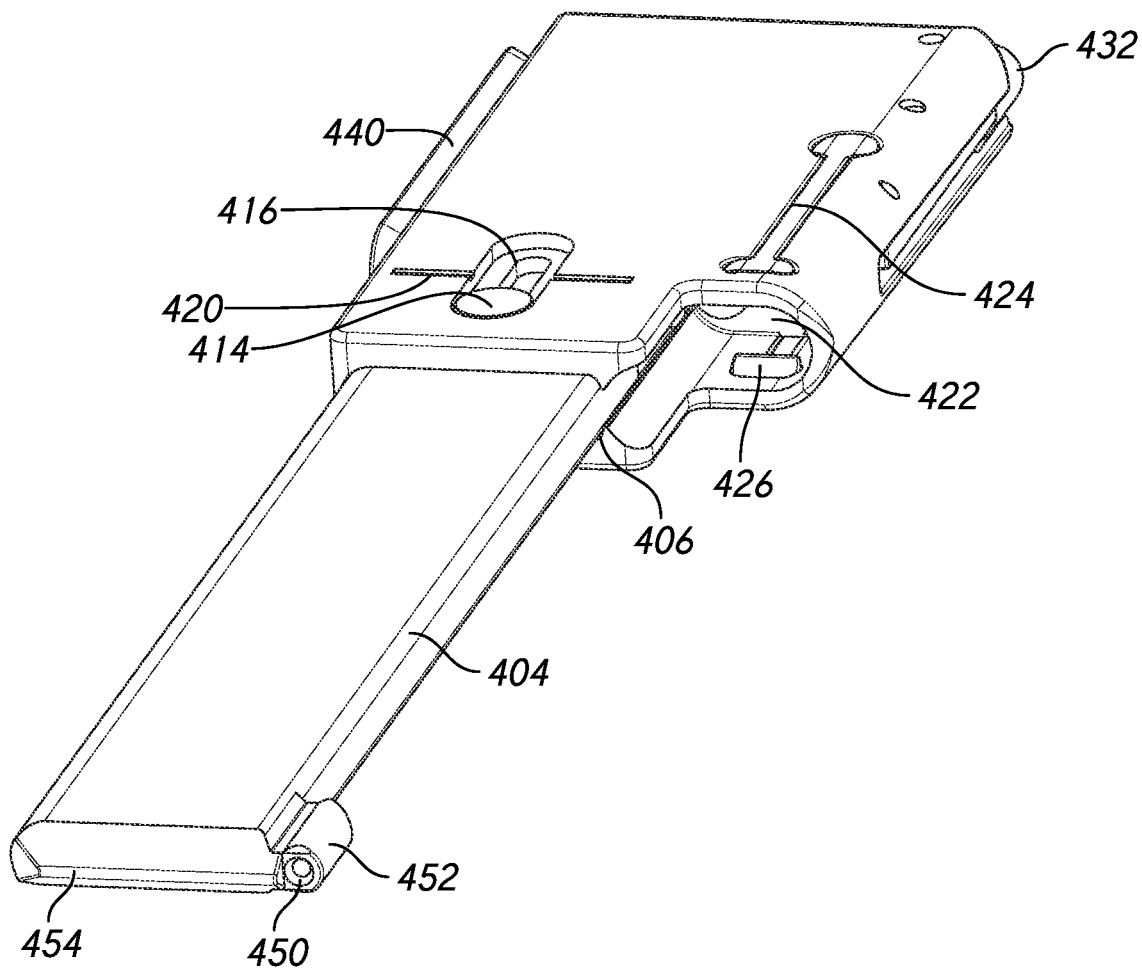
FIG. 25 is a perspective view of the tissue splitter of FIG. 20.

FIGS. 20-25 depict views of components for tissue separation. FIG. 20 illustrates a front view of a tissue splitter 400. FIG. 21 illustrates a cross-sectional view of the tissue splitter 400. FIG. 22 illustrates a view of internal components of the tissue splitter 400. FIG. 23 illustrates a proximal view of the tissue splitter 400. FIG. 24 illustrates a distal view of the tissue splitter 400. FIG. 25 illustrates a perspective view of the tissue splitter 400.

The tissue splitter 400 can include a tissue splitter handle 402. The tissue splitter handle 402 can include surfaces allowing a user to grip the tissue splitter 400. The tissue splitter 400 can include a blade 404. The tissue splitter handle 402 can be coupled to the blade 404. The tissue splitter handle 402 and the blade 404 can allow sliding between the tissue splitter handle 402 and the blade 404. The tissue splitter handle 402 and the blade 404 can comprise the same material. The tissue splitter handle 402 and the blade 404 can comprise different materials. In some embodiments, the blade 404 comprises a more rigid material such as one or more metals and the tissue splitter handle 402 comprises a more flexible material such as one or more polymers.

The tissue splitter handle 402 can include a cavity 406. The cavity 406 can extend from the distal end of the tissue splitter handle 402. The cavity 406 can extend along a portion of the length of the splitter handle 402 such as 10% of the length, 15% of the length, 20% of the length, 25% of the length, 30% of the length, 35% of the length, 40% of the length, 45% of the length, 50% of the length, or any range of two of the foregoing values. The blade 404 can be disposed within the cavity 406 of the tissue splitter handle 402.

The tissue splitter 400 can include one or more pins 408. The tissue splitter 400 can include two pins 408. The one or more pins 408 can extend between the tissue splitter handle 402 and the blade 404. The tissue splitter 400 can include one or more springs 410. The tissue splitter 400 can include two springs 410. The one or more springs 410 can extend between the tissue splitter handle 402 and the blade 404. The tissue splitter 400 can include two pins 408 and two springs 410. Each pin 408 can have an associated spring 410. The one or more pins 408 and the one or more springs 410 can function as a suspension system. The tissue splitter 400 can include one or more channels 412. The tissue splitter 400 can include two channels 412. The one or more channels 412 can extend between the tissue splitter handle 402 and the blade 404. Each pin 408 can be disposed within a corresponding channel 412.

The blade 404 can slide upward within the cavity 406. As the blade 404 slides upward, the one or more pins 408 slide upward within the one or more channels 412. The one or more pins 408 are pushed by the blade 404. The one or more pins 408 can be separately formed from the blade 404. The one or more pins 408 and the blade 404 can be integrally formed. As the blade 404 slides upward, the one or more springs 410 can be compressed. The one or more springs 410 can bias the blade 404 downward. The blade 404 is configured to split tissue. The blade 404 is configured to bottom out on the vertebrae. The bone applies a counteracting force on the blade 404. The bone pushes the blade 404 upward into the cavity 406 of the tissue splitter handle 402 as the blade 404 is advanced through tissue and into contact with bone.

The blade 404 can include an indicator 414. The indicator 414 can be separately formed from the blade 404. The indicator 414 can be separately formed from the tissue splitter handle 402. The tissue splitter handle 402 can include an indicator channel 416. The indicator 414 can be disposed within the indicator channel 416. The indicator 414 can couple the blade 404 and the tissue splitter handle 402. The indicator 414 can allow limited sliding movement between the blade 404 and the tissue splitter handle 402. As the blade 404 slides upward, the indicator 414 slides upward within the indicator channel 416. The blade 404 can include an alignment pin 418. The alignment pin 418 can be disposed within the indicator channel 416. The indicator 414 and the alignment pin 418 can allow sliding between the blade 404 and the tissue splitter handle 402. The indicator 414 and the alignment pin 418 can limit or prevent rotation between the blade 404 and the tissue splitter handle 402.

The tissue splitter handle 402 can include a marking 420. The marking 420 can be a line. The marking 420 can provide a visual cue to the user of the position of the blade 404 relative to the tissue splitter handle 402. The marking 420 can provide a visual cue to the user of the position of the blade 404 relative to the portal 300. The marking 420 can be a depth marking. The indicator 414 can align with the marking 420 when the blade 404 has moved a predetermined distance. The indicator 414 can align with the marking 420 when the blade 404 is retracted within the cavity 406. The indicator 414 can align with the marking 420 when the blade 404 has moved a predetermined distance based on the anatomy of the patient. The indicator 414 can align with the marking 420, or extend below the marking 420, or extend above the marking 420. The marking 420 can indicate a distance between the portal 300 and the tip 454 when the tip 454 engages the anatomy. The marking 420 can indicate the minimal distance needed for lumen formation between the portal 300 seated against the anatomy and the tip 454 seated against the anatomy. The marking 420 can indicate the depth of bone needed to form the bone lumen. The marking 420 can indicate relative positioning between a maximum point of the anatomy and the portal 300.

The tissue splitter handle 402 can include a latch cavity 422. The latch cavity 422 can extend from the distal end of the tissue splitter handle 402. The tissue splitter handle 402 can receive the latch release button 312 of the portal 300 within the latch cavity 422. The latch cavity 422 can have clearance for the latch release button 312. The latch release button 312 can be in a neutral position when received by the latch cavity 422. The latch release button 312 can be biased upward when received by the latch cavity 422. The latch 310 can be biased inward relative to the portal handle 300 when the tissue splitter handle 302 is coupled to the portal handle 302.

The tissue splitter handle 402 can include one or more latch arms 424. The tissue splitter handle 402 can include two latch arms 424. The latch arms 424 can be diametrically opposed. Each latch arm 424 can include a corresponding alignment feature 426. The corresponding alignment feature 426 can be a projection. The portal handle 302 can include one or more alignment features 314. The alignment feature 314 can be a groove. Each alignment feature 314 can be engaged by the corresponding alignment feature 426 to lock the portal 300 and the tissue splitter 400.

FIG. 22 illustrates the tissue splitter 400 with the tissue splitter handle 402 removed. The one or more latch arms 424 can be configured to pivot. The tissue splitter 400 can include pivot pins 428. Each latch arm 424 can be mounted on the corresponding pivot pin 428. The latch arm 424 can pivot relative to the pivot pin 428 to engage or disengage the corresponding alignment feature 426 of the latch arm 424 with the alignment feature 314 of the portal 300. The tissue splitter 400 can include a spring 430. The spring 430 can bias the corresponding alignment feature 426 of the latch arm 424 into engagement with the alignment feature 314. The spring 430 can bias both latch arms 424. The spring 430 can bias the corresponding alignment features 426 of the two latch arms 424 into engagement with the alignment features 314.

The tissue splitter 400 can include a latch arm button 432. The latch arm button 432 can include one or more alignment pins 434. The alignment pins 434 can guide movement of the latch arm button 432 in a proximal-distal direction. The latch arm button 432 can include a wedge 436. The wedge 436 can be disposed between the latch arms 424. The latch arm button 432 can include a spring 438. The spring 438 can bias the latch arm button 432 in the proximal direction. The latch arm button 432 can be biased upward. The latch arm button 432 can be biased to disengage the wedge 436 from the one or more latch arms 424. The latch arm button 432 can be depressed. As the latch arm button 432 is depressed, the wedge 436 can interact with the latch arm 424. As the latch arm button 432 is depressed, the wedge 436 can pivot the one or more latch arms 424 relative to the corresponding pivot pin 428. The wedge 436 can pivot the one or more latch arms 424 outward. As the latch arm button 432 is depressed, the corresponding alignment feature 426 of the latch arm 424 can disengage the alignment feature 314 of the portal 300.

The tissue splitter 400 can include one or more corresponding sliding features 440. The tissue splitter handle 402 can include the corresponding sliding features 440. The tissue splitter 400 can include one corresponding sliding feature, two corresponding sliding features, three corresponding sliding features, four corresponding sliding features, or any range of two of the foregoing values. The corresponding sliding feature 440 can be a dovetail projection. The corresponding sliding feature 440 can be a tapered projection. The corresponding sliding feature 440 can be configured to interlock with the sliding feature 316 of the portal 300. The sliding feature 316 of the portal 300 can be engaged by the corresponding sliding feature 440 of the tissue splitter 400. The sliding feature 316 and the corresponding sliding feature 440 can have a corresponding shape to allow sliding. The sliding feature 316 and the corresponding sliding feature 440 can have a corresponding shape to prevent or limit rotation. The corresponding sliding feature 440 can slide relative to the portal 300 until the corresponding sliding feature 440 reaches the stop 324 of the portal 300.

The tissue splitter 400 can include a proximal end 442 and a distal end 444. The tissue splitter 400 can include a length between the proximal end 442 and the distal end 444. The length can be along the direction of insertion of the tissue splitter 400. The proximal end 442 can include the tissue splitter handle 402. The distal end 444 can include the blade 404.

The tissue splitter 400 can include a first side 446 and a second side 448. The tissue splitter 400 can include a width extending between the first side 446 and the second side 448. The tissue splitter 400 can include a maximum width of 20 mm, 25 mm, 30 mm, 35 mm, 40 mm, 45 mm, 50 mm, or any range of two of the foregoing values. The tissue splitter 400 can include a thickness. The thickness can correspond to the transverse dimension of the width. The thickness can correspond to the transverse dimension of the first side 446. The thickness can correspond to the transverse dimension of the second side 448. The tissue splitter 400 can include a maximum thickness of 2 mm, 3 mm, 4 mm, 5 mm, 6 mm, 7 mm, 8 mm, 9 mm, 10 mm, 11 mm, 12 mm, 13 mm, 14 mm, 15 mm, or any range of two of the foregoing values. The width can be greater than the thickness of tissue splitter 400. The width and thickness of the tissue splitter 400 can correspond to the width and thickness of the lumen 318 of the portal handle 302. The width and thickness of the blade 404 can correspond to the width and thickness of the lumen 322 of the portal body 320.

The tissue splitter 400 can be inserted over the k-wire 210. The tissue splitter 400 can include a first lumen 450. The first lumen 450 can extend from the proximal end 442 to the distal end 444. The first lumen 450 can have a larger diameter near the proximal end 442. The first lumen 450 can have a smaller diameter near the distal end 444. The diameter of the first lumen 450 near the distal end 444 can correspond to the diameter of the k-wire 210. The first lumen 450 can be positioned closer to the first side 446.

The blade 404 can include an alignment guide 452 to engage the portal body 320. The portal body 320 can include the lumen 322. The portal body 320 can include one or more sections. The portal body 320 can include the first section 334. The first section 334 can extend along the first side 330. The first section 334 can form the first passageway 338. The first passageway 338 can form a circular arc. The alignment guide 452 can slide along the first section 334 of the portal body 320. The alignment guide 452 can slide within the first passageway 338 of the portal body 320. The alignment guide 452 and the first section 334 can have a corresponding shape to allow sliding. The alignment guide 452 and the first section 334 can have a corresponding shape to prevent or limit rotation. The alignment guide 452 can include the first lumen 450. The alignment guide 452 can facilitate sliding of the tissue splitter 400 relative to the k-wire 210. The portal body 320 can include the second section 336. The second section 336 can extend along the second side 332. The second section 336 can form the second passageway 340. The blade 404 can slide within the second passageway 340.

The blade 404 can include a tip 454. The tip 454 can be rounded. The tip 454 can be blunt. In other embodiments, the tip 454 can be sharpened. The tip 454 can form a wedge. The tip 454 can have a shape to split tissue. The tip 454 can be configured to penetrate to the bone.

The tissue splitter 400 can be inserted into the portal 300. The tissue splitter 400 can slide from the proximal end 326 of the portal 300. The blade 404 can be inserted into the lumen 318 of the portal handle 302. The blade 404 can be inserted into the lumen 322 of the portal body 320. The alignment guide 452 of the tissue splitter 400 can extend along the first side 330 of the portal 300. The alignment guide 452 can slide within the first passageway 338 of the portal body 320. The blade 404 can slide within the second passageway 340 of the portal body 320. The corresponding sliding features 440 of the tissue splitter 400 can engage the sliding feature 316 of the portal 300. The corresponding sliding features 440 of the tissue splitter 400 can slide relative to the sliding feature 316 of the portal 300. The corresponding sliding features 440 of the tissue splitter 400 can abut the stop 324 of the portal 300.

The tissue splitter 400 can lock into place relative to the portal 300. The corresponding alignment feature 426 of the latch arm 424 can be pivoted outward. The portal handle 302 near the latch release button 312 can interact with the latch arms 424. The portal handle 302 can slide into the latch cavity 422 of the tissue splitter. The portal handle 302 can pivot the latch arms 424. The spring 430 can bias the latch arms 424 of the tissue splitter 400 inward. The spring 430 can bias the corresponding alignment feature 426 of latch arms 424 into engagement with the alignment feature 314 of the portal 300. The corresponding alignment feature 426 of latch arms 424 can lock the tissue splitter 400 to the portal 300. The portal 300 can be fixed relative to the tissue splitter handle 402. The blade 404 can slide relative to the portal 300 and the tissue splitter handle 402. The position of the blade 404 relative to the portal 300 and the tissue splitter handle 402 can be determined by the indicator 414. The blade 404 can slide in the proximal-distal direction along the one or more pins 408.

The tissue splitter 400 and portal 300 can slide over the k-wire 210. The k-wire 210 can extend through the first lumen 450 of the tissue splitter 400. The blade 404 can extend past the distal end 328 of the portal 300 when the tissue splitter 300 engages the portal 300. The blade 404 can engage tissue. The tip 454 of the blade 404 can engage tissue as the tissue splitter 400 and portal 300 are advanced. The blade 404 can extend through tissue to the lamina. The blade 404 can contact the lamina.

The tissue splitter 400 and portal 300 can be further advanced to seat the portal 300. The blade 404 can be retracted into the tissue splitter handle 402 as the portal 300 is further advanced. The position of the blade 404 relative to the portal 300 and the tissue splitter handle 402 can be shown by the indicator 414. The indicator 414 moves relative to the marking 420 as the tissue splitter 400 and the portal 300 are seated. The indicator 414 can align with the marking 420 when the blade 404 is retracted a minimal distance to form the bone lumen. The indicator 414 can align with the marking 420 or extend above the marking 420 when the portal 300 is fully seated. The blade 404 retracts into the cavity 406 relative to the tissue splitter handle 402 and the portal 300. The marking 420 can indicate the position of the portal 300 relative to the bone when the blade 404 contacts the bone. The marking 420 can be a depth indicator. The blade 404 retracts to allow the portal 300 to seat against the pedicle and the lamina. As the portal 300 is placed, the indicator 414 moves relative to the marking 420. The indicator 414 can align with the marking 420 when the blade 404 retracts a sufficient distance to allow a bone lumen to be formed. The tissue splitter 400 can be removed, leaving the portal 300 in place relative to the k-wire 210.

6. Anchoring Preparation

Figure 26:
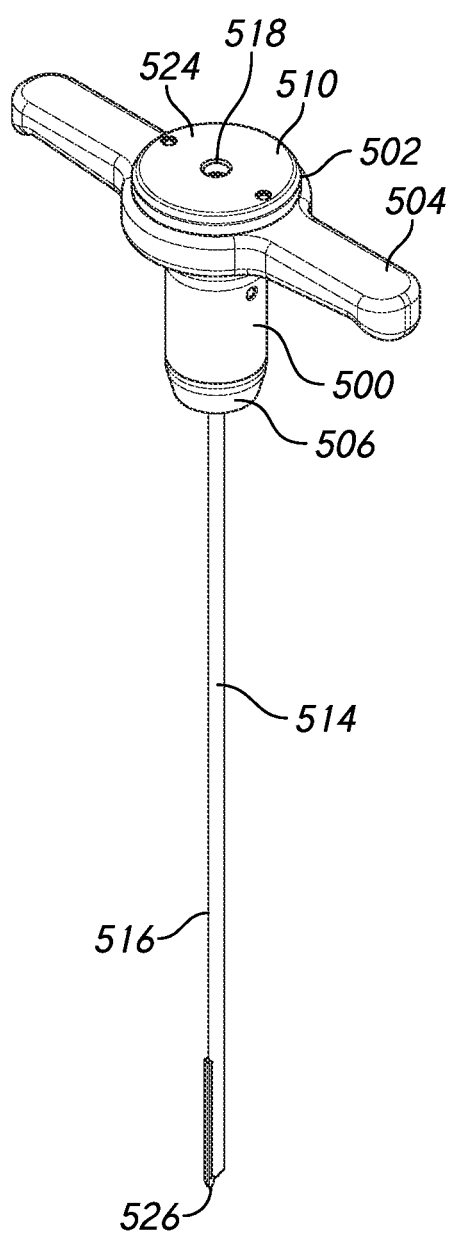
FIG. 26 is a perspective view of an awl handle.
Figure 27:
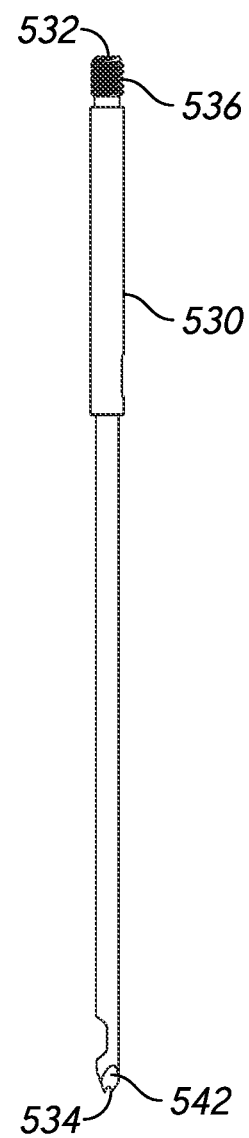
FIG. 27 is a side view of an awl.
Figure 28:
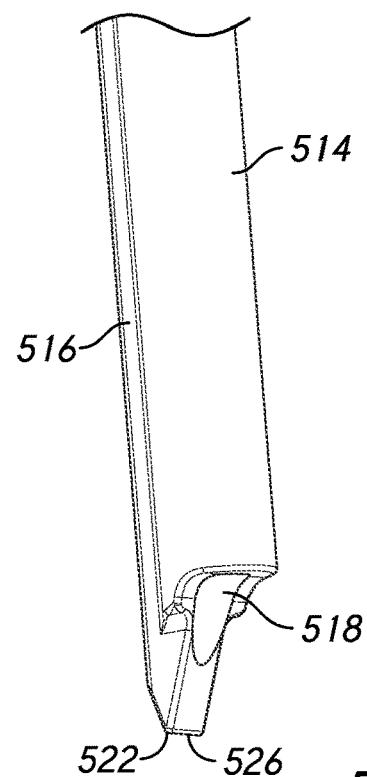
FIG. 28 is a side view of a tip of the awl handle of FIG. 26.
Figure 29:
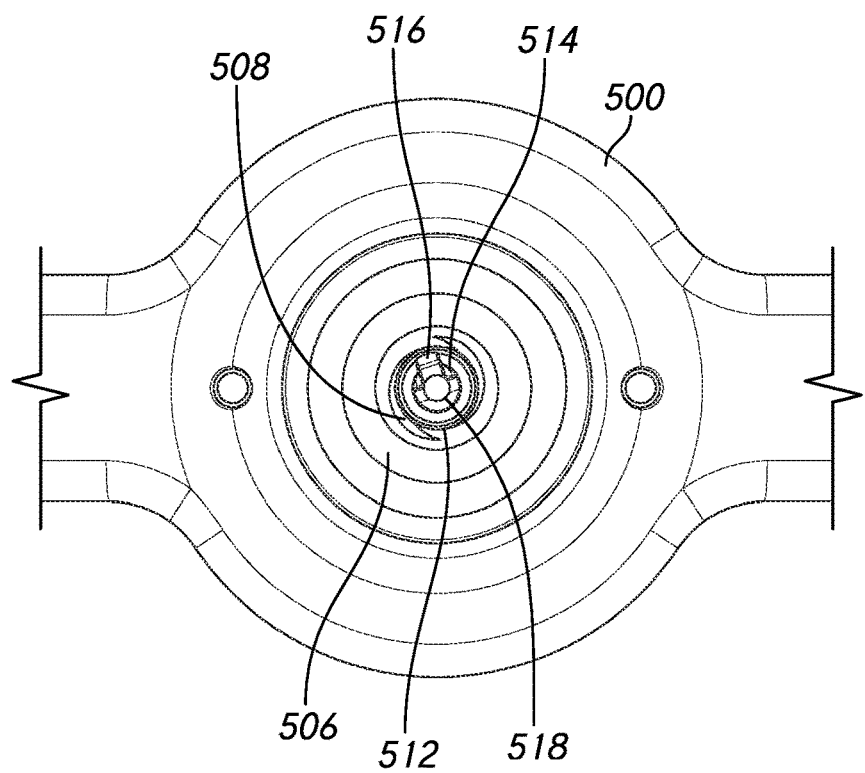
FIG. 29 is a distal view of the awl handle of FIG. 26.
Figure 30:
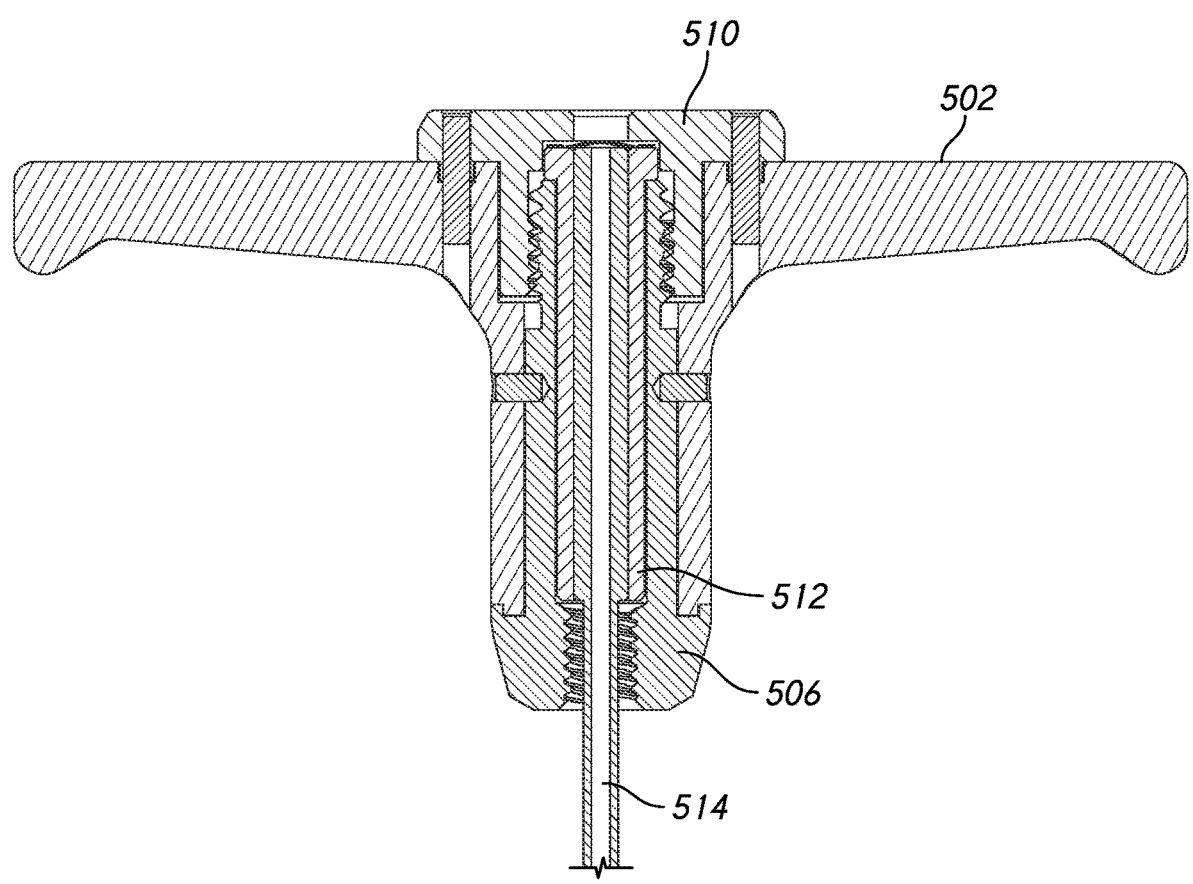
FIG. 30 is a cross-sectional view of the awl handle of FIG. 26.
Figure 33:
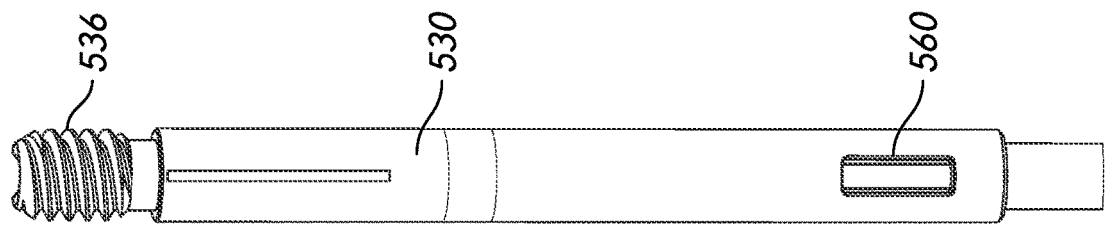
FIG. 33 is a back view of the awl of FIG. 27.
Figure 32:
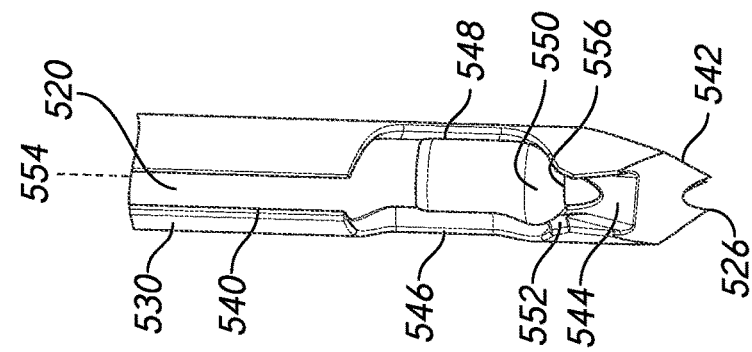
FIG. 32 is another perspective view of the awl of FIG. 27.
Figure 31:
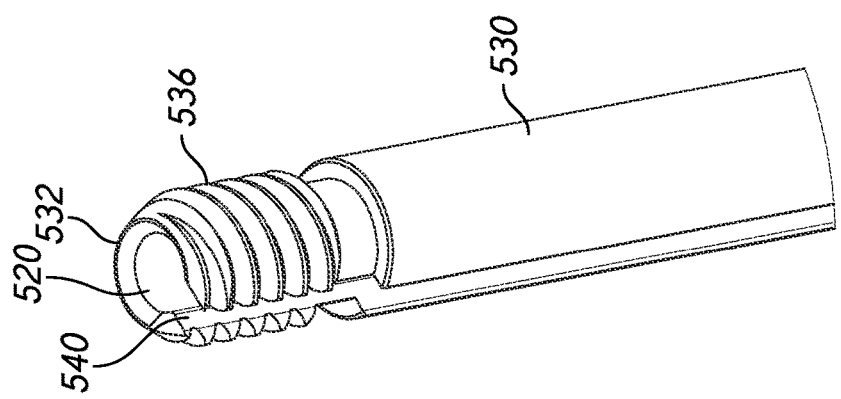
FIG. 31 is a perspective view of the awl of FIG. 27.

FIGS. 26-33 depict views of components for anchoring preparation. FIG. 26 illustrates a perspective view of an awl handle 500. FIG. 27 illustrates a side view of an awl 530. FIG. 28 illustrates a side view of a tip of the awl handle 500. FIG. 29 illustrates a distal view of the awl handle 500. FIG. 30 illustrates a cross-sectional view of the awl handle 500. FIG. 31 illustrates a perspective view of the awl 530. FIG. 32 illustrates another perspective view of the awl 530. FIG. 33 is a back view of the awl 530.

The awl handle 500 can include a T-shaped handle 502. The T-shaped handle 502 can include finger grips 504. The finger grips 504 can facilitate holding or gripping the awl handle 500. The awl handle 500 can include a core 506. The core 506 can be disposed within the T-shaped handle 502. The core 506 can facilitate coupling the awl handle 500 to the awl 530. The core 506 can include a threaded bore 508. The threaded bore 508 can receive a threaded portion of the awl 502.

The awl handle 500 can include an impaction cap 510. The core 506 and the impaction cap 510 can be separate components. The core 506 can couple to the impaction cap 510. The core 506 and the impaction cap 510 can be integrally formed. The core 506 and the impaction cap 510 can be threaded. The impaction cap 510 can be rotated to engage the core 506. The impaction cap 510 can be struck to seat the awl handle 500 and the awl 530, as described herein.

The awl handle 500 can include a shaft cap 512. The shaft cap 512 can be disposed within the core 506. The shaft cap 512 can rotate relative to the core 506. The shaft cap 512 can be disposed within the impaction cap 510. The shaft cap 512 can rotate relative to the impaction cap 510.

The awl handle 500 can include an awl handle shaft 514. The shaft cap 512 and the awl handle shaft 514 can be separate components. The shaft cap 512 can couple to the awl handle shaft 514. The shaft cap 512 and the awl handle shaft 514 can be integrally formed. The awl handle shaft 514 can be cylindrical. The awl handle shaft 514 can be semi-circular. The awl handle shaft 514 can form a portion of an arc. The awl handle shaft 514 can include one or more sliding feature 516. The sliding feature 516 can be a projection. The sliding feature 516 can be a keyed projection. The sliding feature 516 can be a locating key shape. The sliding feature 516 can be a shaped projection. The sliding feature 516 can be generally rectangular. The sliding feature 516 can have straight sides. The sliding feature 516 can be a tapered projection. The sliding feature 516 can be configured to interlock with a sliding feature of the awl 530.

The awl handle 500 can include a lumen 518. The lumen 518 can be shaped to receive the k-wire 210. The lumen 518 can extend through the impaction cap 510. The lumen 518 can extend through the shaft cap 512. The lumen 518 can extend through the awl handle shaft 514. The lumen 518 can extend through the awl handle 500. The lumen 518 can be continuous.

The awl handle shaft 514 can include an awl handle shaft tip 522. The awl handle shaft tip 522 can be a wedge. The awl handle shaft tip 522 can have a blunt edge. The awl handle shaft tip 522 can be configured to lie against the awl 530, as described.

The awl handle 500 can include a proximal end 524 and a distal end 526. The proximal end 524 can include the impaction cap 510. The distal end 526 can include the awl handle shaft 514. The awl handle 500 can have a length between the proximal end 524 and the distal end 526. The length can be along the direction of insertion of the awl 530.

The impaction cap 510 can be inserted into the T-shaped handle 502. The core 506 can be inserted into the T-shaped handle 502. The impaction cap 510 and the core 506 can be coupled. The impaction cap 510, the core 506, and the T-shaped handle 502 can be rotationally fixed relative to each other. One or more of the impaction cap 510, the core 506, and the T-shaped handle 502 can be integrally formed. The awl handle shaft 514 can be inserted into the shaft cap 512. The awl handle shaft 514 and the shaft cap 512 can be coupled. The awl handle shaft 514 and the shaft cap 512 can be integrally formed. The shaft cap 512 can be disposed within the core 506. The shaft cap 512 and the awl handle shaft 514 can rotate relative to the core 506. The shaft cap 512 can be disposed within the impaction cap 510. The shaft cap 512 and the awl handle shaft 514 can rotate relative to the impaction cap 510. One or more of the finger grip 504, the core 506, impaction cap 510, shaft cap 512 and the awl handle shaft 514 can comprise the same material. One or more of the finger grip 504, the core 506, impaction cap 510, shaft cap 512 and the awl handle shaft 514 can comprise different materials.

The awl 530 can include a proximal end 532 and a distal end 534. The awl 530 comprises a length between the proximal end 532 and the distal end 534. The length can be along the direction of insertion of the awl 530.

The awl 530 can include a threaded portion 536. The proximal end 532 can include the threaded portion 536. The threaded portion 536 of the awl 530 can engage the threaded bore 508 of the awl handle 500. The threaded bore 508 can receive the awl 530. The awl 530 can couple to the core 506.

The awl 530 can receive the awl handle shaft 514. The awl 530 can include a lumen 520. The lumen 520 can be cylindrical. The lumen 520 can be semi-circular. The lumen 520 can form a portion of an arc. The lumen 520 can have a corresponding shape to the awl handle shaft 514. The awl 530 can include one or more corresponding sliding features 540. The awl 530 can include one corresponding sliding feature, two corresponding sliding features, three corresponding sliding features, four corresponding sliding features, or any range of two of the foregoing values. The corresponding sliding feature 540 can be a groove. The corresponding sliding feature 540 can be a keyed groove. The corresponding sliding feature 540 can be a locating key shape. The corresponding sliding feature 540 can be a shaped groove. The corresponding sliding feature 540 can be generally rectangular. The corresponding sliding feature 540 can have straight sides. The corresponding sliding feature 540 can be a tapered projection. The corresponding sliding feature 540 can be configured to interlock with the sliding feature 516 of the awl handle 500. The corresponding sliding feature 540 can include an undercut. The corresponding sliding feature 540 can be a shaped recess. The corresponding sliding feature 540 can be engaged by the sliding feature 516, as described herein.

The awl 530 can receive the awl handle shaft 514. The sliding feature 516 of the awl handle shaft 514 is aligned with the corresponding sliding feature 540 of the awl 530. The awl handle shaft 514 is slid within the lumen 520 along the awl 530. The sliding feature 516 of the awl handle shaft 514 can engage the corresponding mating features 540 of the awl 530. The sliding feature 516 and the corresponding sliding feature 540 can prevent or limit rotation of the awl handle shaft 514 relative to the awl 530.

The awl 530 and the awl handle shaft 514 slide until the awl 530 abuts the core 506. The awl 530 can engage the core 506. The T-shaped handle 502 can rotate relative to the awl 530 and the awl handle shaft 514. The T-shaped handle 502 can rotate the core 506. The rotation of the core 506 relative to the awl 510 can engage the threaded portion 536 of the awl 530 with the threaded bore 508 of the core 506. The shaft cap 512, the awl handle shaft 514, and the awl 530 can be remain stationary as the T-shaped handle 502 and the core 506 rotates. The awl 530 can be fully threaded into the core 506. The awl handle shaft 514 can be within the lumen 520 of the awl 530. The awl handle shaft 514 can form an outer surface. The awl handle shaft 514 can interlock with the awl 530.

The awl 530 can have an awl tip 542. The awl tip 542 can include a sharpened point. The awl tip 542 can include a wedge. The awl tip 542 can be a three-side cutting surface. The awl tip 542 can form two or more sharpened surfaces. The awl tip 542 can be configured to penetrate the pedicle. The awl tip 542 can be impacted into bone. The awl tip 542 can guide the placement of the awl 530 relative to the bone. The awl tip 542 can be sharpened to penetrate bone. The distal end 526 can include the awl tip 542.

The awl 530 can include a shaft tip groove 544. The shaft tip groove 544 can receive the awl handle shaft tip 522. The awl handle shaft tip 522 can form the distal end of the sliding feature 516. The awl handle 500 can mate with the awl 530. The awl handle shaft 514 can slide within the lumen 520 until the awl handle shaft tip 522 seats within the shaft tip groove 544. The shaft tip groove 544 can function as a stop to prevent further distal movement of the awl handle shaft 514. The awl 530 can include a pocket 560. The pocket 560 can be disposed along the length of the awl 530.

The awl 530 can function as a bone tie retriever, as described herein. FIG. 32 illustrates a distal portion of the awl 530. The awl 530 can include a retriever portion 546. The retriever portion 546 can be shaped to receive the head 136 of the bone tie 100. The retriever portion 546 can include a channel 548. The channel 548 can include a rounded portion. The channel 548 can include a curvature corresponding to the head 136 of the bone tie 100. The channel 548 can be concave.

The channel 548 can include a ledge 550. The ledge 550 can be flat, curved, or tapered. The ledge 550 can include a curvature that corresponds to the curvature of the head 136 of the bone tie 100. The ledge 550 can be dimensioned to allow for pivotal and/or rotational movement of the head 136 within the channel 548. In some embodiments, the ledge 550 can have a curved or poly-axial surface configured to accept the head 136. In some embodiments, the ledge 550 can be concave. In some embodiments, the ledge 550 can have a concavity that corresponds to a convexity of the head 136. The concavity of the ledge 550 can allow the head 136 to pivot and/or rotate while still retaining the head 136 within the channel 548. The ledge 550 can allow the head 136, and thus the bone tie 100, to pivot 10°, 20°, 30°, 40°, 50°, 60°, 70°, 80°, 90°, 100°, 110°, 120°, 130°, 140°, 150°, 160°, 170°, 180°, or any range of two of the foregoing values.

In particular embodiments, the ledge 550 can allow the head 136, and thus the bone tie 100, to pivot. The bone tie 100 can pivot such that the neck section 114 pivots from generally horizontal to generally skewed. The neck section 114 can rest against the shaft tip groove 544 when the neck section 114 pivots. The ledge 550 can allow the head 136 to abut and rotate, thus positioning the neck section 114 near or within the shaft tip groove 544. The shaft tip groove 544 can extend from the ledge 550. The shaft tip groove 544 can be shaped to accommodate the neck section 114 that extends from the head 136. The ledge 550 can surround the shaft tip groove 544. The shaft tip groove 544 can be shaped to allow the neck section 114 to seat against the shaft tip groove 544. The shaft tip groove 544 can be shaped to prevent the head 136 from passing through the shaft tip groove 544. The shaft tip groove 544 can be sized according to the corresponding bone tie 100.

The retriever portion 546 can include one or more retention features 552. In the illustrated embodiment, the retriever portion 546 includes two retention features 552. The one or more retention features 552 narrow the channel 548 near the distal end. The one or more retention features 552 narrow the ledge 550 near the distal end. The one or more retention features 552 can function to retain the head 136 when the head 136 is seated against the ledge 550.

In some embodiments, the retriever portion 546 may be dimensioned to allow entry of the head 136, or the head 136 and neck section 114, in generally one particular orientation. In some embodiments, the retriever portion 546 may be dimensioned to allow entry of the head 136, or the head 136 and neck section 114, in a range of orientations. In some embodiments, the retriever portion 546 may be dimensioned to allow entry of the head 136 wherein the neck section 114 is generally perpendicular to a longitudinal axis 554 of the awl 530. In some embodiments, the retriever portion 546 may be dimensioned to allow retention of the head 136 wherein the neck section 114 is generally skewed relative to the longitudinal axis 554. In some embodiments, the retriever portion 546 is configured to allow the neck section 114 to pass between the one or more retention features 552. In some embodiments, the retriever portion 546 is configured to allow the neck section 114 to pivot, or pivot and rotate, to extend along the shaft tip groove 544. In some embodiments, the retriever portion 546 is configured to allow the neck section 114 to pivot, or pivot and rotate, from the channel 548 to the shaft tip groove 544. In some embodiments, the shaft tip groove 544 is configured to prevent or limit the head 136 from passing through the shaft tip groove 544. In some embodiments, the one or more retention features 552 is configured to prevent or limit the head 136 from passing through the shaft tip groove 544.

The awl 530 can include a lumen 556. The lumen 556 can extend through the awl 530. The lumen 556 and the lumen 520 of the awl 530 can be aligned. The lumen 556 and the lumen 520 of the awl 530 can be coaxial. The lumen 556 can be a smaller diameter than the lumen 520. The lumen 556 can receive the k-wire 210. The lumen 520 can receive the awl handle shaft 514. The lumen 518 of the awl handle shaft 514 can receive the k-wire 210. The lumen 556 can be disposed through the ledge 550. The lumen 556 can extend through the awl tip 542. The lumen 556 can extend through the retriever portion 546.

The lumen 556 of the awl 530 can align with the lumen 518 of the awl handle shaft 514 when the awl 530 is coupled with the awl handle 500. The k-wire 210 can extend through the awl 530 and the awl handle 500. The awl handle shaft 514 can include the lumen 518. The lumen 556 of the awl 530 and the lumen 518 of the awl handle shaft 514 can together form a lumen for the k-wire 210. The lumen 556 of the awl 530 and the lumen 518 of the awl handle shaft 514 can be guided over the k-wire 210. The lumen 556 of the awl 530 and the lumen 518 of the awl handle shaft 514 can form a continuous path through the awl 530 and the awl handle 500.

The awl 530 can be assembled with the awl handle 500. The awl handle shaft 514 can slide within the lumen 520—the awl 530 until the awl handle shaft tip 522 is seated within the shaft tip groove 544. The T-shaped handle 502 can rotate relative to the awl 530 to engage the threaded portion 536 of the awl 530 with the threaded bore 508 of the awl handle 500. The awl 530 and the awl handle 500 can be coupled. The awl handle 500 and the awl 530 can be slid over the k-wire 210. The k-wire 210 can extend through the portal 300. The portal body 320 can include one or more sections. The portal body 320 can include the first section 334. The first section 334 can extend along the first side 330. The lumen 332 can include the first passageway 338. The first section 334 can form the first passageway 338. The first passageway 338 can form a circular arc. The circular arc of the first passageway 338 can correspond to the diameter of the awl 530 and the sliding feature 516 when the awl 530 and the awl handle 500 are coupled. The awl 530 and the sliding feature 516 can form a circular shape when coupled. The awl handle 500 and awl 530 can slide over the k-wire 210 and through the portal 300. The awl handle 500 and awl 530 can slide along the first passageway 338 of the portal 300.

The awl handle 500 and awl 530 can be further advanced relative to the portal 300. The awl 530 can engage the cored hole formed by the JAMSHIDI needle 200. The impaction cap 510 can be struck to advance the awl tip 542 into the pedicle.

The portal 300 can include the latch 310. In some methods, the outer surface of the awl 530 moves the latch 310 inward as the awl 530 slides relative to the portal 300. The awl 530 can push the latch 310 outward to allow passage of the awl 530 through the lumen 318 of the portal 300. In some methods, the latch release button 312 is depressed by the user. The latch release button 312 can move the latch 310 from the lumen 318. The latch release button 312 can be depressed to allow the awl handle shaft 514 and awl 530 to slide relative to the portal 300.

The awl 530 can include the pocket 560. The awl 530 can be advanced until the pocket 560 is aligned with the latch 310. In some methods, the latch release button 312 can be depressed as the awl handle 500 and awl 530 slide relative to the portal 300. The latch release button 312 can be released when the latch 310 is aligned with the pocket 560. The latch release button 312 can be biased upward when the latch 310 engages the pocket 560.

The corresponding wedge 356 of the latch 310 can engage the pocket 560 of the awl 530. The awl 530 can be secured relative to the portal handle 302 with the latch 310. The latch 310 can be biased inward. The latch 310 can extend into the lumen 318 of the portal handle 302. The latch 310 can engage the pocket 560 to orient the awl 530 relative to the portal 300. The latch 310 can engage the pocket 560 to orient the retriever portion 546. The latch 310 can engage the pocket 560 to ensure the correct rotational orientation of the awl 530 relative to the portal 300. The latch 310 can engage the pocket 560 to ensure the correct translational orientation of the awl 530 relative to the portal 300. The latch 310 can limit or prevent rotation of the awl 530 relative to the portal. The latch 310 can limit or prevent translation of the awl 530 relative to the portal.

7. Lumen Preparation

Figure 34:
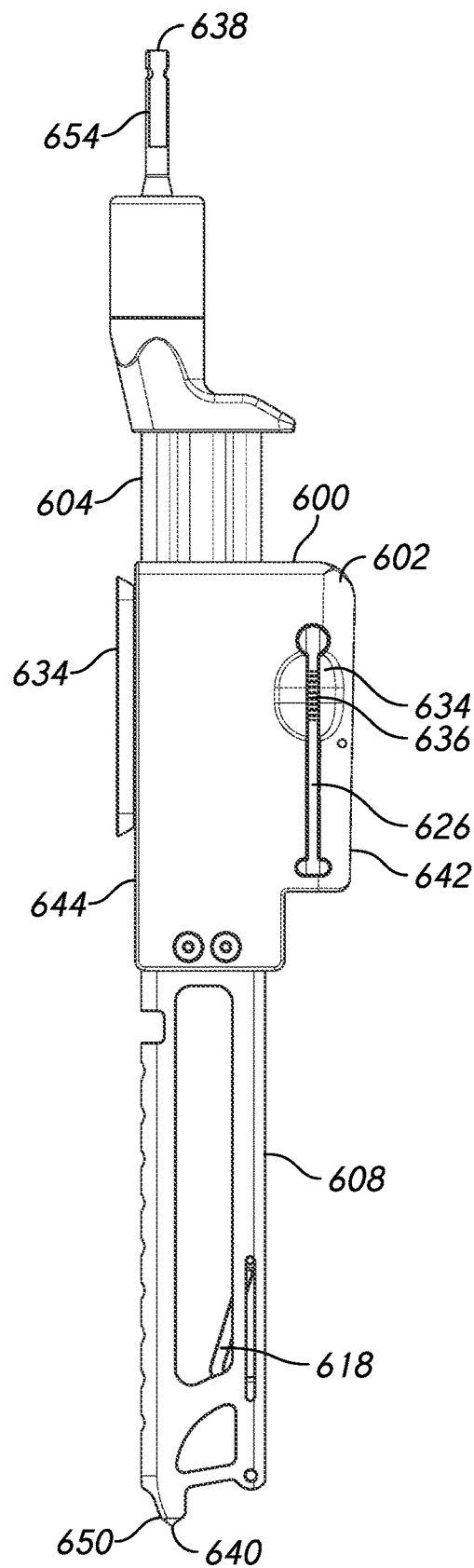
FIG. 34 is a front view of a drill.
Figure 35:
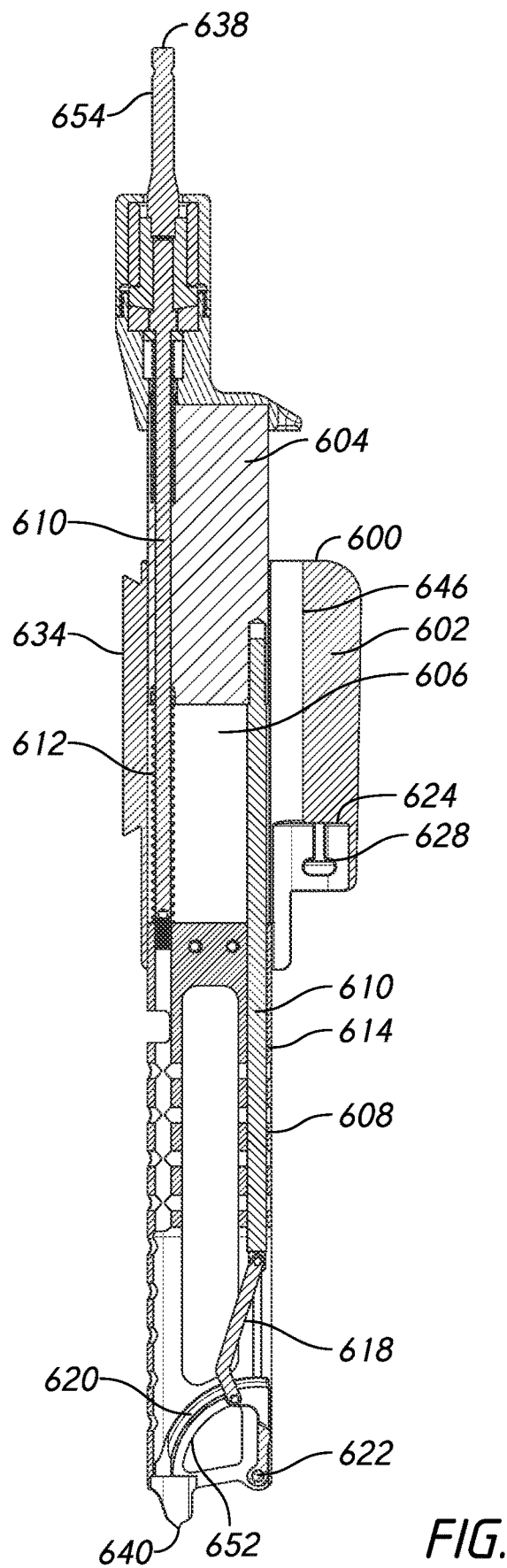
FIG. 35 is a cross-sectional view of the drill of FIG. 34.
Figure 36:
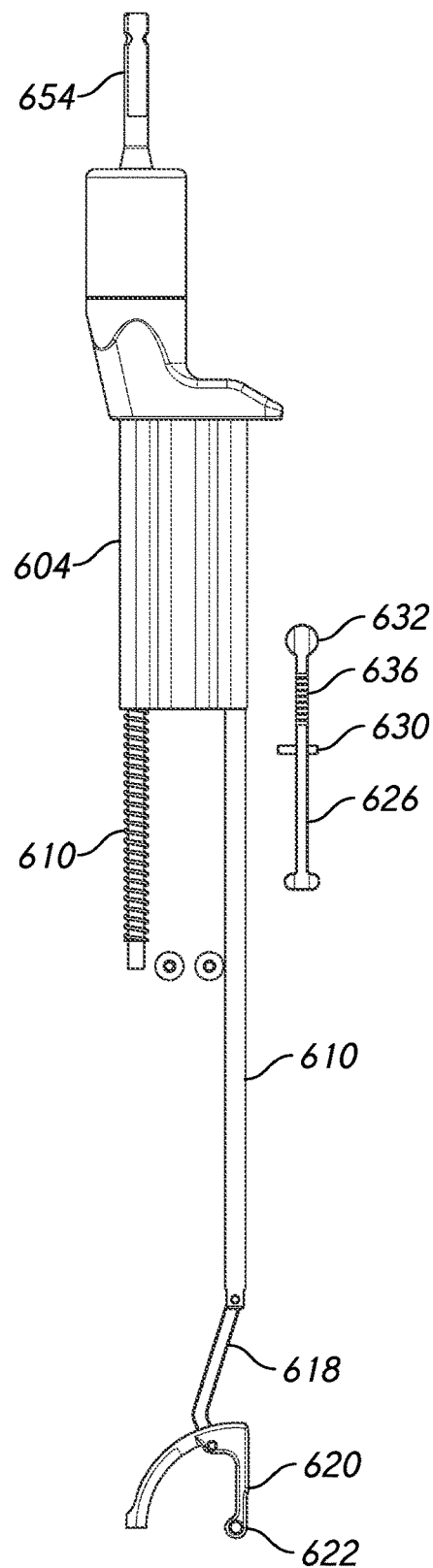
FIG. 36 is a view of internal components of the drill of FIG. 34.
Figure 37:
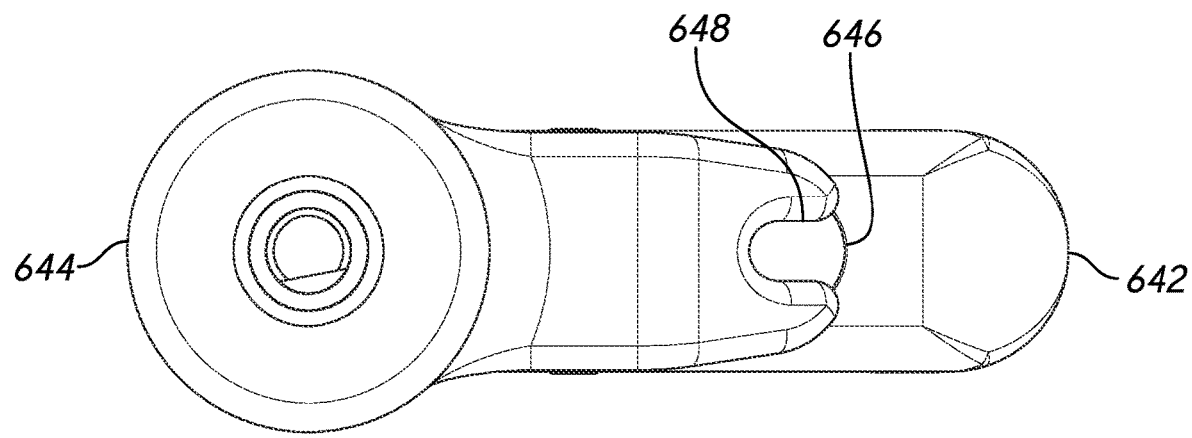
FIG. 37 is a proximal view of the drill of FIG. 34.
Figure 38:
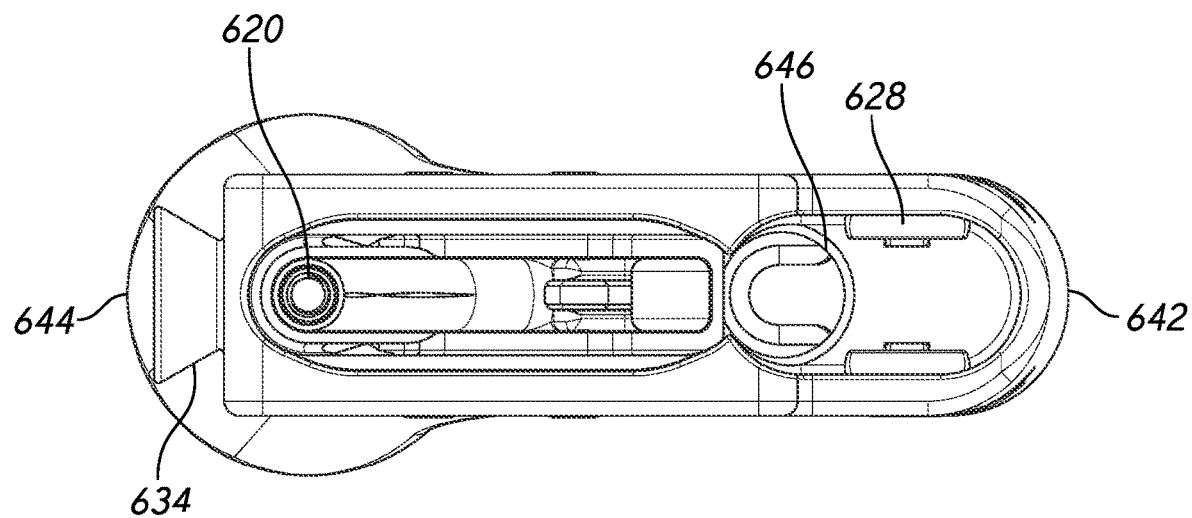
FIG. 38 is a distal view of the drill of FIG. 34.
Figure 39:
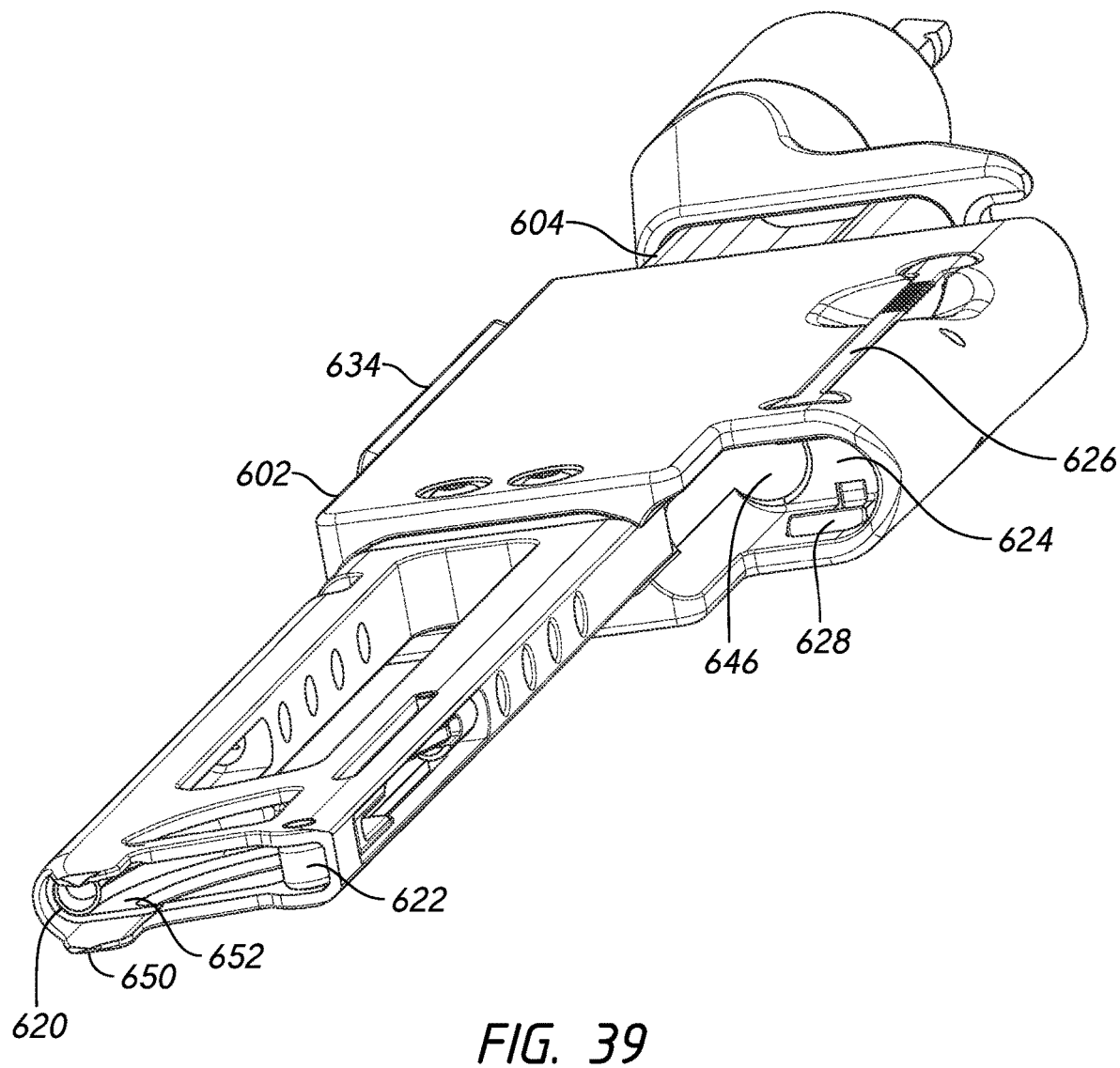
FIG. 39 is a perspective view of the drill of FIG. 34.

FIGS. 34-43 depict views of components for lumen preparation. FIG. 34 illustrates a front view of a drill 600. FIG. 35 illustrates a cross-sectional view of the drill 600. FIG. 36 illustrates a view of internal components of the drill 600. FIG. 37 illustrates a proximal view of the drill 600. FIG. 38 illustrates a distal view of the drill 600. FIG. 39 illustrates a perspective view of the drill 600. FIG. 40 illustrates a front view of a drill bit 670. FIG. 41 is a distal view of the drill bit 670. FIG. 42 is a perspective view of the drill 600 and the drill bit 670. FIG. 43 is a distal view of the drill 600 and the drill bit 670.

The drill 600 can include a drill handle 602. The drill handle 602 can include surfaces allowing a user to grip the drill 600. The drill 600 can include an advancer body 604. The drill handle 602 can be coupled to the advancer body 604. The drill handle 602 and the advancer body 604 can allow sliding between the drill handle 602 and the advancer body 604. The drill handle 602 and the advancer body 604 can comprise the same material. The drill handle 602 and the advancer body 604 can comprise different materials. In some embodiments, the advancer body 604 comprises a more rigid material such as one or more metals and the drill handle 602 comprises a more flexible material such as one or more polymers.

The drill handle 602 can include a cavity 606. The cavity 606 can extend from the proximal end of the drill handle 602. The cavity 606 can extend along the entire length of the drill handle 602, or a portion thereof. The advancer body 604 can be disposed within the cavity 606 of the drill handle 602. The advancer body 604 can extend proximally from the drill handle 602.

The drill 600 can include the drill body 608. The drill body 608 can extend distally from the drill handle 602. The drill handle 602 can be coupled to the drill body 608. The drill handle 602 and the drill body 608 can be coupled with one or more fasteners. The drill handle 602 can be integrally formed with the drill body 608. The drill handle 602 and the drill body 608 can comprise the same material. The drill handle 602 and the drill body 608 can comprise different materials. In some embodiments, the drill body 608 comprises a more rigid material such as one or more metals and the drill handle 602 comprises a more flexible material such as one or more polymers.

The drill 600 can include one or more pins 610. The drill 600 can include two pins 610. The two pins 610 can have different lengths. The two pins 610 can have different functions. The drill 600 can include one or more springs 612. The drill 600 can include one spring 612. The spring 612 can bias one pin 610. The one or more pins 610 and the one or more springs 612 can function as a suspension system. The drill 600 can include one or more channels 614. Each pin 610 can be disposed within the channel 614.

The advancer body 604 can slide downward within the cavity 606. As the advancer body 604 slides downward, the one or more pins 610 slide downward within the one or more channels 614. The one or more pins 610 are pushed by the advancer body 604. The one or more pins 610 can be separately formed from the advancer body 604. The one or more pins 610 and the advancer body 604 can be integrally formed. As the advancer body 604 slides downward, the one or more springs 612 can be compressed. The one or more springs 612 can bias the advancer body 604 upward. FIG. 36 illustrates the drill 600 with the drill body 608 removed.

The advancer body 604 is configured to advance a drill bit 670. The drill bit 670 can be loaded into the drill body 608. One of the pins 610 can engage the drill bit 670. The drill bit 670 can include a drill bit tip 672. The drill bit tip 672 can have a sharpened point. The drill bit tip 672 can include one or more flutes. The drill bit tip 672 can include a spiral blade. The drill bit 670 can include a drill bit shaft 674. The drill bit shaft 674 can be flexible to assume a curved shape. The drill bit 670 can include a keyed shaft 676. The drill bit 670 can include a proximal coupling 678. The proximal coupling 678 can engage one of the pins 610. In some embodiments, the pin 610 includes a threaded bore and the proximal coupling 678 includes a threaded post. In some embodiments, the pin 610 includes a keyed bore and can be configured to engage the keyed shaft 676. In some embodiments, the distal movement of the pin 610 can cause distal movement of the drill bit 670 as described herein. In some embodiments, the proximal movement of the pin 610 can cause proximal movement of the drill bit 670 as described herein. In some embodiments, the rotational movement of the pin 610 can cause rotational movement of the drill bit 670 as described herein. The drill 600 can be reusable. The drill tip 670 can be disposable.

The other pin 610 can be coupled to a linkage 618. The linkage 618 can be coupled to a swing arm 620. The swing arm 620 can be coupled to the drill body 608. The swing arm 620 can be coupled to a pivot bushing 622. The pivot bushing 622 can allow the swing arm 620 to rotate relative to the drill body 608. Downward motion of the pin 610 can cause the swing arm 620 to rotate about the pivot bushing 622. The swing arm 620 forms a portion of an arc. The swing arm 620 can guide the movement of the drill bit 670. The swing arm 620 can rotate relative to the pivot bushing 622 along a portion of an arc of 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, 190 degrees, 200 degrees, or any range of two of the foregoing values.

The advancer body 604 can be released. The one or more springs 612 can bias the advancer body 604 upward. The one or more pins 610 can move upward. The movement of the pin 610 can cause corresponding movement of the linkage 618 and the swing arm 620. The movement of the pin 610 can cause the swing arm 620 to rotate in the opposite direction. The swing arm 620 can be retracted. The movement of the pin 610 can cause corresponding movement of the drill bit 670. The drill bit 670 can be retracted.

The drill 600 can include a latch cavity 624. The drill 600 can receive the latch release button 312 of the portal 300 within the latch cavity 624. The latch cavity 624 can extend from the distal end of the tissue drill handle 602. The latch cavity 624 can have clearance for the latch release button 312. The latch release button 312 can be in a neutral position when received by the latch cavity 624. The latch release button 312 can be biased upward when received by the latch cavity 624. The latch 310 can be biased inward relative to the portal handle 300 when the drill 600 is coupled to the portal handle 302.

The drill 600 can include one or more latch arms 626. The drill handle 602 can include the one or more latch arms 626. The drill 600 can include two latch arms 626. The latch arms 626 can be diametrically opposed. Each latch arm 626 can include a corresponding alignment feature 628. The corresponding alignment feature 628 can be a projection. The portal handle 302 can include one or more alignment features 314. The alignment features 314 can be diametrically opposed. Each alignment feature 314 of the portal 300 can be engaged by the corresponding alignment feature 628 of the drill 600.

The one or more latch arms 626 can be configured to pivot. The drill handle 602 can include pivot pins 630. Each latch arm 626 can be mounted on the pivot pin 630. The latch arm 626 can pivot relative to the pivot pin 630 to engage or disengage the corresponding alignment feature 628 from the alignment feature 314. The drill handle 602 can include a spring 632. The spring 632 can bias the corresponding alignment feature 628 of the latch arm 626 into engagement with the alignment feature 314. The spring 632 can bias two latch arms 626. The spring 632 can bias the corresponding alignment features 628 of the latch arms 626 into engagement with the alignment features 314.

The drill handle 602 can include one or more latch arm grooves 634. The drill handle 602 can include two latch arm grooves 634 corresponding to the two latch arms 626. The latch arm groove 634 can allow the user to pivot the corresponding latch arm 626. The latch arms 626 can include finger grips 636. The finger grips 636 can be depressed by the user to pivot the latch arms 626. The finger grips 636 can be depressed by the user to compress the spring 632. The latch arm 626 can pivot relative to the pivot pin 630. The latch arm 626 can pivot outward relative to the drill handle 602. The corresponding alignment feature 628 can disengage the alignment features 314 when the latch arms 626 are pivoted. The spring 632 can bias the latch arms 626 into engagement with the portal 300 when the latch arms 626 are released. The corresponding alignment features 628 of the latch arms 626 can lock with the alignment features 314 of the portal 300.

The drill 600 can include one or more corresponding sliding features 634. The drill handle 602 can include the corresponding sliding feature 634. The drill 600 can include one corresponding sliding feature, two corresponding sliding features, three corresponding sliding features, four corresponding sliding features, or any range of two of the foregoing values. The corresponding sliding feature 634 can be a dovetail projection. The corresponding sliding feature 634 can be a shaped projection. The corresponding sliding feature 634 can be a tapered projection. The corresponding sliding feature 634 can be configured to interlock with a sliding feature 316 of the portal 300.

The drill 600 can include a proximal end 638 and a distal end 640. The drill 600 comprises a length between the proximal end 638 and the distal end 640. The length can be along the direction of insertion of the drill 600. The proximal end 638 can include the advancer body 604. The distal end 640 can include the drill body 608.

The drill 600 can include a first side 642 and a second side 644. The drill 600 can include a width extending between the first side 642 and the second side 644. The drill 600 can include a maximum width of 20 mm, 25 mm, 30 mm, 35 mm, 40 mm, 45 mm, 50 mm, or any range of two of the foregoing values. The drill 600 can include a thickness. The thickness can correspond to the transverse dimension of the width. The thickness can correspond to the transverse dimension of the first side 642. The thickness can correspond to the transverse dimension of the second side 644. The drill 600 can include a maximum thickness of 2 mm, 3 mm, 4 mm, 5 mm, 6 mm, 7 mm, 8 mm, 9 mm, 10 mm, 11 mm, 12 mm, 13 mm, 14 mm, 15 mm, or any range of two of the foregoing values. The width can be greater than the thickness of the drill 600. The width and thickness of the drill handle 602 can correspond to the width and thickness of the lumen 318 of the portal handle 302. The width and thickness of the drill body 608 can correspond to the width and thickness of the second passageway 340 of the portal body 320.

The drill bit 670 can be inserted into the drill 600. The drill bit 670 can be inserted into the distal end 640 of the drill 600. The drill bit 670 can be inserted into the swing arm 620. The drill bit 670 can be inserted into the swing arm 620 when the swing arm is retracted. The drill bit 670 can be advanced into the drill body 608. The drill bit 670 can be advanced towards one of the pins 610. The drill bit 670 can engage the pin 610. The drill bit 670 and the pin 610 can be rotationally coupled. The drill bit 670 and the pin can be translationally coupled.

The drill 600 with the engaged drill bit 670 can be inserted over the awl 530. The awl handle shaft 514 can be removed. The drill 600 can include a first lumen 646. The first lumen 646 can extend through the drill handle 602. The first lumen 646 can extend through the drill body 608. The advancer body 604 can form the first passageway 648. The first passageway 648 can form a circular arc. The circular arc can correspond to the diameter of the awl 530. The drill 600 can slide relative to the awl 530. The awl 530 can be disposed within the first passageway 648 and the first lumen 646. The first lumen 646 can be positioned closer to the first side 642. The first passageway 648 can be positioned closer to the first side 642.

The portal 300 and the awl 530 can be coupled via the latch 310 when the portal 300 receives the drill 600. The portal body 320 can include the lumen 322. The first section 334 can form the first passageway 338. The awl 530 can be positioned within the first passageway 338 when the portal 300 receives the drill 600. The awl 530 and the portal 300 can be engage via the latch 310 to prevent rotation. The latch 310 can engage the pocket 560 of the awl 530. The second section 336 can form the second passageway 340. The drill body 608 can be positioned within the second passageway 340. The drill body 608 and the second section 336 of the portal 300 can have a corresponding shape to allow sliding. The drill body 608 and the second section 336 can be shaped to prevent rotation. The second passageway 340 can be non-circular.

The awl 530 can be in a fixed spatial relationship when engaged within the portal 300. The awl 530 can be prevented from translation and rotation relative to the portal 300. The drill 600 can be advanced until the corresponding alignment feature 628 engages the stop 324 of the portal 300. The drill 600 can be prevented from translation and rotation relative to the portal 300. The awl 530 can be in a fixed spatial relationship with the drill 600 when both are engaged with the portal. When the awl 530 and the drill 600 are coupled to the portal 300, the awl 530 is a fixed distance relative to the pivot bushing 622 of the drill 600. The awl 530 is in a pre-determined position relative to the swing arm 620 which pivots relative pivot bushing 622. The awl 530 is in a pre-determined position relative to the arc formed by the swing arm 620. The awl 530 is in a fixed position relative to the drill body 608 when the awl 530 and the drill 600 are coupled to the portal 300. The retriever portion 546 faces the swing arm 622. The retriever portion 546 faces inward from the first side 330 of the portal 300. The swing arm 620 faces inward from the second side 332 of the portal 300. The swing arm 620 is aligned with the retriever portion 546.

The drill body 608 can be shaped to engage the anatomy of the patient. The drill body 608 can include a ledge 650. The ledge 650 can include a tapered end. The ledge 650 can be shaped to rest against the pedicle. The ledge 650 can be shaped to rest against the lamina. The ledge 650 can be shaped to engage the anatomy of the patient. The ledge 650 can be shaped to engage a generally horizontal surface of the pedicle and a generally slanted surface of the lamina. The ledge 650 can include a spike. The ledge 650 can be anchored to bone. The ledge 650 can stabilize the drill 600 against the anatomy of the patient. The drill body 608 can include a cavity 652. The cavity 652 can allow the swing arm 620 to rotate. The swing arm 622 can form an arc. The drill body 608 can include a shaped end for engaging the anatomy of the patient. The drill body 608 can include a shaped end for positioning relative to the anatomy.

The drill 600 can be inserted into the portal 300. The drill 600 can slide from the proximal end 326 of the portal 300.

The drill body 608 can slide within the lumen 318. The drill body 608 can slide within the second passageway 340. The sliding feature 316 of the portal 300 can be engaged by the corresponding sliding feature 634 of the drill 600. The sliding feature 316 and the corresponding sliding feature 634 can have a corresponding shape to allow sliding. The sliding feature 316 and the corresponding sliding feature 634 can have a corresponding shape to prevent or limit rotation. The corresponding sliding feature 634 of the drill 600 advances to the stop 324 of the portal 300. The latch cavity 624 receives a portion of the portal handle 302. The drill 600 can slide over the awl 530. The awl 530 can extend through the first passageway 648 and the first lumen 646 of the drill 600.

The drill 600 can lock into place relative to the portal 300. The corresponding alignment feature 628 of the latch arm 626 can pivot into engagement with the alignment feature 314 of the portal 300. The awl 530 can extend past the first passageway 648 and the first lumen 646 of the drill 600.

The drill 600 and the drill bit 670 can form a lumen within bone. The swing arm 620 can rotate as the advancer body 604 is advanced. The swing arm 620 rotates relative to the pivot bushing 622. The drill bit shaft 674 can be flexible. The drill bit shaft 674 can follow the curved path of the swing arm 620 as the swing arm 620 advances in an arc. The drill bit 670 can be coupled to the pin 610. The pin 610 can be coupled to a drill coupler 654. The drill coupler 654 can rotate to rotate the drill bit 670. The drill coupler 654 can rotate the drill bit 670 indirectly through the pin 610. The drill coupler 654 can rotate the drill bit 670 at several thousand revolutions per minute. The drill coupler 654 can rotate the drill bit 670 to drill a lumen in bone.

The user sequentially advances and release the advancer body 604. The advancer body 604 advances the swing arm 620 in an arc. The drill bit 670 forms the hole. The advancer body 604 can be sequentially advanced and released relative to the drill handle 602 to drill the hole along the curved arc of the swing arm 620. The drill bit 670 can drill a lumen as the swing arm 620 rotates. The drill bit 670 can form the lumen. The drill bit shaft 674 can be flexible. The drill bit tip 672 can rotate to form a lumen along the arc of the swing arm 620. The swing arm 620 and the drill bit 670 can form a curved lumen within bone. The swing arm 620 can swing in an arc relative to the drill body 608. The swing arm 620 can carry the drill bit tip 672 and a portion of the drill tip shaft 674. The drill bit 670 can rotate relative to the swing arm 620 to bore a lumen. The drill bit 670 can be rotated by a drill motor coupled to the drill coupler 654. The drill coupler 654 can be disposed toward the proximal end of the drill 600.

The swing arm 620 can be moved in a circular arc by manipulation of the advancer body 604. FIGS. 42 and 43 show the fully advanced swing arm 620 and drill bit 670. The drill bit tip 672 can extend beyond the swing arm 620. The drill bit tip 672 can advance with the swing arm 620. The ledge 650 can be against bone, such that the lumen is formed within the bone. The swing arm 620 rotates relative to the pivot bushing 622. The swing arm 620 rotates upon the downward movement of the advancer body 604. The advancer body can abut the drill handle 602 when the swing arm 620 is fully advanced. The drill 600 can provide tactile feedback when the swing arm 620 is fully advanced. The swing arm 620 rotates toward the retriever portion 546 of the awl 530. The retriever portion 546 is an opposing target for the swing arm 620. The swing arm 620 can be moved between an advanced configuration and a retracted configuration. The swing arm 620 can be moved by the advancer body 604. The advancer body 604 moves the one or more pins 610 axially along the drill body 608. The downward manipulation of the advancer body 604 causes a longitudinal movement of the pin 610. In some embodiments, the advancer body 604 can be connected to the pin 610 directly, in which case the pin 610 is also manipulated by upward and downward motion of the advancer body 604. In other embodiments, the advancer body 604 can be connected to the pin 610 through mechanisms such as gears or hinges, wherein manipulation of the advancer body 604 translates into longitudinal movement of the pin 610. The pin 610 can be straight or curved or a combination of these shapes. The pin 610 causes movement of the linkage 618. The linkage 618 can be straight or curved or a combination of these shapes. The linkage causes movement of the swing arm 620. The other pin 610 causes movement of the drill bit 670. The drill bit 670 and the swing arm 620 simultaneously advance. The drill bit 670 and the swing arm 620 both advance with the movement of the advancer body 604.

Different curved shapes of the swing arm 620 are possible. In other embodiments, the swing arm 620 can have at least one straight segment and at least one curved segment. In some embodiments, the swing arm 620 is shaped to have a curved distal portion that has a desired arc so that the swing arm 620 follows a specified path when extended. In still other embodiments, a power source may be provided for hydraulic, pneumatic, or other power-assisted manipulation of the swing arm 620. The swing arm 620 can be generally curved to form a curved lumen. The swing arm 620 can be generally straight to form a straight lumen.

The swing arm 620 can comprise a tubular member. The swing arm 620 can include the rotating drill bit 670 disposed coaxially within. The rotating drill bit shaft 674 can be flexible. The rotating drill bit tip 672 can be guided by the swing arm 620. The swing arm 620 can have sufficient rigidity to guide the flexible rotating drill bit 670 into the shape of the desired lumen. The drill bit 670 can bend in the lateral direction. The drill bit 670 can create a curved cutting path. The drill bit 670 can be rotated by a power drill via drill coupler 654 to achieve the desired revolutions per minute to cut bone. The drill bit 670 can be advanced and retracted by the advancer body 604. The user can move the advancer body 604 distally until the advancer body 604 abuts the drill handle 602. The advancer body 604 can abut the drill handle 602 when the swing arm 620 is fully advanced. The advancer body 604 can abut the drill handle 602 when the swing arm 620 completes an arc. The advancer body 604 can abut the drill handle 602 when the swing arm 620 is aligned with the first lumen 646 of the drill 600. The advancer body 604 can abut the drill handle 602 when the swing arm 620 extends to the awl 530.

The swing arm 620 can be sized to be able to pass through the articular processes of the vertebrae. The resulting hole from the swing arm 610 and the drill bit 670 is sized for the head 136 of the bone tie 100 to be inserted. The swing arm 620 can have a diameter in the range of about 1 mm to 5 mm, preferably about 2 mm to 4 mm, and most preferably about 3 mm. The end of the drill bit 670 can include a cutting surface for creating the lumen. The drill bit 670 can be of any appropriate configuration and with any number of points. In some embodiments, the drill bit 670 may be round, flat, beveled or stepped.

The drill bit 670 can be connected to the drill coupler 654 to provide the axial rotation. The drill coupler 654 can have a configuration that is complementary to a coupling of a powered drill. In some embodiments, the drill coupler 654 can have a feature to provide an anti-rotational connection, such as for example a flat surface, or a shaft having a square or hexagonal cross-section. The drill coupler 654 can rotate one pin 610. The pin 610 can function as a drive shaft. The drill coupler 654 can rotate the drill bit 670.

The awl 530 can include the retriever portion 546. The retriever portion 546 can be shaped to receive the swing arm 620. The retriever portion 546 can be a target member for the swing arm 620. The swing arm 620 can abut the awl 530 when the lumen is formed. The swing arm 620 can extend into the retriever portion 546 when the lumen is formed. The awl 530 can be in the path of travel of the swing arm 620. The awl 530 can facilitate visualizing the trajectory of the swing arm 620 through the articular processes. In some embodiments, the awl 530 can provide stabilization of the portal 300 as the swing arm 620 and the drill bit 670 passes or cuts through the bone. In some embodiments, the ledge 650 of the drill 600 can provide stabilization of the portal 300 as the swing arm 620 and the drill bit 670 passes or cuts through the bone.

The drill 600 can be used by positioning the drill bit 670 against an articular process. When the drill 600 is actuated and the drill bit 670 is rotated, the swing arm 620 forms a curved arc and the drill bit 670 cuts through both articular processes 20, 22 toward the awl 530. The drill bit 670 forms a predicable path toward the awl 530. The awl 530 is correctly positioned relative to the drill 600 since both the awl 530 and the drill 600 are engaged by the portal 300. The portal 300 engages the pocket 560 of the awl 530. The pocket 560 can be disposed along the length of the awl 530. When the latch 310 of the portal 300 engages the pocket 560 of the awl, the rotational position of the awl 530 is fixed relative to the portal 300. When the latch 310 of the portal 300 engages the pocket 560 of the awl 530, the translational position of the awl 530 is fixed relative to the portal 300. The drill 600 engages the portal 300. The latch arms 626 engage the portal 300. When the corresponding alignment features 628 of the latch arms 626 engage the alignment features 314 of the portal 300, the rotational position of the drill 600 is fixed relative to the portal 300. When the corresponding alignment features 628 of the latch arms 626 engages the alignment features 314 of the portal 300, the translational position of the drill 600 is fixed relative to the portal 300. When drill body 608 engages the lumen 318 of the portal 300, the rotational position of the drill 600 is fixed relative to the portal 300. When drill body 608 engages the second passageway 340 of the portal 300, the rotational position of the drill 600 is fixed relative to the portal 300.

Once the lumen is formed, the swing arm 620 and the drill bit 670 can be retracted by releasing the advancer body 604. The swing arm 620 can retract under the influence of the spring 612. The lumen can be utilized with the bone tie 100 to anchor or stabilize the facet joint. The lumen can be utilized with the bone tie 100 to alter the spacing or motion at the facet joint. The drill 600 can be removed, leaving the awl 530 and the portal 300.

8. Fusion Preparation

Figure 46:
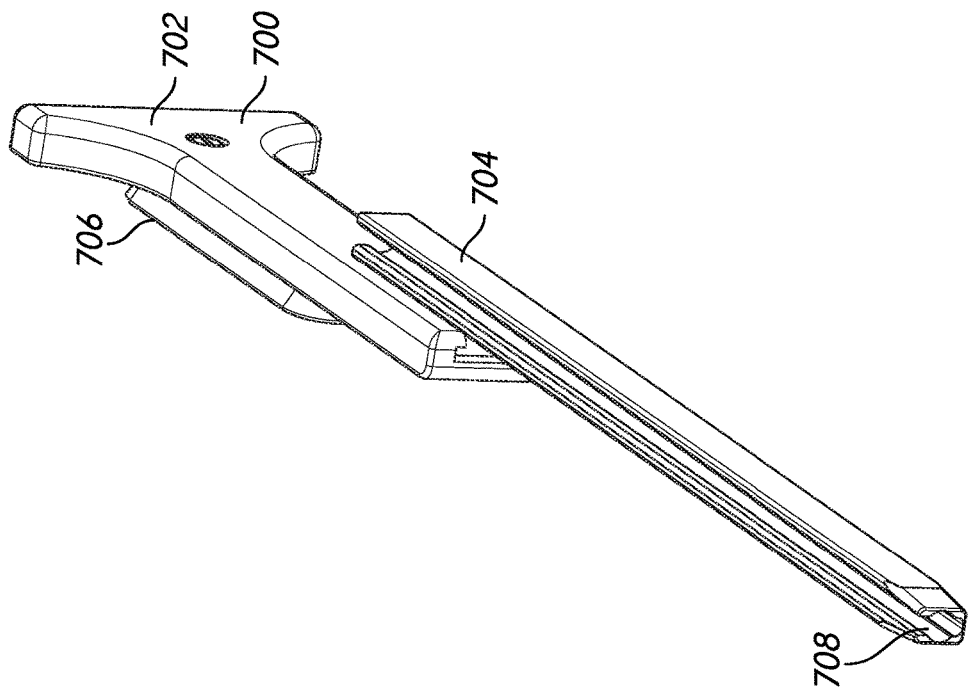
FIG. 46 is a perspective view of the implant shuttle of FIG. 44.
Figure 45:
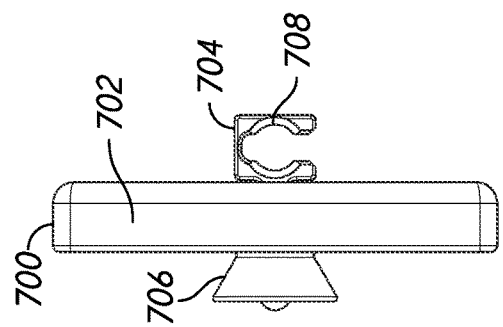
FIG. 45 is a proximal view of the implant shuttle of FIG. 44.
Figure 44:
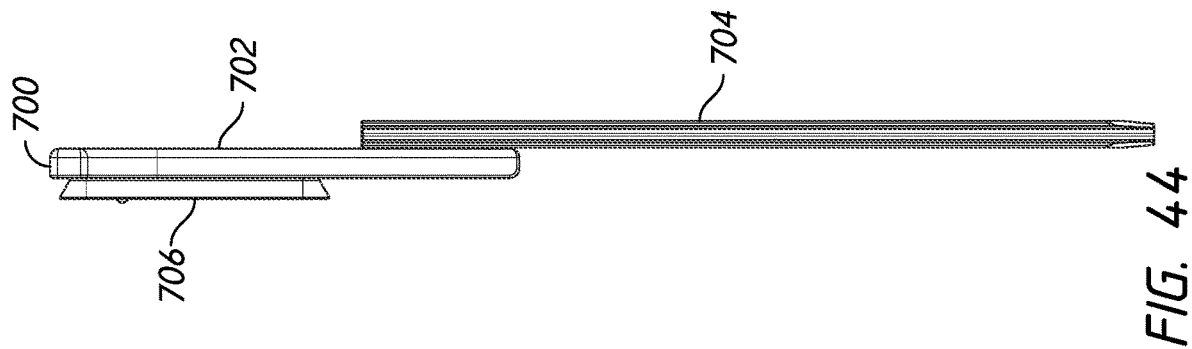
FIG. 44 is a front view of an implant shuttle.
Figure 47:
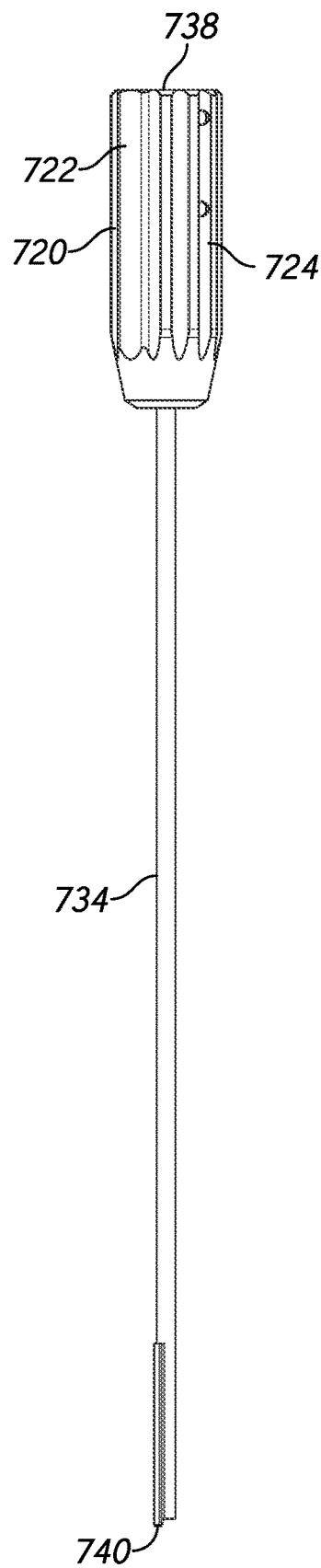
FIG. 47 is a front view of an implant catcher.
Figure 48:
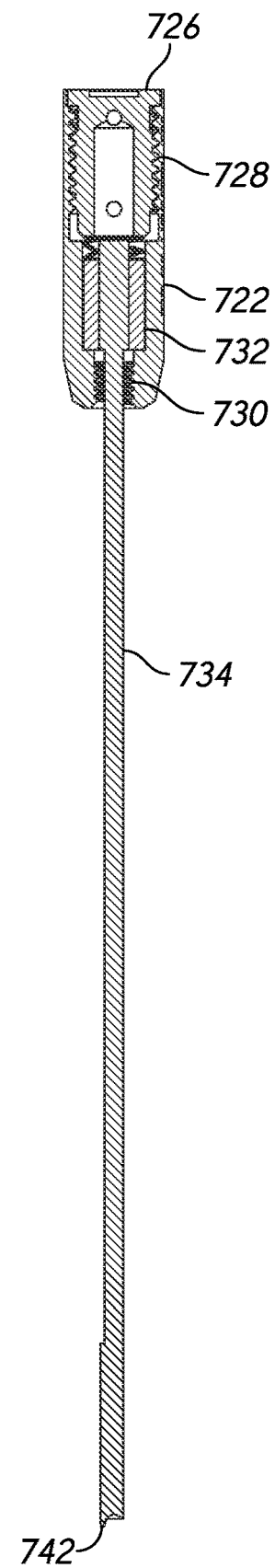
FIG. 48 is a cross-sectional view of the implant catcher of FIG. 47.
Figure 49:
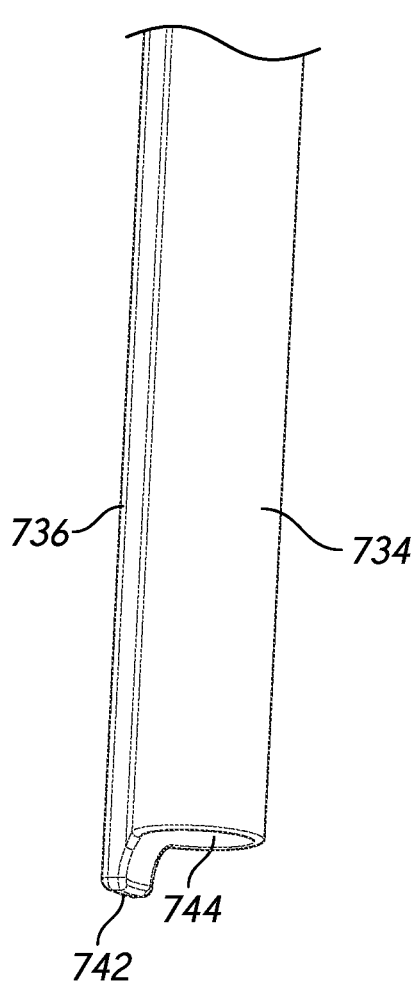
FIG. 49 is a distal view of the implant catcher of FIG. 47.
Figure 50:
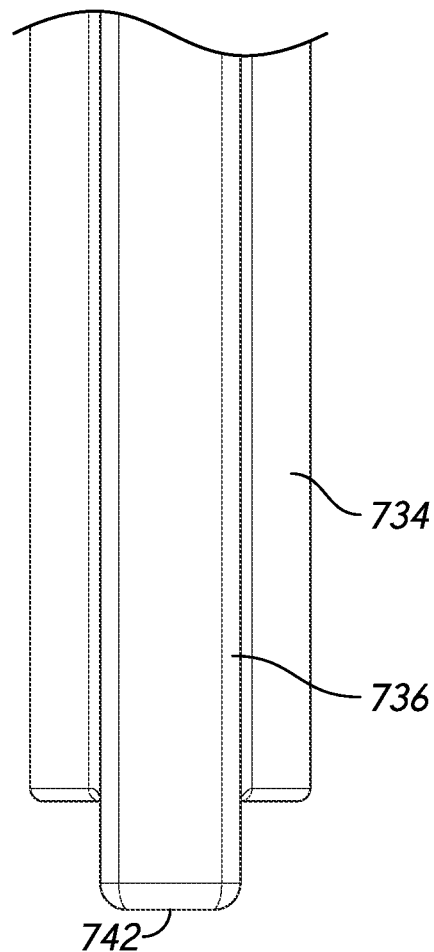
FIG. 50 is another distal view of the implant catcher of FIG. 47.
Figure 51:
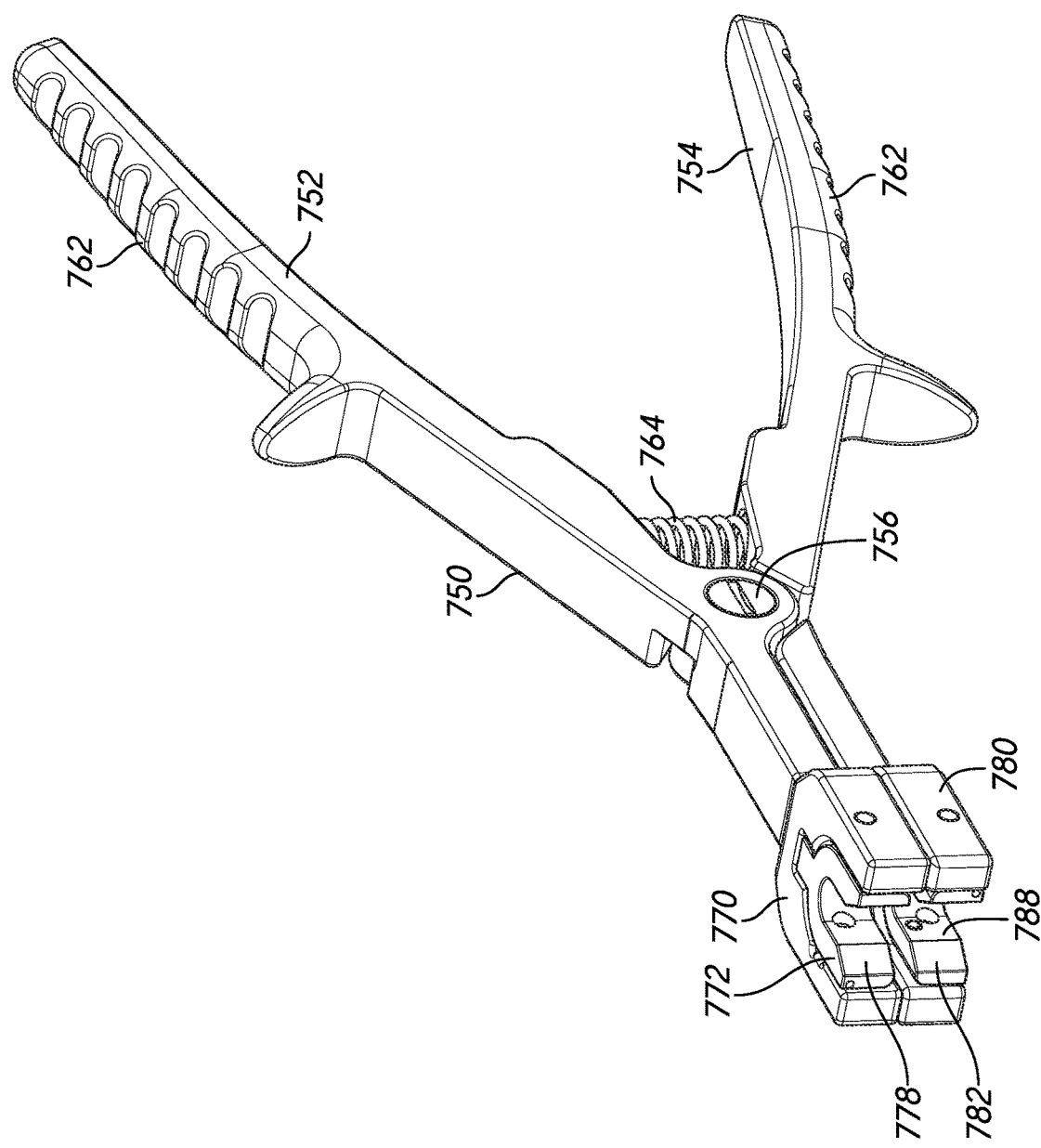
FIG. 51 is a perspective view of an awl jack.
Figure 52:
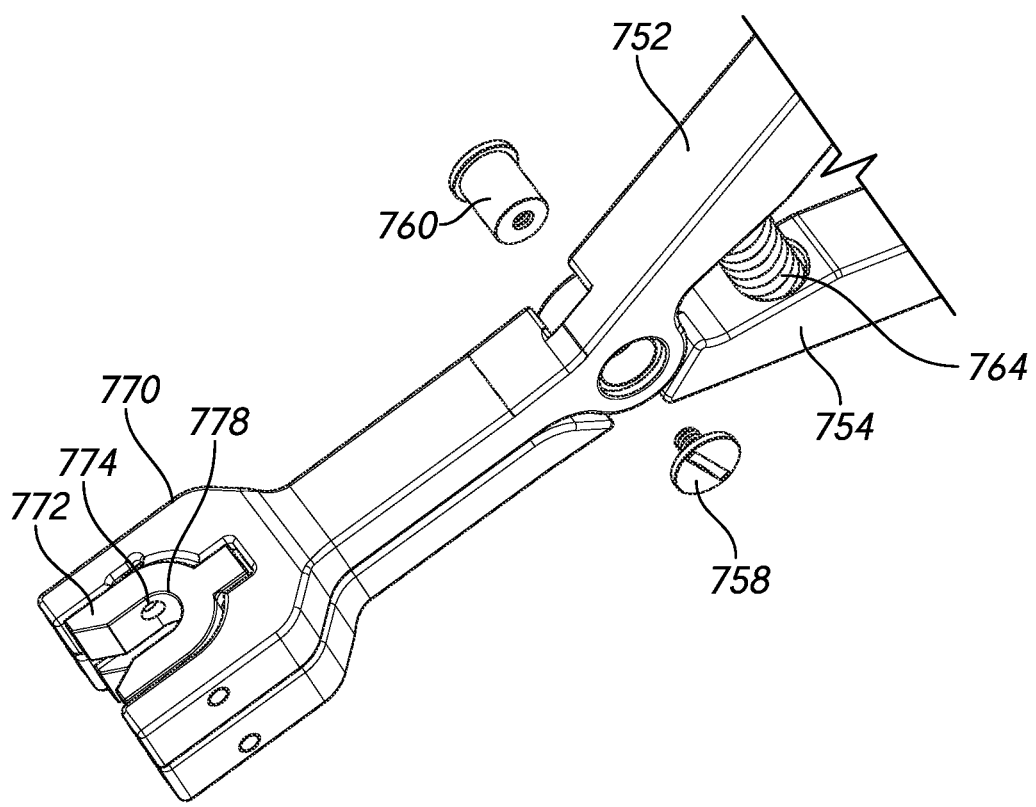
FIG. 52 is another perspective view of the awl jack of FIG. 51.
Figure 53:
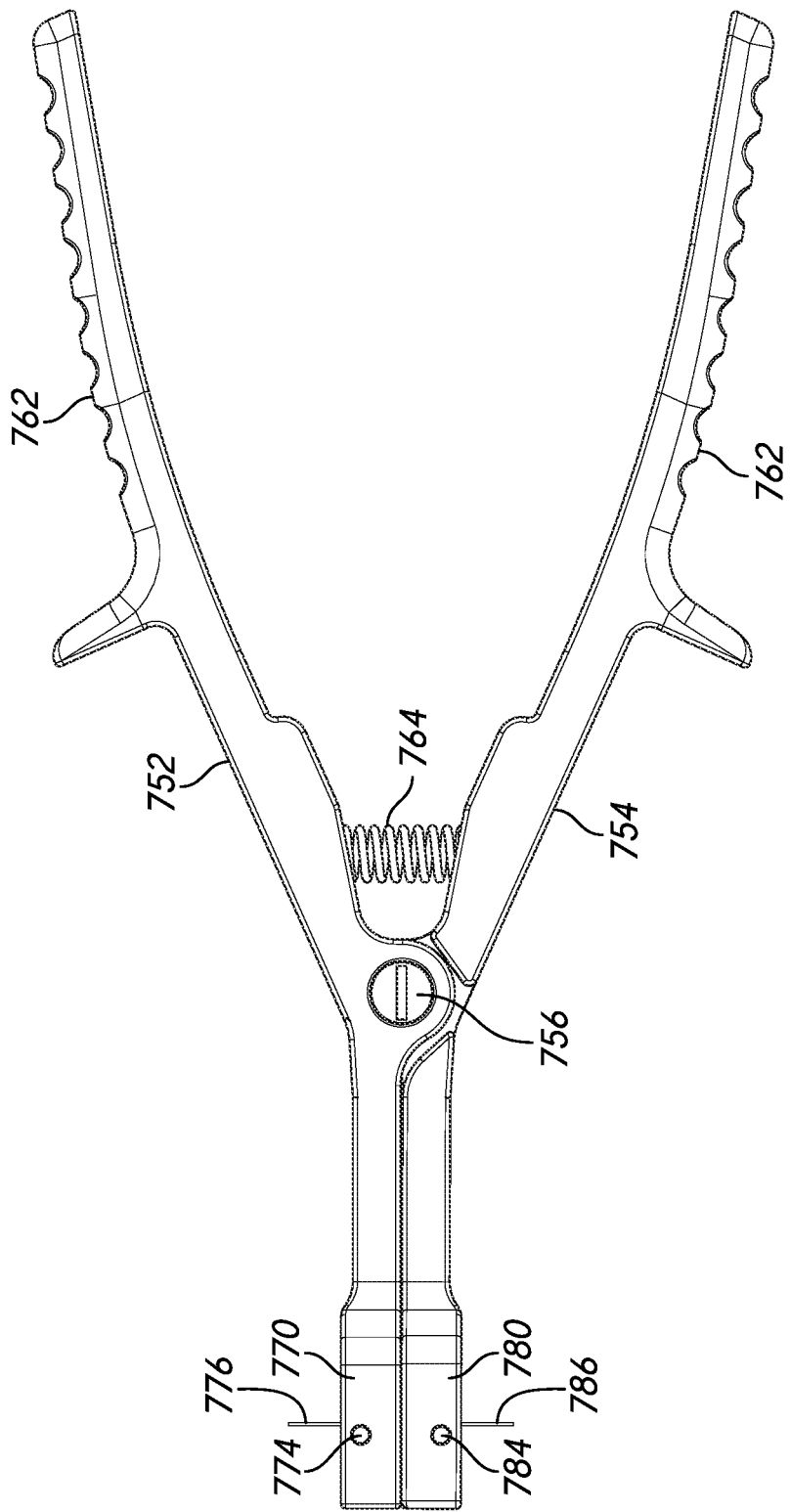
FIG. 53 is a side view of the awl jack of FIG. 51.
Figure 54:
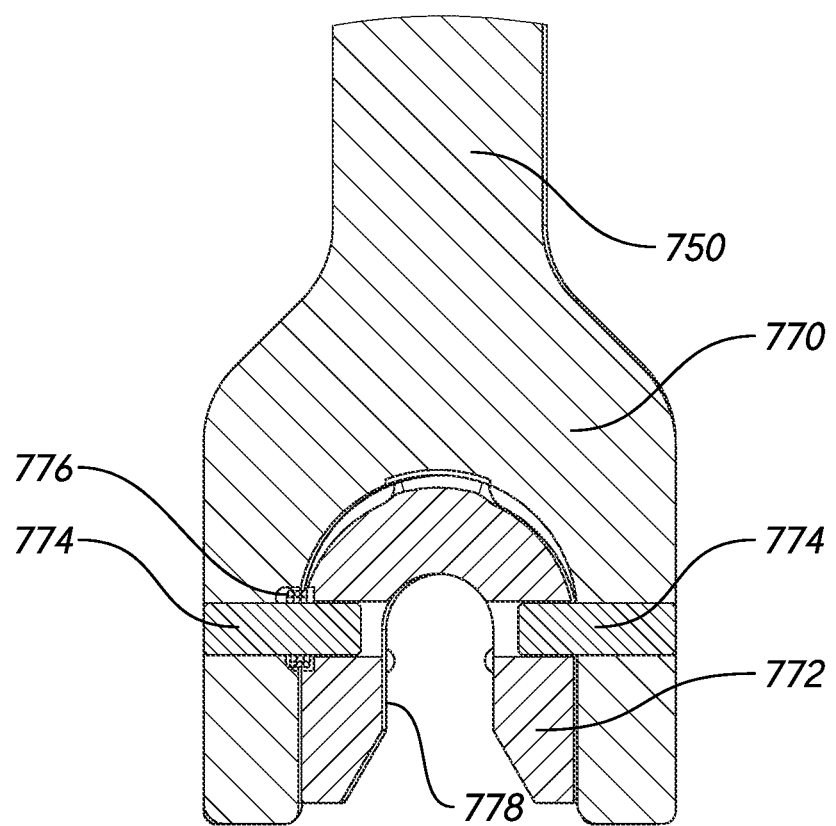
FIG. 54 is a cross-sectional view of the awl jack of FIG. 51.

FIGS. 44-54 depict views of components for fusion preparation. FIG. 44 illustrates a front view of an implant shuttle 700. FIG. 45 illustrates a proximal view of the implant shuttle 700. FIG. 46 illustrates a perspective view of the implant shuttle 700. FIG. 47 illustrates a front view of an implant catcher 720. FIG. 48 illustrates a cross-sectional view of the implant catcher 720. FIG. 49 illustrates a distal view of the implant catcher 720. FIG. 50 illustrates another distal view of the implant catcher 720. FIG. 51 illustrates a perspective view of an awl jack 750. FIG. 52 illustrates another perspective view of the awl jack 750. FIG. 53 illustrates a side view of the awl jack 750. FIG. 54 illustrates a cross-sectional view of the awl jack 750.

The implant shuttle 700 can guide the bone tie 100. The implant shuttle 700 can include an implant shuttle handle 702. The implant shuttle 700 can include an implant shuttle body 704. The implant shuttle handle 702 can be coupled to the implant shuttle body 704. The implant shuttle handle 702 and the implant shuttle body 704 can be coupled with one or more fasteners. The implant shuttle handle 702 can be integrally formed with implant shuttle body 704. The implant shuttle handle 702 and the implant shuttle body 704 can comprise the same material. The implant shuttle handle 702 and the implant shuttle body 704 can comprise different materials. In some embodiments, the implant shuttle body 704 comprises a more rigid material such as one or more metals and the implant shuttle handle 702 comprises a more flexible material such as one or more polymers.

The implant shuttle 700 can include one or more corresponding sliding features 706. The implant shuttle handle 702 can include one or more corresponding sliding features 706. The implant shuttle 700 can include one corresponding sliding feature, two corresponding sliding features, three corresponding sliding features, four corresponding sliding features, or any range of two of the foregoing values. The corresponding sliding feature 706 can be a dovetail projection. The corresponding sliding feature 706 can be a shaped projection. The corresponding sliding feature 706 can be a tapered projection. The corresponding sliding feature 706 can be configured to interlock with a sliding feature 316 of the portal 300. The sliding feature 316 of the portal 300 can be engaged by the corresponding sliding feature 706. The sliding feature 316 and the corresponding sliding feature 706 can have a corresponding shape to allow sliding. The sliding feature 316 and the corresponding sliding feature 706 can have a corresponding shape to prevent or limit rotation.

The implant shuttle 700 can include a passageway 708. The implant shuttle body 704 can include the passageway 708. The passageway 708 can be shaped to receive the head 136 of the bone tie 100. The passageway 708 can have an elongate shape. The passageway 708 can be shaped to receive the first section 108, the second section 110 and/or the third section 112 of the bone tie 100. The passageway 708 can be shaped to receive of the length of the bone tie 100. The first section 108, the second section 110 and/or the third section 112 of the bone tie 100 can have a greater width than the diameter of the bone tie 100. The passageway 708 can be open along the length of the implant shuttle body 704. The fastener section 106 can be larger than the passageway 708. The bone tie 100 can be passed through the open side of the passageway 708. The bone tie 100 can be passed through the open side after the loop is formed. The bone tie 100 can be passed through the open side after the third section 112 and/or the second section 110 pass through the fastener section 106.

The implant shuttle body 704 can align the passageway 708 with the lumen formed in the articular processes. The bone tie 100 can be passed through the passageway 708 of the implant shuttle body 704. The bone tie 100 can be fed through the passageway 708 and into the bone lumen. The bone tie 100 can follow the curved lumen formed in the bone. The bone tie 100 can follow the lumen formed by the drill 600. The bone tie 100 can be fed through the implant shuttle body 704 until the head 136 reaches the retriever portion 546 of the awl 530.

The implant catcher 720 can include an implant catcher handle 722. The implant catcher handle 722 can include finger grips 724. The finger grips 724 can facilitate holding or gripping the implant catcher 720. The implant catcher 720 can include a plug 726. The plug 726 can be threaded. The implant catcher handle 722 can include a proximal threaded bore 728. The plug 726 can couple with the proximal threaded bore 728. The plug 726 can be threaded and rotated to be engaged with the implant catcher handle 722.

The implant catcher handle 722 can include a distal threaded bore 730. The distal threaded bore 730 can engage the awl 530. The awl 530 can include a threaded portion 536. The threaded portion 536 can include the proximal end 532. The threaded portion 536 of the awl 530 can engage the distal threaded bore 730 of the implant catcher handle 722. The proximal threaded bore 728 and the distal threaded bore 730 can have the same diameter. The proximal threaded bore 728 and the distal threaded bore 730 can have different diameters. The proximal threaded bore 728 and the distal threaded bore 730 can have the same pitch. The proximal threaded bore 728 and the distal threaded bore 730 can have different pitches. The proximal threaded bore 728 and the distal threaded bore 730 can be continuous. The proximal threaded bore 728 and the distal threaded bore 730 can be separate threaded sections within the implant catcher handle 722.

The implant catcher 720 can include a shaft cap 732. The shaft cap 732 can be disposed within the implant catcher handle 722. The shaft cap 732 can rotate within the implant catcher handle 722. The shaft cap 730 can rotate relative to the plug 726. The shaft cap 732 and the plug 726 can be separate components. The shaft cap 732 and the plug 726 can couple to the handle 722.

The implant catcher 720 can include an implant catcher shaft 734. The awl implant catcher shaft 734 can be cylindrical. The implant catcher shaft 734 can be semi-circular. The implant catcher shaft 734 can form a portion of an arc. The shaft cap 732 and the implant catcher shaft 734 can be separate components. The shaft cap 732 can couple to the implant catcher shaft 734. The shaft cap 732 and the implant catcher shaft 734 can be integrally formed. The implant catcher shaft 734 can include one or more sliding feature 736. The sliding feature 736 can be a projection. The sliding feature 736 can be a keyed projection. The sliding feature 736 can be a locating key shape. The sliding feature 736 can be a shaped projection. The sliding feature 736 can be generally rectangular. The sliding feature 736 can have straight sides. The sliding feature 736 can be a tapered projection. The sliding feature 736 can be configured to interlock with the corresponding sliding feature 540 of the awl 530.

The implant catcher 720 can include a proximal end 738 and a distal end 740. The implant catcher handle 722 can include the proximal end 738. The implant catcher shaft 734 can include the distal end 740. The implant catcher handle 722 and the plug 726 can be rotationally fixed relative to each other. The shaft cap 732 and the implant catcher shaft 734 can rotate relative to the implant catcher handle 722. The shaft cap 732 and the implant catcher shaft 734 can rotate relative to the plug 726. One or more components can be coupled. The implant catcher handle 722 and the plug 726 can be coupled. The implant catcher handle 722 and the plug 726 can be integrally formed. The shaft cap 732 and the implant catcher shaft 734 can be coupled. The shaft cap 732 and the implant catcher shaft 734 can be integrally formed. One or more of the implant catcher handle 722, the plug 726, the shaft cap 732, and the implant catcher shaft 734 can comprise the same material. One or more of the implant catcher handle 722, the plug 726, the shaft cap 732, and the implant catcher shaft 734 can comprise different materials.

The awl 530 can include the proximal end 532 and the distal end 534. The lumen 520 of the awl 530 can receive the implant catcher shaft 734. The awl 530 can include one or more corresponding sliding feature 540. The corresponding sliding feature 540 can be a groove. The corresponding sliding feature 540 of the awl 530 can be engaged by sliding feature 736 of the implant catcher 720.

The implant catcher shaft 734 is slid into the lumen 520 the awl 530. The sliding feature 736 can engage the corresponding sliding feature 540 of the awl 530. The sliding feature 736 and the corresponding sliding feature 540 can allow sliding. The sliding feature 736 and the corresponding sliding feature 540 can prevent or limit rotation of the implant catcher shaft 734 relative to the awl 530.

The implant catcher shaft 734 can include a shaft tip 742. The implant catcher shaft 734 can include a lumen 744. The shaft tip 742 can be a wedge. The shaft tip 742 can have a blunt edge. The shaft tip 742 can be configured to lie against the awl 530, as described. The shaft tip 742 can be pronged. The shaft tip 742 can have a shaped surface. The sliding feature 736 can mate with the awl 530. The sliding feature 736 can form a portion of the outer surface when the implant catcher 720 is coupled to the awl 530.

The awl 530 can include the retriever portion 546. The retriever portion 546 can be shaped to receive the head 136 of the bone tie 100. The retriever portion 546 can include the channel 548. The channel 548 can be concave to receive the head 136. The channel 548 can include the ledge 550. The ledge 550 can include a curvature that corresponds to the curvature of the head 136. In some embodiments, the ledge 550 can have a curved or poly-axial surface configured to accept the head 136.

The implant catcher shaft 734 can slide relative to the retriever portion 546 of the awl 530. In some embodiments, the implant catcher shaft 734 can be positioned a fixed distance from the ledge 550. The implant catcher 720 can be lowered relative to the head 136. The head 136 can be positioned relative to the awl 530 before the implant catcher 720 is lowered. The distal threaded bore 730 of the implant catcher handle 722 can engage the threaded portion 536 of the awl 530. The implant catcher handle 722 can rotate as the awl 530 remains stationary. The shaft cap 532 and the implant catcher shaft 734 can remain stationary as the implant catcher handle 722 rotates. The implant catcher shaft 734 can remain stationary with the awl 530. The implant catcher handle 722 can be rotated until the awl 530 fully engages the distal threaded bore 730 of the implant catcher handle 722. The awl 530 can bottom out against the distal threaded bore 730 of the implant catcher handle 722. The shaft tip 742 can be disposed relative to the retriever portion 546. The abutment of the awl 530 and the implant catcher handle 722 can provide tactile feedback that the shaft tip 742 is positioned relative to the awl 530.

The implant catcher 720 can secure the head 136 relative to the awl 530. The shaft tip 742 can allow the neck section 114 to extend from the awl 530. The neck section 114 can extend through a passageway formed by the shaft tip 742 and the awl 530. The shaft tip 742 can be in a fixed position relative to the awl 530. The shaft tip 742 can be lowered relative to the awl 530 to prevent removal of the head 136 from the awl 530. The shaft tip 742 can retain the head 136 within the awl 530. The passageway formed by the shaft tip 742 and the awl 530 can be smaller than the diameter of the head 136. The head 136 can pivot when the shaft tip 742 is positioned relative to the awl 530. The ledge 550 can allow the head 136, and thus the bone tie 100, to pivot when captured by the shaft tip 742. The bone tie 100 can pivot such that the neck section 114 pivots from generally horizontal to generally skewed when the bone tie 100 is captured by the shaft tip 742. The shaft tip 742 retains the head 136 within the channel 548. The neck section 114 can pivot into the shaft tip groove 544 of the awl 530. The implant catcher 720 can retain the head 136 within the awl 530. The head 136 can have limited rotational movement relative to the awl 530 when the implant catcher 720 is lowered. The head 136 can have limited translational movement relative to the awl 530 when the implant catcher 720 is lowered.

The awl jack 750 can include a first handle 752 and a second handle 754. The awl jack 750 can include a pivot pin 756. The first handle 752 and the second handle 754 can pivot relative to each other via the pivot pin 756. The first handle 752 can include a lumen to receive the pivot pin 756. The second handle 754 can include a lumen to receive the pivot pin 756. The pivot pin 756 can include a pivot threaded cap 758 and a pivot threaded base 760. The pivot pin 756 can couple the first handle 752 and the second handle 754. The pivot pin 756 can allow the first handle 752 and the second handle 754 to pivot relative to each other.

The first handle 752 and the second handle 754 can include finger grips 762. The finger grips 762 can facilitate holding or gripping the first handle 752 and the second handle 754. The first handle 752 and the second handle 754 can be biased. The awl jack 750 can include a spring 764. The spring 764 can be disposed between the finger grips 758 and the pivot pin 756. The spring 764 can bias the first handle 752 and the second handle 754 away from each other.

The first handle 752 includes a first saddle 770. The first handle 752 can include a first swivel head 772. The first handle 752 can include one or more pins 774. The first handle 752 can include two pins 774. The two pins 774 can be diametrically opposed. The first handle 752 can include one or more torsion springs 776. The torsion spring 776 can couple the first saddle 770 and the first swivel head 772. The torsion spring 776 can bias the first saddle 770 and the first swivel head 772 into alignment. The first swivel head 772 can swivel relative to the first saddle 770. The first swivel head 772 can have at least one degree of freedom relative to the first saddle 770. The first swivel head 772 can rotate relative to the one or more pins 774. The torsion spring 776 can bias the first swivel head 772 relative to the first saddle 770. The first swivel head 772 can receive the end of the torsion spring 776. The torsion spring 776 can wrap around one of the pins 774. The torsion spring 776 can exert a torque in the opposite direction that it is twisted. The first swivel head 772 can include a passageway 778. The passageway 778 can correspond to the diameter of the awl 530.

The second handle 754 can include a second saddle 780. The second handle 754 can include a second swivel head 782. The second handle 754 can include one or more pins 784. The second handle 754 can include two pins 784. The two pins 784 can be diametrically opposed. The second handle 754 can include one or more torsion springs 786. The torsion spring 786 can couple the second saddle 780 and the second swivel head 782. The torsion spring 786 can bias the second saddle 780 and the second swivel head 782 into alignment. The second swivel head 782 can swivel relative to the second saddle 780. The second swivel head 774 can have at least one degree of freedom relative to the second saddle 780. The second swivel head 782 can rotate relative to the one or more pins 784. The torsion spring 786 can bias the second swivel head 782 relative to the second saddle 780. The second swivel head 782 can receive the end of the torsion spring 786. The torsion spring 786 can wrap around one of the pins 784. The torsion spring 786 can exert a torque in the opposite direction that it is twisted. The second handle 754 can include a passageway 788. The passageway 788 can correspond to the diameter of the awl 530.

The awl jack 750 can lift the awl 530 relative to the pedicle. The awl 530 and the implant catcher 720 can be coupled. The threaded portion 536 of the awl 530 can engage the distal threaded lumen 730 of the implant catcher 720. The awl jack 750 can be positioned relative to the proximal end of the awl 530. The awl jack 750 can be positioned relative to the implant catcher handle 722. The first swivel head 772 and the second swivel head 784 can engage the awl 530. The awl 530 can be disposed within the passageway 778 of the first swivel head 772 and the passageway 788 of the second swivel head 782.

The finger grips 762 of first handle 752 and the second handle 754 can be moved toward each other. The user can compress the spring 764. The first handle 752 and the second handle 754 pivot relative to the pivot pin 756. The first saddle 770 and the second saddle 780 move away from each other. The first swivel head 772 and the second swivel head 784 can move away from each other. The first swivel head 772 can swivel relative to the first saddle 770. The second swivel head 784 can swivel relative to the second saddle 784. The first swivel head 764 and the second swivel head 774 swivel to remain axially aligned along the length of the awl 530. The first saddle 762 and the second saddle 772 move away from each other thereby lifting the awl 530 and the implant catcher 720. The awl 530 and the implant catcher 720 can be coupled. The awl 530 and the implant catcher 720 can be unitarily lifted relative to the pedicle.

9. Fusion Preparation

Figure 55:
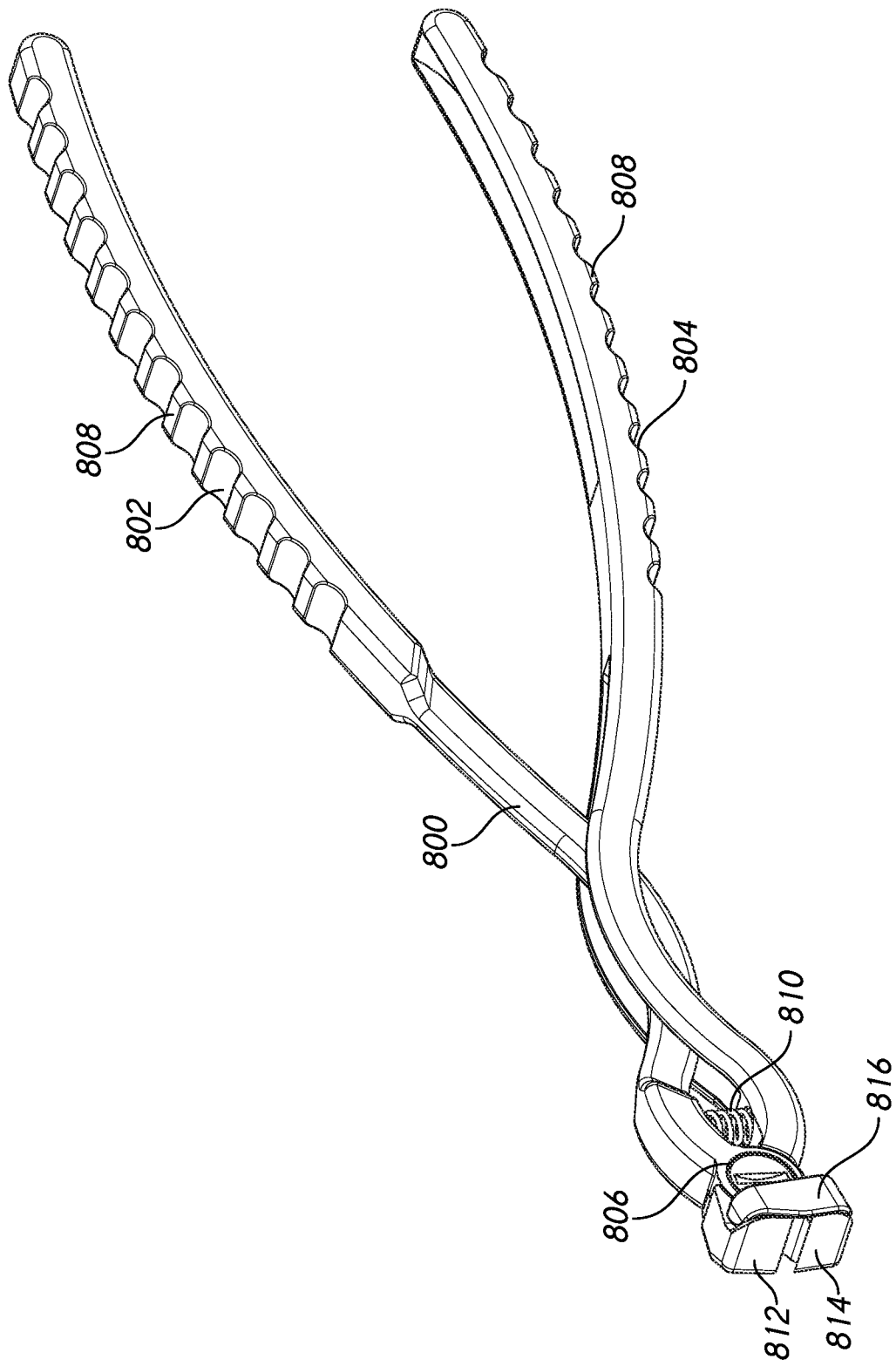
FIG. 55 is a perspective view of a guarded flush cutter.
Figure 57:
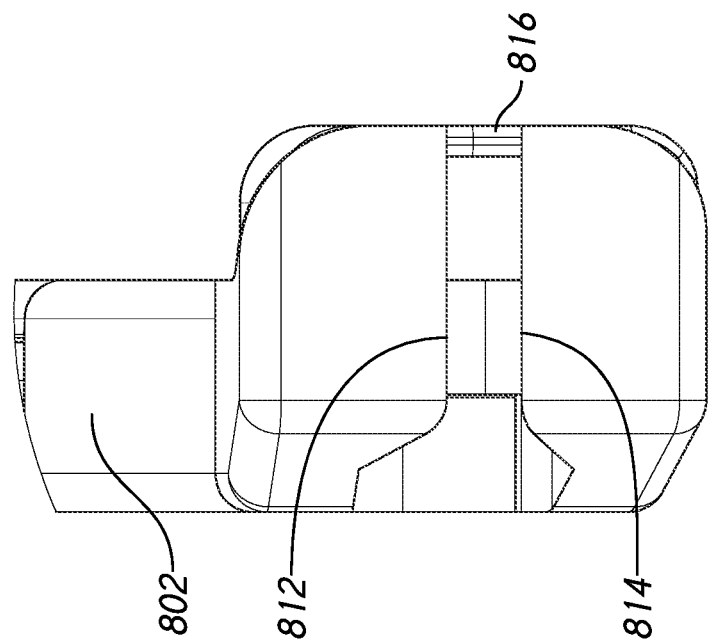
FIG. 57 is a front view of the guarded flush cutter of FIG. 55.
Figure 56:
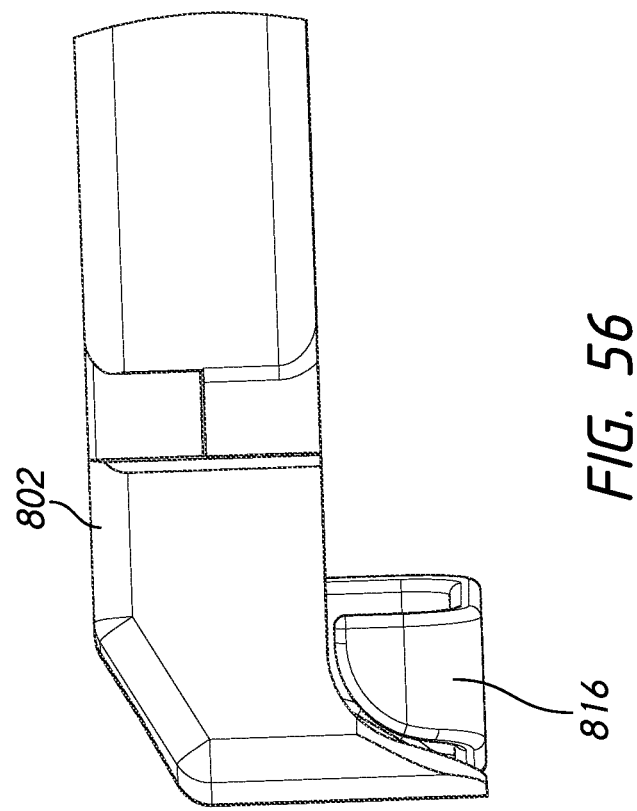
FIG. 56 is a top view of the guarded flush cutter of FIG. 55.
Figures 58, 59:
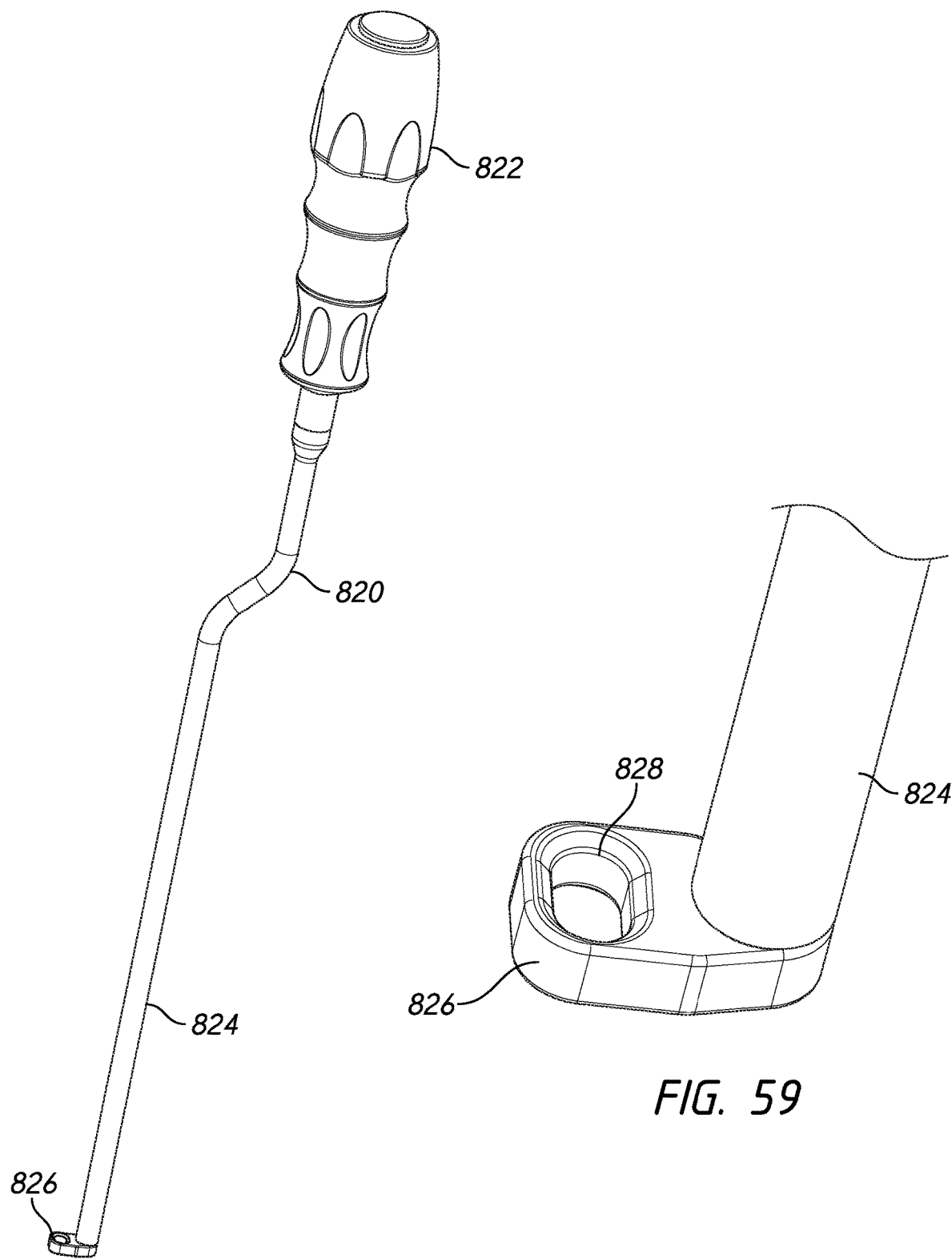
FIG. 58 is a perspective view of a head pusher.
FIG. 59 is a view of a distal portion of the head pusher of FIG. 58.
Figure 60:
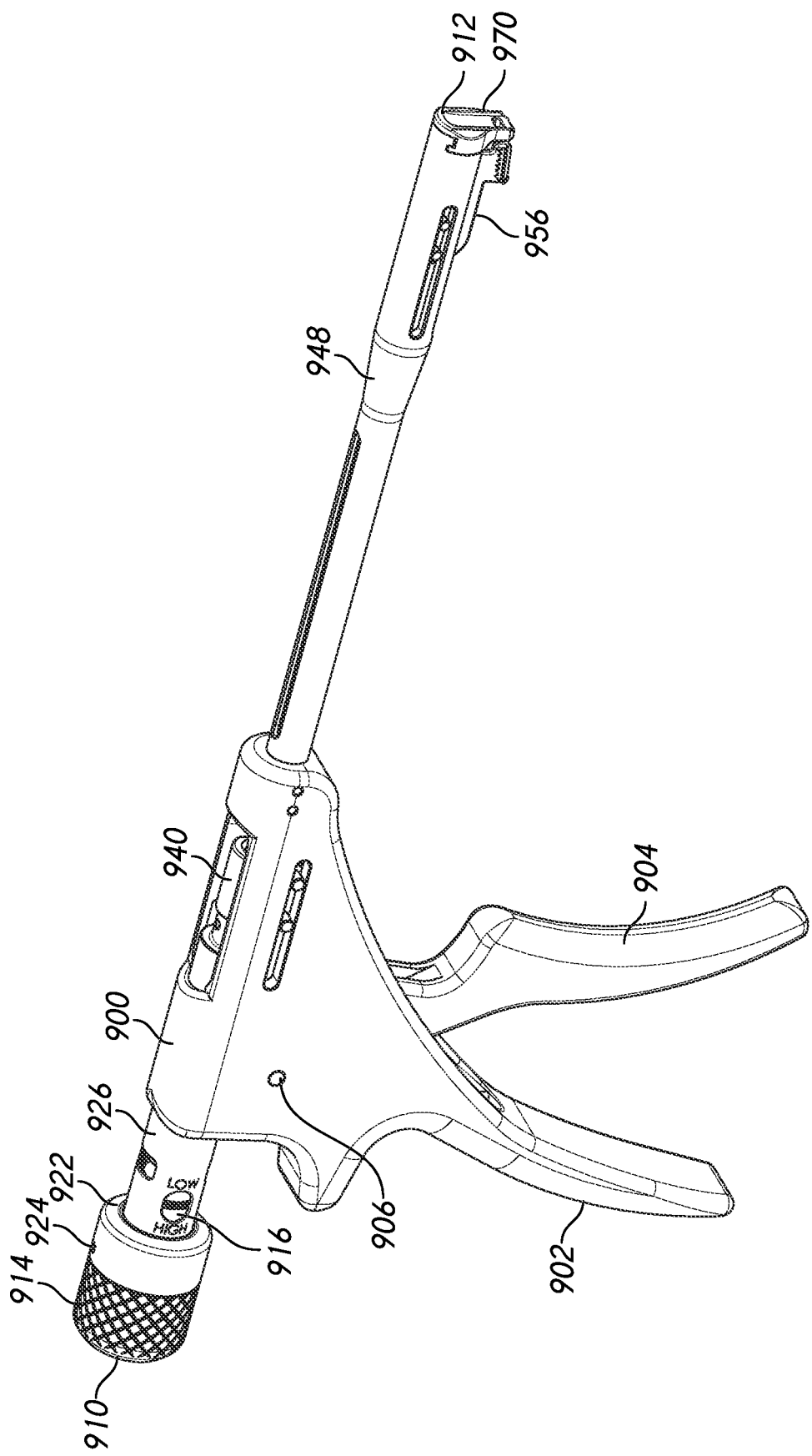
FIG. 60 is a perspective view of a tensioner.
Figure 61:
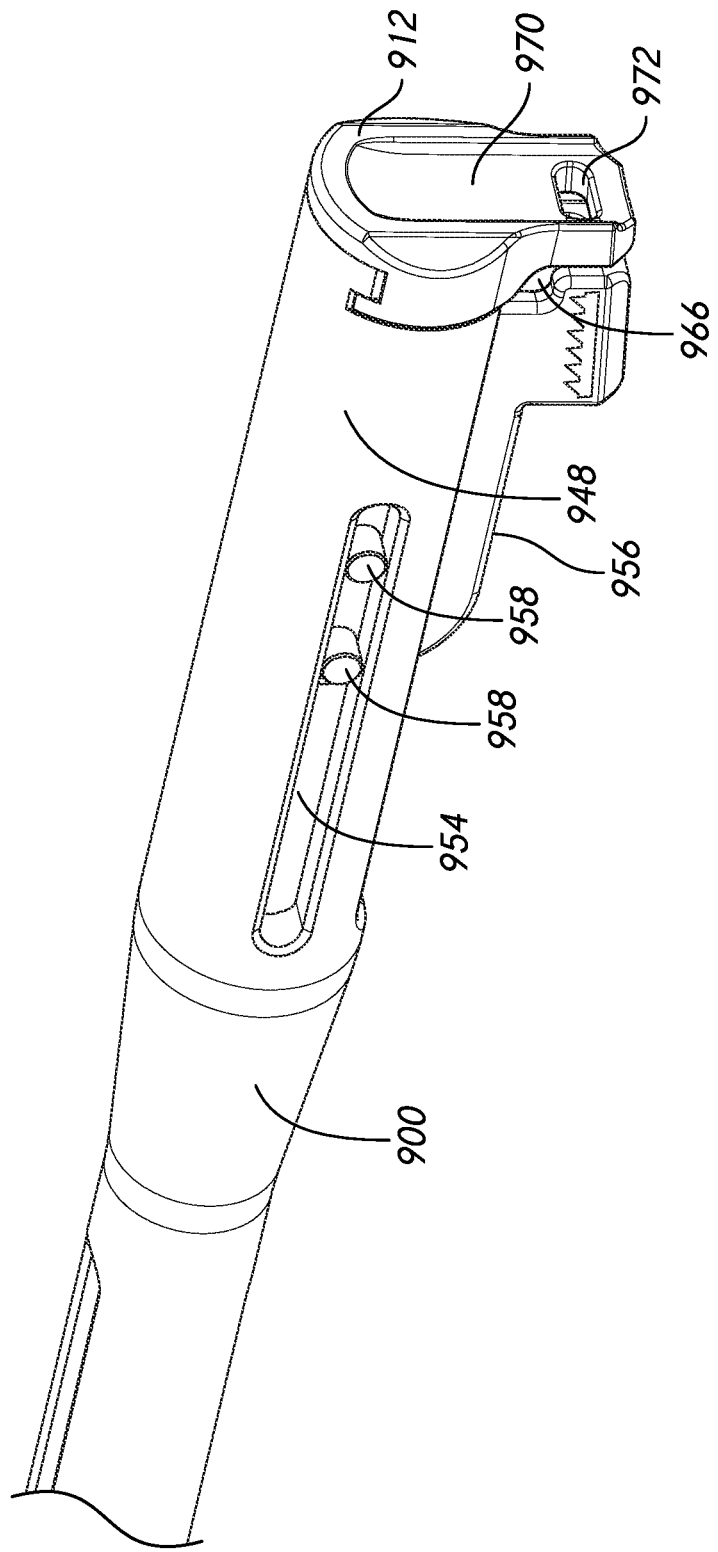
FIG. 61 is a view of a distal portion of the tensioner of FIG. 60.
Figure 62:
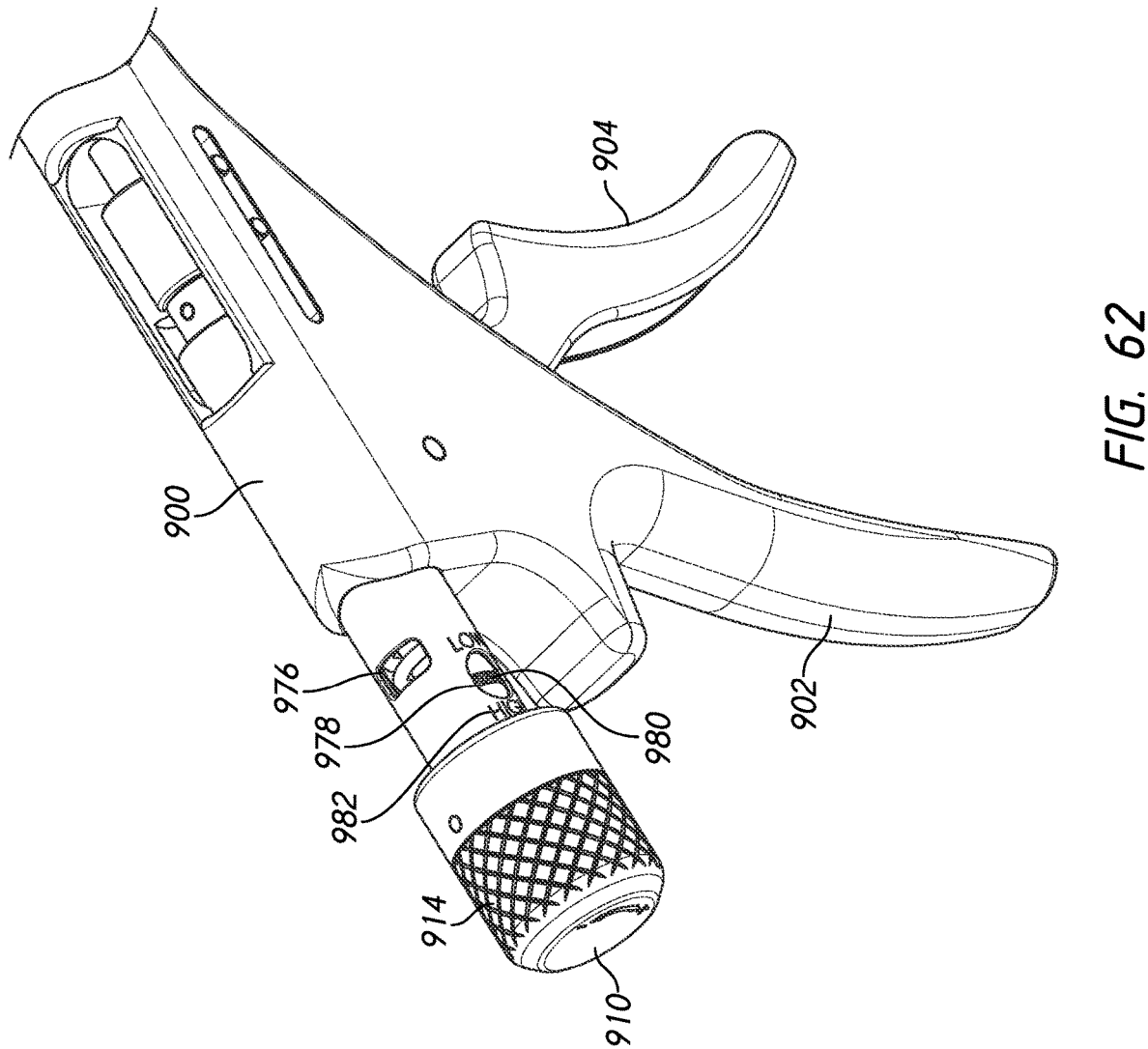
FIG. 62 is a view of a proximal portion of the tensioner of FIG. 60.
Figure 63:
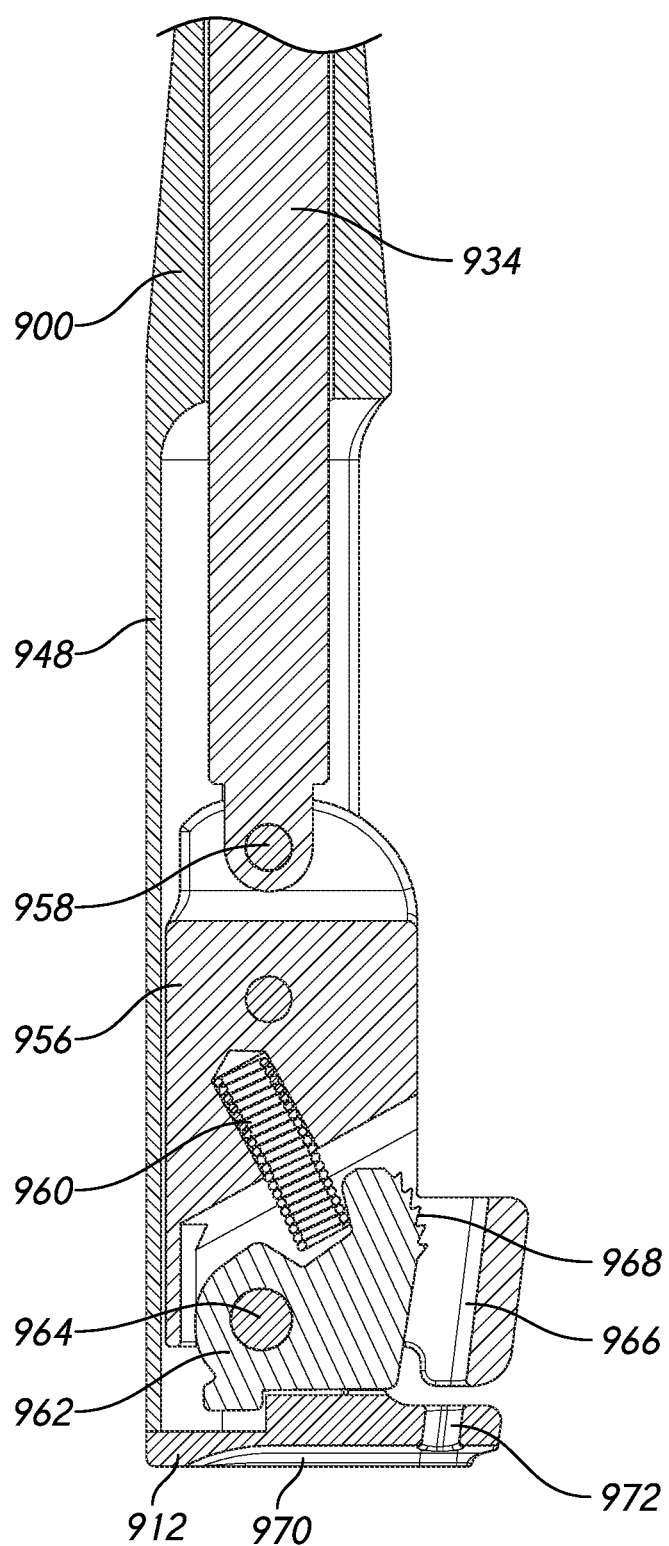
FIG. 63 is a cross-sectional view of a distal portion of the tensioner of FIG. 60 in a first position.
Figure 64:
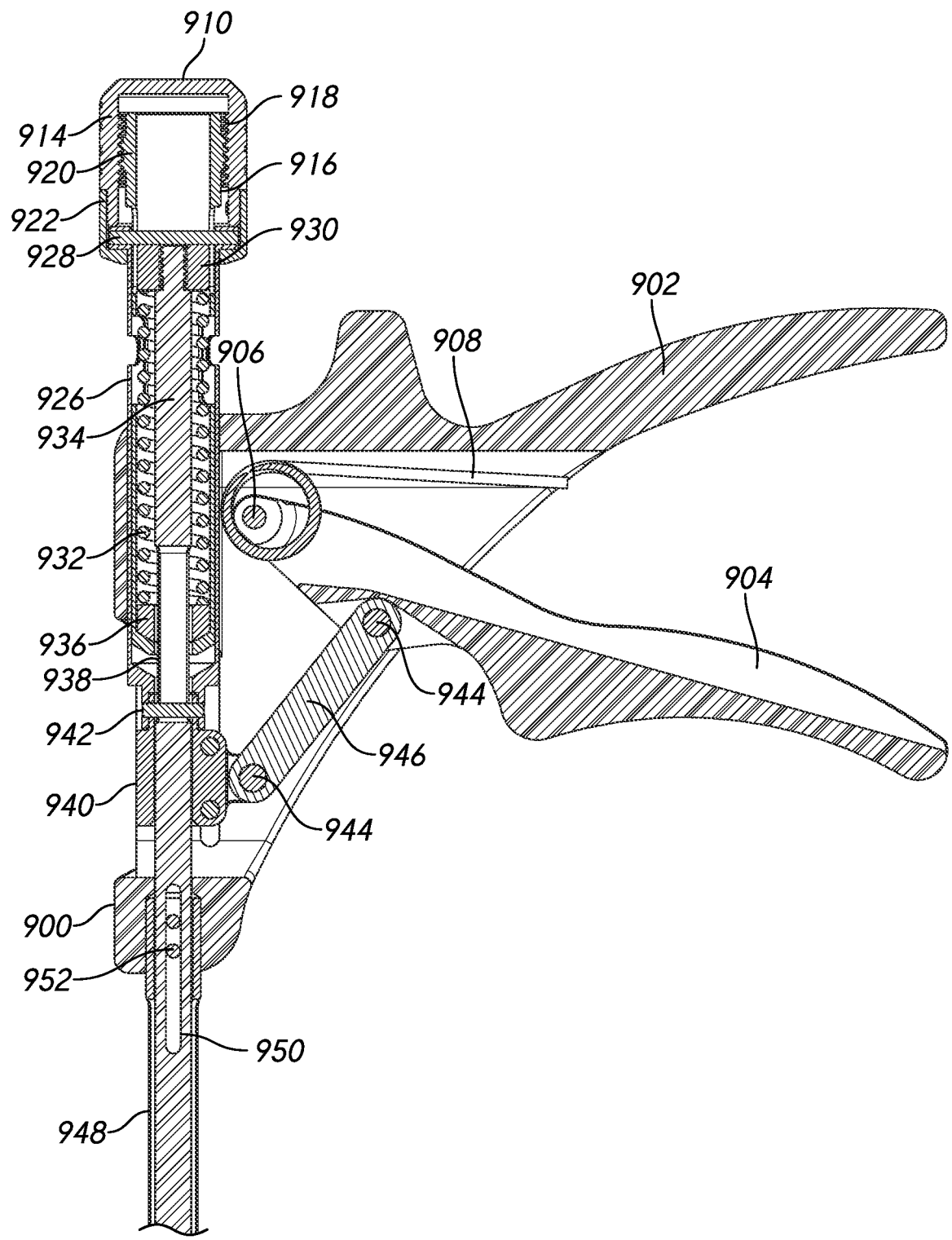
FIG. 64 is a cross-sectional view of a proximal portion of the tensioner of FIG. 60 in the first position.
Figure 65:
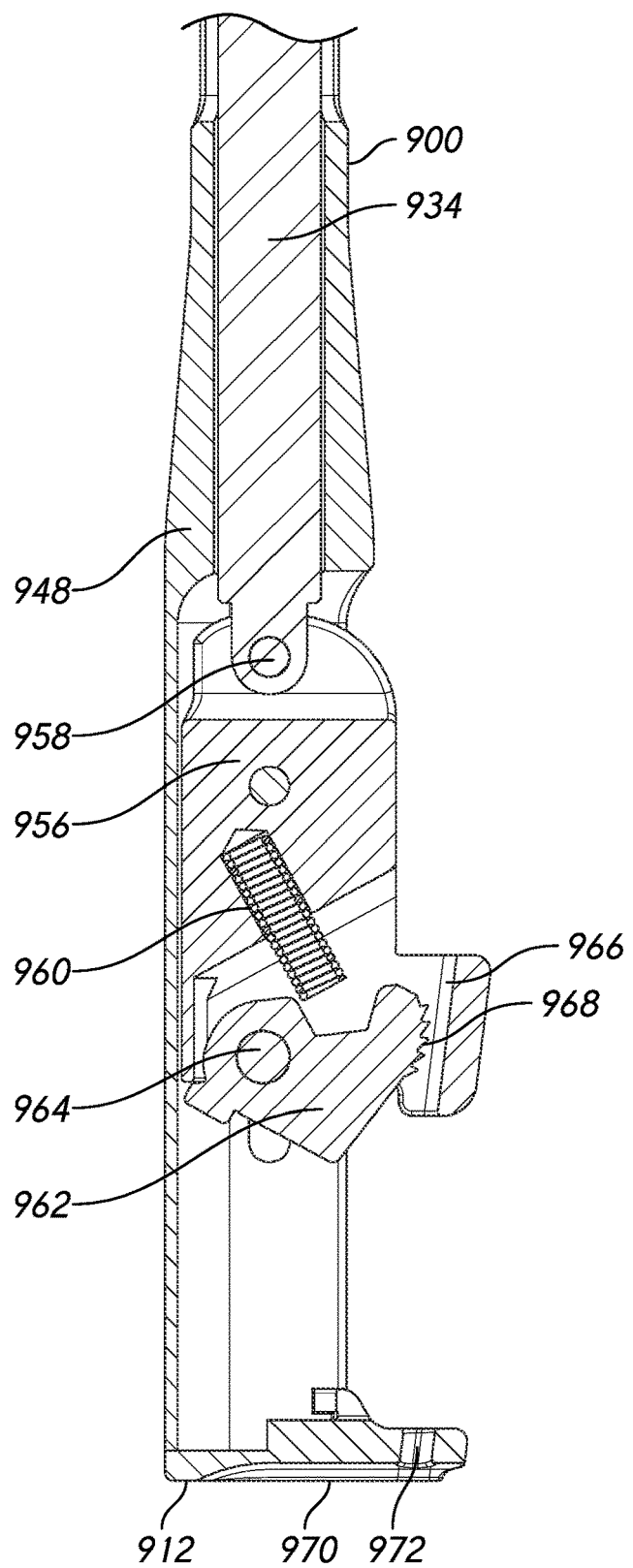
FIG. 65 is a cross-sectional view of a distal portion of the tensioner of FIG. 60 in a second position.
Figure 66:
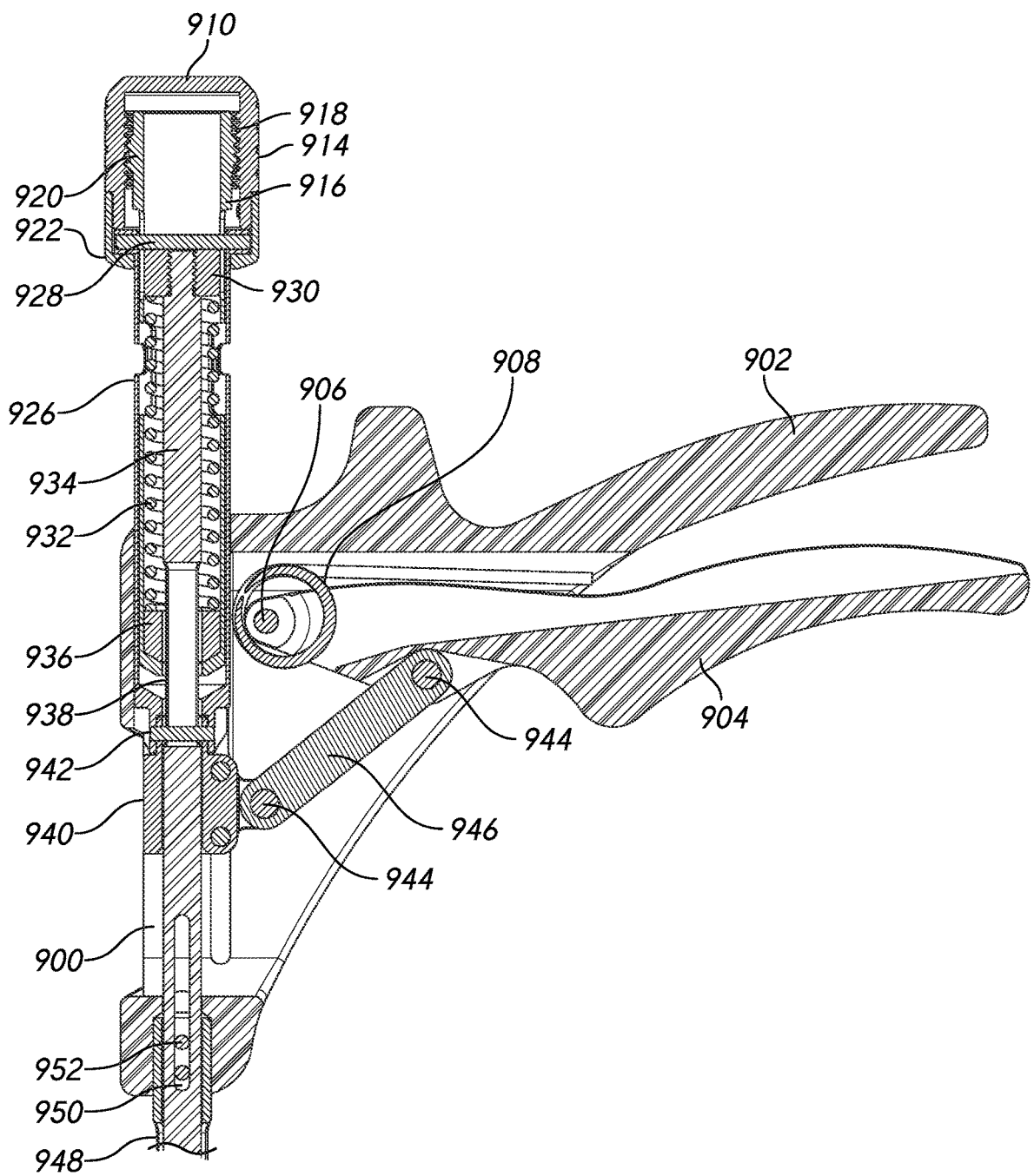
FIG. 66 is a cross-sectional view of a proximal portion of the tensioner of FIG. 60 in the second position.
Figure 67:
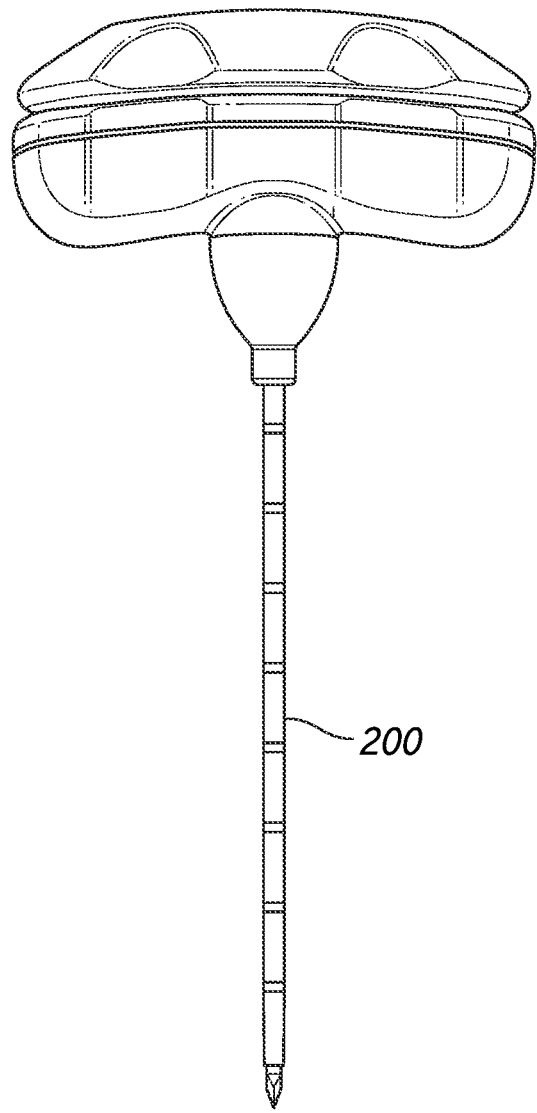

FIGS. 55-66 depict views of components for fusion preparation. FIG. 55 illustrates a perspective view of a guarded flush cutter 800. FIG. 56 illustrates a top view of the guarded flush cutter 800. FIG. 57 illustrates a front view of the guarded flush cutter 800. FIG. 58 illustrates a perspective view of a head pusher 820. FIG. 59 illustrates a view of a distal portion of the head pusher 820. FIG. 60 illustrates a perspective view of a tensioner 900. FIG. 61 illustrates a view of a distal portion of the tensioner 900. FIG. 62 illustrates a view of a proximal portion of the tensioner 900. FIG. 63 illustrates a cross-sectional view of a distal portion of the tensioner 900 in a first position. FIG. 64 illustrates a cross-sectional view of a proximal portion of the tensioner 900 in the first position. FIG. 65 illustrates a cross-sectional view of a distal portion of the tensioner 900 in a second position. FIG. 66 illustrates a cross-sectional view of a proximal portion of the tensioner 900 in the second position. The second position can be a retracted position where tension is applied to the bone tie 100. In some embodiments, the tensioner 900 is held vertically is use. In some embodiments, components of the tensioner 900 are actuated to move from the first position to the second position. In some embodiments, components of the tensioner 900 act under the influence of gravity to move from the second position back to the first position.

The guarded flush cutter 800 can include a first handle 802 and a second handle 804. The guarded flush cutter 800 can include a pivot pin 806. The first handle 802 and the second handle 804 can pivot relative to each other via the pivot pin 806.

The first handle 802 and the second handle 804 can include finger grips 808. The finger grips 808 can facilitate holding or gripping the first handle 752 and the second handle 804. The first handle 802 and the second handle 804 can be biased. The guarded flush cutter 800 can include a spring 810. The spring 810 can be disposed between the finger grips 808 and the pivot pin 806. The spring 810 can bias the first handle 802 and the second handle 804 away from each other.

The first handle 802 can include a first blade 812. The second handle 804 can include a second blade 814. The two blades 812, 814 can be diametrically opposed. The two blades 812, 814 can pinch together. The two blades 812, 814 can cut the bone tie 100. The first handle 802 and the second handle 804 can receive the head 136 of the bone tie 100 therebetween. The head 136 of the bone tie 100 can be severed from the rest of the bone tie 100. The bone tie 100 can be cut at or near the neck section 114.

The guarded flush cutter 800 can include a guard 816. The guard 816 can couple to the first handle 802. The guard 816 can be integrally formed with the first handle 802. The guard 816 can extend toward the second handle 804. The guard 816 can be positioned near the blade 812, 814. The guard 816 can be positioned to the side of the blades 812, 814. The guard 816 can retain the head 136 of the bone tie 100 after the bone tie 100 is cut.

The head pusher 820 can include a head pusher handle 822. The head pusher handle 822 can include finger grips 824. The finger grips 824 can facilitate holding or gripping the head pusher 820. The head pusher 820 can include a head pusher shaft 824. The head pusher shaft 824 can include one or more bends. The head pusher shaft 824 can be offset. The head pusher shaft 824 can be non-coaxial. The head pusher 820 can include a head pusher tip 826. The head pusher tip 826 can be shaped to rest against the anatomy of the patient. The head pusher tip 826 can extend through the portal 300. The head pusher tip 826 can include a lumen 828. The lumen 828 can be shaped to receive a portion of the bone tie 100 therethrough.

The bone tie 100 can include the third section 112 and the neck section 114. The bone tie 100 can include the fastener section 106. The fastener section 106 can be located at or near the proximal end 102. The fastener section 106 can include any mechanism configured to secure the fastener section 106 to another section of the bone tie 100. The fastener section 106 can include a mechanism that allows the bone tie 100 to be secured in a single direction of travel such as a ratchet. The neck section 114 can be passed through the fastener section 106 after the head 136 is removed. The third section 112 can be passed through the fastener section 106 after the head 136 is removed. The second section 110 can be passed through the fastener section 106 after the head 136 is removed. The ratchet 122 can engage the gears 128. The bone tie 100 can form a loop. The bone tie 100 can be tightened to form a smaller loop. The bone tie 100 can pass through the bone lumen before forming the loop. The bone tie 100 can be disposed within the bone lumen as the bone tie 100 is tightened.

The head pusher 820 can engage the bone tie 100 after the loop is formed. The head pusher 820 can engage the bone tie 100 after the head 136 is cut. The head pusher 820 can engage the bone tie 100 after the neck section 114, the third section 112, and/or the second section 110 pass through the lumen 118 of the fastener section 106. The head pusher 820 can engage the bone tie 100 after a loop is formed. The head pusher 820 can engage a free end or tail of the bone tie 100. The neck section 114 can be passed through the lumen 828 of the head pusher 820. The head pusher 820 can allow a distal portion of the bone tie 100 to be pulled through the head pusher 820. The head pusher 810 can tension the bone tie 100. The head pusher 820 can be pushed downward along the bone tie 100 to tension the bone tie 100. The head pusher 820 can be pushed downward along the bone tie 100 to form a smaller loop. The head pusher 820 can slide along the free end of the bone tie 100 after the loop is formed. The head pusher 820 can provisionally tension the bone tie 100.

In some embodiments, the head pusher 820 can be used in combination with the portal 300. The head pusher 820 can extend through the second passageway 340. The head pusher tip 826 can be shaped to correspond with a portion of the second passageway 340. The head pusher tip 826 can abut the second side 332. The portal 300 can prevent rotation of the head pusher tip 826 relative to the portal 300. In other embodiments, the portal 300 can be removed before using the head pusher 810.

The tensioner 900 can apply tension to the bone tie 100 to form a smaller loop. The tensioner 900 can include a tensioner handle 902. The tensioner 900 can include a pivoting handle 904. The tensioner handle 902 can include finger grips. The pivoting handle 904 can include finger grips. The tensioner handle 902 and the pivoting handle 904 can be configured to be grasped by the user to actuate the tensioner 900. The pivoting handle 904 can be configured to pivot relative to the tensioner handle 902. The tensioner 900 can include a handle pivot pin 906. The pivoting handle 904 can pivot relative to the handle pivot pin 906. The tensioner 900 can include a torsion spring 908. The torsion spring 908 can bias the pivoting handle 904 outward relative to the tensioner handle 902. The user can grasp the pivoting handle 904 and bring the pivoting handle 904 toward the tensioner handle 902 to move from the first position to the second position. The first position can be a neutral position. The second position can be an actuated position. The user can compress the torsion spring 908 as shown in FIG. 66.

The tensioner 900 can include a proximal end 910 and a distal end 912. The tensioner 900 can include a series of components in axial alignment. The tensioner 900 can include a series of components configured to move proximally and distally to tension the bone tie 100. The tensioner 900 can include a tension adjuster cap 914. The proximal end 910 can include the tension adjuster cap 914. The tensioner 900 can include a spring sleeve 916. The tension adjuster cap 914 can include a threaded bore 918. The spring sleeve 916 can include a threaded portion 920. The tension adjuster cap 914 can be configured to engage the spring sleeve 916. The threaded bore 918 of the tension adjuster cap 914 can engage the threaded portion 920 of the spring sleeve 916. The tension adjuster cap 914 can be rotated to move the spring sleeve 916 relative to the tension adjuster cap 914. The tensioner 900 can include a tension cap hub 922. The tension cap hub 922 can be coupled to the tension adjuster cap 914. The tensioner 900 can include the tension indicator pin 924. The tension indicator pin 924 can couple the tension adjuster cap 914, tension cap hub 922, and the spring sleeve 916.

The tensioner 900 can include a spring housing 926. The tensioner 900 can include a tension shaft stop pin 928. The tension shaft stop pin 928 can couple the spring housing 926 and the spring sleeve 916. The tension shaft stop pin 928 can be configured to translate proximally and distally depending on the relative position of the spring housing 926 and the spring sleeve 916. The tensioner 900 can include a tension shaft stop 930. The tension shaft stop 930 can be configured to abut the tension shaft stop pin 928. The tensioner 900 can include a tension spring 932. The tension spring 932 can be disposed within the spring sleeve 916. The tension shaft stop 930 can be disposed within the spring sleeve 916. The tension shaft stop 930 can abut the tension shaft stop pin 928 under the influence of the tension spring 932. The tension shaft stop 930 can abut the tension shaft stop pin 928 when the tension spring 932 is fully extended. The tension shaft stop 930 can move distally from tension shaft stop pin 928 when the tension spring 932 is compressed. The tensioner 900 can include a central shaft 934. The central shaft 934 can extend the length of the tensioner 900, or a portion thereof. The central shaft 934 can be connected to the tension shaft stop 930. The tensioner 900 can include a washer 936. The tension spring 932 can extend in the space from the washer 936 to the tension shaft stop 930. The movement of the tension shaft stop 930 toward the washer 936 can compress the tension spring 932. The central shaft 934 can extend through the washer 936. The central shaft 934 can include a slot 938. The tensioner 900 can include a tensioner hub 940. The tensioner 900 can include a hub pin 942. The hub pin 942 can be disposed within the slot 938. The hub pin 942 can translate proximally and distally within the slot 938. The hub pin 942 can extend through the tensioner hub 940. The hub pin 942 can extend through the spring housing 926. The tensioner 900 can include one or more linkage pins 944. The tensioner 900 can include a linkage 946. The one or more linkage pins 944 can couple the linkage 946 with the tensioner hub 940 and the pivoting handle 904. The tensioner 900 can include an outer shaft 948. The central shaft 934 can be disposed within the outer shaft 948. The central shaft 934 can include a transverse slot 950. The tensioner 900 can include one or more inner shaft slot pins 952. The outer shaft 948 can be coupled to the tensioner handle 902 via one or more inner shaft slot pins 952. The central shaft 934 can slide relative to the one or more inner shaft slot pins 952 via the transverse slot 950. The outer shaft 948 can include a distal slot 954.

The tensioner 900 can include a puller 956. The tensioner 900 can include one or more puller pins 958. The puller 956 can be coupled to the central shaft 934 via one or more puller pins 958. The puller 956 can be coupled to the outer shaft 948 via one or more puller pins 958. The one or more puller pins 958 can slide proximally and distally relative to the outer shaft 948 via the distal slot 954. The tensioner 900 can include a ratchet spring 960. The puller 956 can slide distally under the influence of gravity in the first position. The ratchet spring 960 can be neutral. The ratchet spring 960 can allow the bone tie 100 to be loaded into the puller 956. The tensioner 900 can include a ratchet body 962. The ratchet spring 960 can bias the ratchet body 962. The ratchet body 962 can compress the ratchet spring 960. The tensioner 900 can include a ratchet pin 964. The ratchet body 962 can pivot relative to the ratchet pin 964. The puller 956 can include a passageway 966. The passageway 966 can be sized to receive the bone tie 100. The gears 128 of the bone tie 100 can face toward the ratchet body 962 when the bone tie 100 is received within the passageway 966. The ratchet body 962 can include one or more ratchets 968. The ratchet body 962 can swing to open the passageway 966. The ratchet body 962 can swing to disengage the bone tie 100. The ratchet 968 can engage the gear 128 of the bone tie 100 when the tensioner 900 in actuated. The ratchet 968 can engage the gear 128 of the bone tie 100 when the puller 956 moves proximally. The ratchet 968 can engage the gear 128 of the bone tie 100 when the ratchet spring 960 is extended. The ratchet 968 can engage the gear 128 of the bone tie 100 when the ratchet body 962 swings into engagement with the bone tie 100. The tensioner 900 can include a tensioner tip 970. The tensioner tip 970 can include a lumen 972. The lumen 972 can receive the bone tie 100. The tensioner tip 972 can be coupled to the outer shaft 948. The distal end 912 can include the tensioner tip 970. The puller 956 can slide distally relative to the tensioner tip 970 under the influence of gravity. The puller 956 can slide distally relative to the tensioner tip 970 when the tensioner 900 is not actuated. The puller 956 can slide distally relative to the tensioner tip 970 thereby disengaging the ratchet 968 and the gear 128.

The tensioner tip 970 can engage the bone tie 100 after a loop is formed. The free end of the bone tie 100 can be passed through the lumen 972 of the tensioner tip 970. The tensioner tip 970 can slide along the bone tie 100 toward the fastener section 106 of the bone tie 100. The tensioner tip 970 can be shaped to receive the fastener section 106 of the bone tie 100. The tensioner tip 970 can engage the fastener section 106 of the bone tie 100. The tensioner tip 970 can be positioned against the pedicle. The free end of the bone tie 100 can be passed through the passageway 966 of the puller 956. The ratchet body 962 can be disposed within the puller 956. The free end of the bone tie 100 can be passed through the passageway 966 of the puller 956. The bone tie 100 can freely slide through the puller 956. The ratchet body 962 swings to maximize the passageway 966 to accept the bone tie 100. The ratchet body 962 can include a stop that facilitates the positioning of the ratchet body 962 against the tensioner tip 970. The ratchet body 962 freely slides over the bone tie 100. The bone tie 100 can slide through the puller 956 freely in one direction, but can be prevented from sliding in the opposite direction. The tensioner 900 can be positioned with the tensioner tip 970 against the fastener section 106. The tensioner 900 can be positioned with the free end of the bone tie 100 through the lumen 972 of the tensioner tip 970 and the passageway 966 of the puller 956.

In some methods, the user can advance the bone tie 100 through the puller 956 by pulling the free end of the bone tie 100. In some methods, the user can advance the bone tie 100 through the puller 956 through actuation of the pivoting handle 904. The ratchet body 962 is biased out of engagement with the gears 128 of the bone tie 100 in the first position. The ratchet body 962 is biased by the ratchet spring 960. The bone tie 100 can be easily loaded through the lumen 972 of the tensioner tip 970 and the passageway 966 of the puller 956. The puller 956 is in the first position under the influence of gravity at shown in FIG. 63.

The pivoting handle 904 can be squeezed toward the tensioner handle 902 as shown in FIG. 66. The pivoting handle 904 can pivot relative to the pivot pin 906. The pivoting handle 904 can compress the torsion spring 908. The pivoting handle 904 can be pulled toward the proximal end 910. The pivoting handle 904 can pull the linkage 946. The linkage 946 can connect the pivoting handle 904 and the tensioner hub 940 via linkage pins 944. The pivoting handle 904 can pull the tensioner hub 940 proximally. The tensioner hub 940 moves the spring housing 926 proximally. The spring housing 926 moves the tension cap hub 922 and the tension adjuster cap 914 proximally. The tension cap hub 922 and the tension adjuster cap 914 move the spring sleeve 916 proximally. The spring sleeve 916 moves the central shaft 934 proximally if the tension is less than tension applied by the tension spring 932. The compression of the pivoting handle 904 can cause the proximal movement of tensioner hub 940, the spring housing 926, the tension cap hub 922, the tension adjuster cap 914, and the spring sleeve 916. The central shaft 934 can move proximally with the tensioner hub 940 until an amount of tension applied to the bone tie 100 overcomes the tension of the tension spring 932, as described herein. The pivoting handle 904 can pull the central shaft 934 proximally as shown in FIGS. 65 and 66.

The pivoting handle 904 can pull the puller 956 proximally. The puller 956 can be connected to the central shaft 934. The puller 956 can move proximally with the tensioner hub 940 until an amount of tension applied to the bone tie 100 overcomes the tension of the tension spring 932, as described herein. The pivoting handle 904 can pull the ratchet body 962 proximally. The ratchet body 962 can swing relative to the ratchet pin 964. The ratchet body 962 can extend the ratchet spring 960. The one or more ratchets 968 of the ratchet body 962 can engage with one or more gears 128 during the proximal movement of the puller 956. The puller 956 can move proximally while the tensioner tip 970 remains against the fastener section 106. The puller 956 can slide proximally relative to the outer shaft 948. The puller 956 can slide proximally relative to the tensioner handle 902. The pivoting handle 904 can pull the puller 956 and the free end of the bone tie 100 proximally. As the free end of the bone tie 100 is pulled proximally by the puller 956, the loop of the bone tie 100 becomes smaller. The one or more ratchets 968 can be pulled proximally, thus pulling the gears 128 of the bone tie 100 proximally. The tensioner 900 can make the loop of the bone tie 100 smaller by actuation of the pivoting handle 904. The pivoting handle 904 can tension the bone tie 100.

The pivoting handle 904 can be released. The pivoting handle 904 can pivot relative to the pivot pin 906. The torsion spring 908 can pivot the pivoting handle 904 distally. The pivoting handle 904 can assume a neutral configuration as shown in FIG. 64. The pivoting handle 904 can be biased toward the distal end 912 by the torsion spring 908. The release of the pivoting handle 904 can move the linkage 946. The linkage 946 can connect the pivoting handle 904 and the tensioner hub 940 via linkage pins 944. The release of the pivoting handle 904 can move the tensioner hub 940 distally. The release of the pivoting handle 904 can move the central shaft 934 distally. The release of the pivoting handle 904 can move the puller 956 distally. In use, the tensioner can be held vertically. The release of the pivoting handle 904 can allow the central shaft 934 to move distally under the influence of gravity. The release of the pivoting handle 904 can allow the puller 956 to move distally under the influence of gravity. The release of the pivoting handle 904 can allow the ratchet body 962 to move distally under the influence of gravity. The ratchet body 962 can abut the inside surface of the tensioner 900, thereby pivoting the ratchet body 962 out of engagement with the bone tie 100. The ratchet body 962 can be pivoted to release the bone tie 100. The release of the pivoting handle 904 can advance the puller 956 relative to the bone tie 100. The one or more ratchets 968 can disengage one or more gears 128 during distal movement. The ratchet body 962 can be biased distally, thus realigning the one or more ratchets 968 with additional gears 128 of the free end of the bone tie 100. The release of the pivoting handle 904 does not change the size of the loop of the bone tie 100 which is maintained by the fastener section 106 and the gears 128. The release of the pivoting handle 904 can adjust the position of the puller 956 relative to the free end of the bone tie 100. The puller 956 can move distally while the tensioner tip 970 remains against the fastener section 106. The puller 956 can slide distally relative to the outer shaft 948 upon the release of the pivoting handle 904. The puller 956 slides distally relative to the free end of the bone tie 100 upon the release of the pivoting handle 904.

The pivoting handle 904 can be squeezed toward the tensioner handle 902 again as shown in FIG. 66. The pivoting handle 904 can move the puller 956 proximally via the central shaft 934 and the tensioner hub 940. The pivoting handle 904 can move the ratchet body 962 proximally. The proximal movement of the ratchet body 962 can allow the ratchet body 962 to swing relative to the ratchet pin 964. The ratchet body 962 can swing into engagement with gears 128 of the bone tie. The ratchet body 962 can swing into the passageway 968. The ratchet body 962 can extend the ratchet spring 960. The pivoting handle 904 can move the bone tie 100 proximally with the puller 956 to further tension the bone tie 100. The one or more ratchets 968 can be moved proximally, thus pulling the gears 128 of the bone tie 100 proximally.

In some methods, an equilibrium is reached between the tension of the tension spring 932 and the tension between the ratchet body 962 and the bone tie 100. The tension between the ratchet body 962 and the bone tie 100 can compress the tension spring 932. The central shaft 934 moves proximally with the tensioner hub 940 until the tension of the bone tie 100 overcomes the tension of the tension spring 932. The tension shaft stop 930 of the central shaft 934 can move distally under the applied tension between the ratchet body 962 and the bone tie 100. The tension shaft stop 930 of the central shaft 934 can move distally as it becomes more difficult to tension the bone tie 100. The tension shaft stop 930 of the central shaft 934 can move distally to compress the tension spring 932 under the applied tension of the bone tie 100. The force needed to pull the ratchet body 962 and the bone tie 100 can be greater than the force of the tension spring 932. The tension spring 932 can compress when it becomes difficult to further tighten the bone tie 100. The pivoting handle 904 can make the loop of the bone tie 100 smaller through actuation of the pivoting handle 904. The pivoting handle 904 can tension the bone tie 100. The pivoting handle 904 can be sequentially squeezed and released to tension the bone tie 100. The pivoting handle 904 can be squeezed to engage and pull the bone tie 100 proximally. The pivoting handle 904 can be released to adjust the puller 956 relative to the bone tie 100 so that further tension can be applied.

The tensioner 900 can be adjustable to vary the tension applied by the tensioner 900 to the bone tie 100. The tension adjuster cap 914 can be rotated clockwise or counterclockwise. The tension adjuster cap 914 can be rotated clockwise to increase the tension. The tension adjuster cap 914 can be rotated counterclockwise to decrease the tension. The tension adjuster cap 914 can be rotated to change the location of the spring sleeve 916 relative to the tension cap 914. The tension adjuster cap 914 can be rotated clockwise to move the spring sleeve 916 proximally. The tension adjuster cap 914 can be rotated counterclockwise to move the spring sleeve 916 distally. The spring sleeve 916 can include the threaded portion 920. The tension adjuster cap 914 can include the corresponding threaded bore 918. The rotation of the tension adjuster cap 914 can move the threaded portion 920 relative to the threaded bore 918. The spring sleeve 916 surrounds the tension spring 932. The spring sleeve 916 moves the washer 936 relative to the tension shaft stop 930. The spring sleeve 916 compresses the tension spring 932 by moving the washer 936 relative to the tension shaft stop 930. The amount of tension applied by the tensioner 900 can be adjusted by adjusting the tension applied by the tension spring 932. The tension applied by the tension spring 932 can be determined by the effective length of the tension spring 932 within the spring housing 926. The length of the tension spring 932 can be adjusted by rotating the tension adjuster cap 914 which moves the spring sleeve 916 to lengthen or shorten the effective length of the tension spring 932. The length of the tension spring 932 can be adjusted by moving the washer 936 relative to the tension shaft stop 930. The tension spring 932 can adjust the tension applied by the puller 956. The puller 956 will apply tension until the amount of tension applied by the bone tie 100 overcomes the amount of tension applied by the tension spring 932, thus moving the tension shaft stop 930 distally. The relative location of the tension shaft stop 930 can indicate whether the amount of tension applied by the bone tie 100 overcomes the amount of tension applied by the tension spring 932. The relative location of the tension shaft stop 930 can be viewed by the user. The effective length of the tension spring 932 can be adjusted during the method of use. The tension adjuster cap 914 can be coupled to the tension cap hub 922. The spring sleeve 916 can be disposed within and coupled with the tension adjuster cap 914 and the tension cap hub 922. The location of the spring sleeve 916 relative to the tension adjuster cap 914 and the tension cap hub 922 can determine the effective length of the tension spring 932.

The spring housing 926 can extend from the tensioner hub 940 to the spring sleeve 916. The spring housing 926 can be coupled to the tension shaft stop pin 928 at a proximal end. The spring housing 926 can be coupled to the hub pin 942 at a distal end. The spring housing 926 can be a fixed length between the tensioner hub 940 and the spring sleeve 916. The tension shaft stop pin 928 can slide relative to the spring sleeve 916. The tension shaft stop pin 928 can slide to adjust the tension of the tension spring 932. The tension shaft stop pin 928 abuts the tension shaft stop 930. The tension shaft stop 930 can be coupled to the central shaft 934. The distal end of the tension spring 932 can be coupled to the washer 936. The washer 936 can be disposed within the distal end of the spring sleeve 916. The hub pin 942 can move proximally and distally within the slot 938.

The pivoting handle 904 can be squeezed toward the tensioner handle 902. The pivoting handle 904 can pull the linkage 946. The linkage 946 can connect the pivoting handle 904 and the tensioner hub 940 via linkage pins 944. The pivoting handle 904 can pull the tensioner hub 940 proximally. The tensioner hub 940 can pull the spring housing 926 proximally. The tensioner hub 940 can pull the tension adjuster cap 914 proximally. The tensioner hub 940 can pull the spring sleeve 916 proximally. The tensioner hub 940 can pull the washer 936 proximally. The tensioner hub 940 can pull the central shaft 934 proximally, depending on the relative tension between the bone tie 100 and the tension spring 932. The central shaft 934 moves proximally with the tensioner hub 940 as the tensioner hub 940 moves proximally until an amount of tension applied to the bone tie 100 overcomes the tension of the tension spring 932.

The bone tie 100 forms a smaller loop. As the bone tie forms a smaller loop, the bone tie 100 exerts a tension on the puller 956 and the central shaft 934. There may be a need for increased tension to further tighten the bone tie 100. The central shaft 934 is coupled to the puller 956 and the tension shaft stop 930. The tension shaft stop 930 and the central shaft 934 may move distally under increased tension applied by the bone tie 100. The tension needed to pull the gear 128 proximally may compress the tension spring 932. The central shaft 934 may move distally under the applied tension of the bone tie 100. The tension shaft stop 930 may move distally under the applied tension of the bone tie 100. The tension shaft stop 930 may compress the tension spring 932. The distance that the tension shaft stop 930 moves may correspond to the amount of tension that the ratchet body 962 provides to the bone tie 100. The tension shaft stop 930 may move distally as the tensioner 900 applies more tension to the bone tie 100.

The tensioner 900 can include one or more visual indicators for the amount of tension applied. The spring housing 926 can include a first opening 976. The user can view the tension spring 932 through the first opening 976 under low tension. The user can view the central shaft 934 through the first opening 976 under low tension. The tension shaft stop 930 can align with the first opening 976 in the spring housing 926 when the central shaft 934 moves distally under increased tension by the bone tie 100. The tension shaft stop 930 can align with the first opening 976 when the desired tension is reached.

The spring housing 926 can include a second opening 978. The user can view the spring sleeve 916 through the second opening. The spring sleeve 916 can move proximally and distally when the tension adjuster cap 914 is rotated. The spring sleeve 916 can include a marking 980. The spring housing 926 can have indicators 982 as shown in FIG. 62. The indicators 982 can indicate high tension and low tension. The indicators 982 can provide an indicator of tension. The indicators lines 982 can provide an indicator of the effective length of the tension spring 932. The indicator line 982 can indicate low tension of the tension spring 932. The indicator line 982 can indicate medium tension of the tension spring 932. The indicator line 982 can indicate high tension of the tension spring 932. The marking 980 of the spring sleeve 916 can align with one of the indicator lines 982 of the spring housing 926. The tension adjuster cap 914 rotates to move the spring sleeve 916 and the marking 980 proximally to increase the tension. The tension adjuster cap 914 rotates to move the spring sleeve 916 and the marking 980 distally to decrease the tension. The marking 980 of the spring sleeve 916 can indicate the level of compression of the tension spring 932. The marking 980 of the spring sleeve 916 can indicate the amount of tension that the tension spring 932 can impart on the bone tie 100. The tension shaft stop 930 can align with the first opening 976 when the indicated tension of the marking 980 is reached.

The pivoting handle 904 can be sequentially squeezed and released to tension the bone tie 100. The bone tie 100 can be tensioned with the movement of the central shaft 934 and the puller 956 relative to the bone tie 100 The ratchet body 962 of the puller 956 pulls the free end of the bone tie 100 proximally. The loop decreases in size. The tension adjuster cap 914 can be rotated to the desired tension. The marker 980 of the spring sleeve 916 can align with the low tension indicator line 982. The tension adjuster cap 914 can be rotated to increase the tension. The marker 980 of the spring sleeve 916 can align with the medium tension indicator line 982. The tension adjuster cap 914 can be rotated to increase the tension. The marker 980 of the spring sleeve 916 can align with the high tension indicator line 982. The user can view the tension spring 932 through the first opening 976. The user can view the central shaft 934 through the first opening 976.

The pivoting handle 904 can be sequentially squeezed and released. The central shaft 934 can experience tension from the bone tie 100 when the one or more ratchets 968 engages the gears 128. The central shaft 934 can be pulled distally under the tension from the bone tie 100. The tension shaft stop 930 can align with the first opening 976 due to the distal movement of the central shaft 934 by the bone tie 100 when the desired tension is reached.

The tension adjuster cap 914 can be rotated to increase the tension during the method of use. The user can view the central shaft 934 through the first opening 976 when the tension is increased. The pivoting handle 904 can be sequentially squeezed and released. The tension shaft stop 930 can align with the first opening 976 when the increased tension is reached.

10. Method

FIGS. 67-84 depict methods. The systems and methods can be utilized for a percutaneous approach. The systems and methods can be used for any approach. One or more method steps can be optional. One or more component or tool can be optional. One or more method step can be performed in a different order. The method can include any sequence of steps.

The method can include positioning. The method can include targeting. The method can include access. The method can include placing the patient in a prone position. The method can include positioning the JAMSHIDI needle 200 shown in FIG. 67. The JAMSHIDI needle 200 can be inserted about 2.5 cm deep. The JAMSHIDI needle 200 can be inserted into the pedicle. The JAMSHIDI needle 200 can be inserted at the target level. The inner trocar 204 of the JAMSHIDI needle 200 can be removed.

Figure 68:
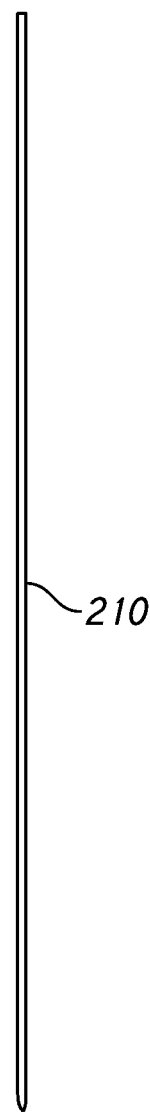

The method can include positioning the k-wire 210 shown in FIG. 68. The k-wire 210 can be inserted into the cannulation of the JAMSHIDI needle 200. The k-wire 210 can be advanced deeper in the pedicle relative to the tapered cutting edge 202 of the JAMSHIDI needle 200. The k-wire 210 can be advanced deeper than the JAMSHIDI needle 200 by 5 mm, 6 mm, 7 mm, 8 mm, 9 mm, 10 mm, or any range of two of the foregoing values. The JAMSHIDI needle 200 can be removed. The k-wire 210 can be left in place. The incision can be made. The incision can be a 35-40 mm facial incision over the facet joint of the target level.

Figure 69:
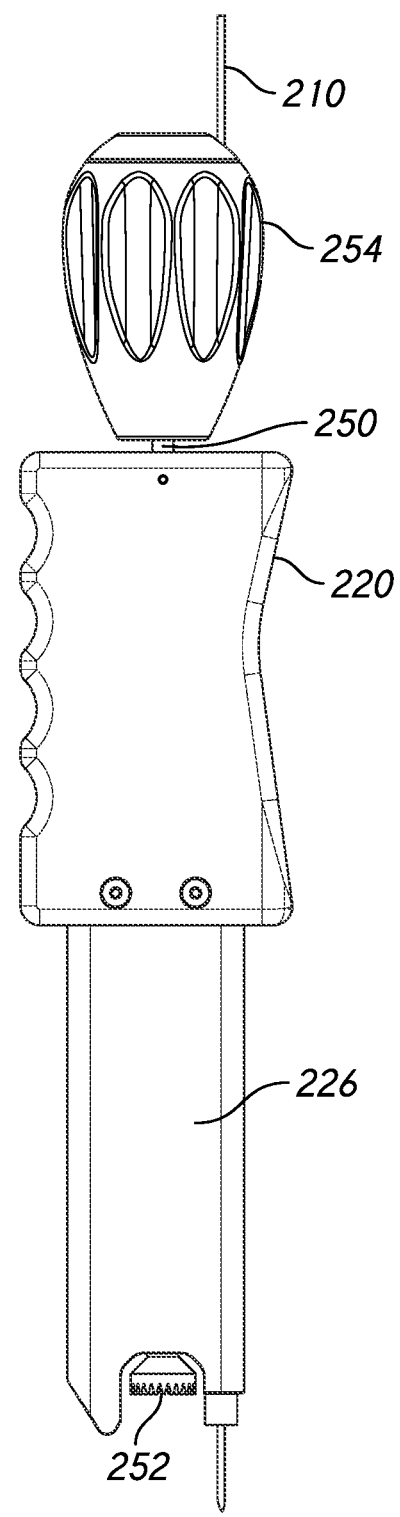

The method can include preparing the facets. The method can include preparing the hypertrophic facets. The method can include positioning the trephine 220 relative to the k-wire 210 as shown in FIG. 69. The trephine shaft 250 can include the trephine blade 252. The trephine shaft 250 can be inserted into the trephine body 226. The trephine shaft 250 can be inserted into the trephine body 226 until it clicks into place. The shaft lock 260 can engage the engagement section 266 of the trephine shaft 250. The shaft lock 260 can provide tactile feedback that the trephine shaft 250 is engaged to the trephine body 226. The trephine shaft handle 254 can be coupled to the trephine shaft 250. The trephine shaft handle 254 can be an AO palm handle. The trephine shaft handle 254 can be attached to the top of the trephine shaft 250. The trephine 220 can be inserted over the k-wire 210. The trephine 220 can be inserted into the incision. The trephine 220 can be seated against the anatomy of the patient. The trephine 220 can be rotated to seat the trephine blade 252 on the facet joint. The trephine shaft handle 254 can be rotated back and forth until the bottom of the trephine body 226 rests on the pedicle and lamina. The trephine 220 can be removed. The k-wire 210 can be left in place.

Figure 70:
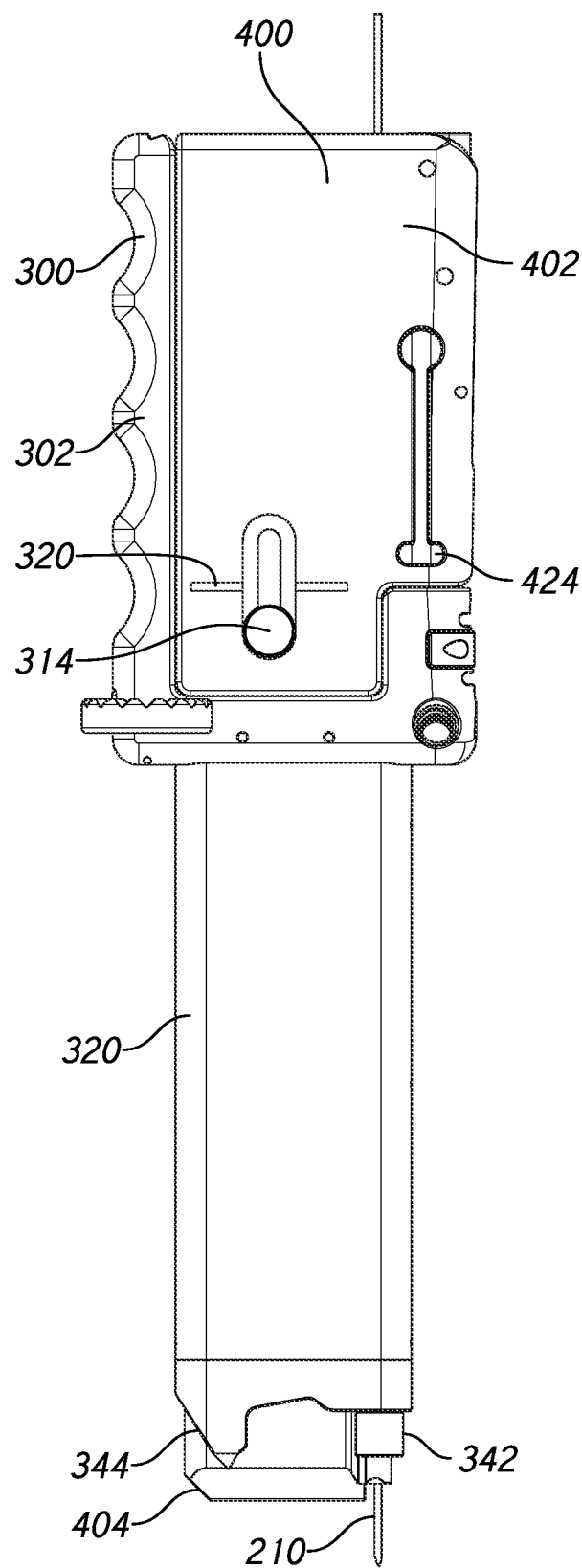

The method can include coupling the portal 300 and the tissue splitter 400. The method can include positioning the portal 300 and the tissue splitter 400 relative to the k-wire 210 as shown in FIG. 70. The method can include inserting the tissue splitter 400 into the portal 300 until the tissue splitter 400 locks into place. The latch arms 424 of the tissue splitter 400 can engage the portal handle 302. The blade 404 can extend through the portal body 320. The tissue splitter 400 and the portal 300 can be inserted over the k-wire 210. The k-wire 210 can extend through the blade 404 of the tissue splitter 400. The k-wire 210 can extend through the tissue splitter handle 402 of the tissue splitter 400.

The tissue splitter 400 and the portal 300 can be inserted into the incision. The tissue splitter 400 and the portal 300 can be inserted until the tissue splitter 400 and the portal 300 bottoms out on the pedicle. The tissue splitter 400 and the portal 300 can be rotated over the facet joint until the ledge 344 can seat on the lamina of the target level. The guide 342 can engage the bored hole formed by the JAMSHIDI needle 200. The blade 404 can retract within the tissue splitter handle 402. The indicator 414 can align with the marking 420 when the blade 404 is fully retracted. The indicator 414 can indicate that a sufficient distance of bone is available to form a lumen. The blade 404 can retract upon downward motion of the portal 300 and the tissue splitter 400. The portal 300 can seat against the bone. The tissue splitter 400 can be removed. The portal 300 can be left in place. The k-wire 210 can be left in place.

Figure 71:
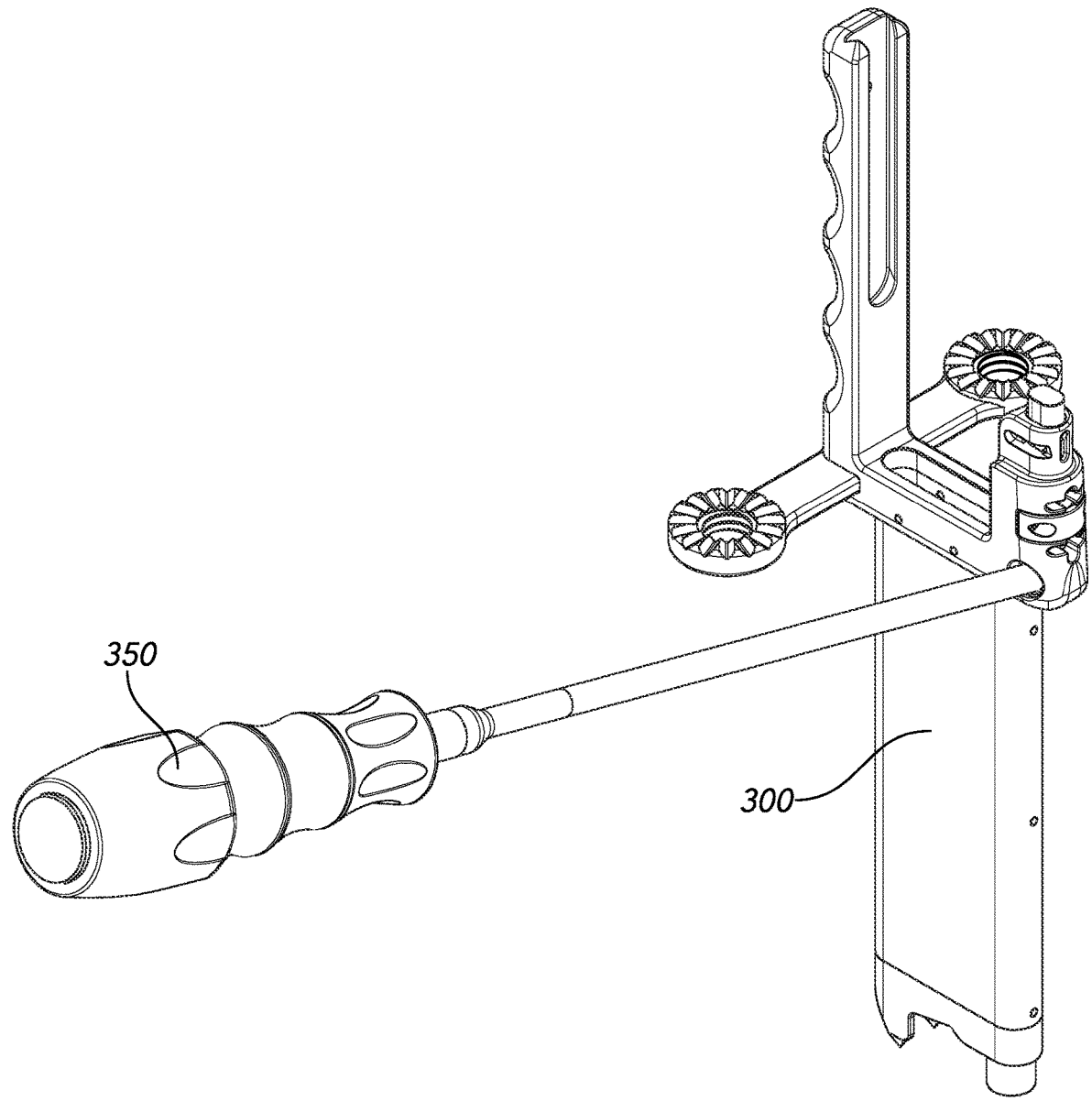

The method can include confirming the position of the portal 300. FIG. 71 illustrates the offset handle 350. The offset handle 350 can be threaded into the threaded opening 346 of the portal 300. The offset handle 350 can be threaded into the portal 300 to facilitate intraoperative imaging. The offset handle 350 can be threaded into the portal 300 to keep the hands of the user out of a C-Arm shot. The user can take A/P and lateral images to confirm the portal 300 is in the correct position. The k-wire 210 can remain in position relative to the portal 300.

Figure 72:
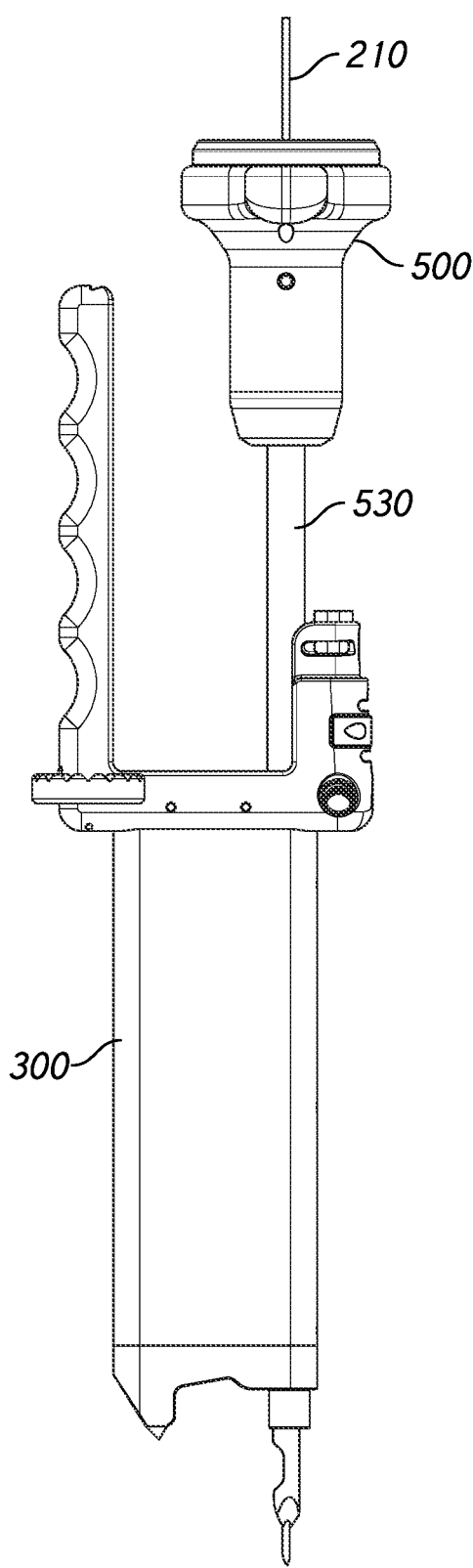
Figure 73:
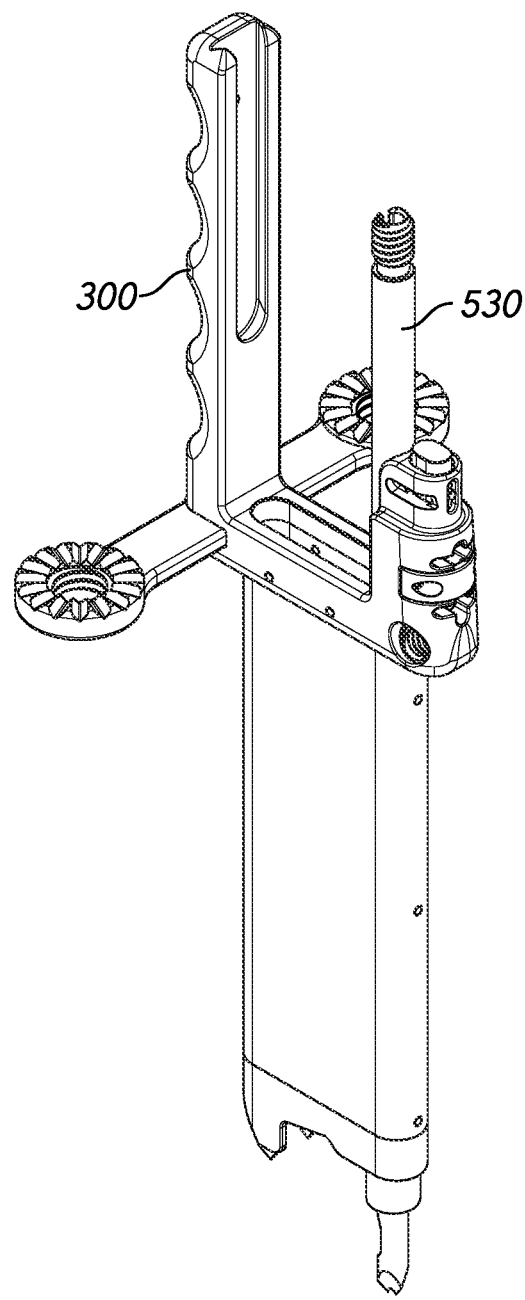

The method can include impacting the awl 530. The awl handle 500 and the awl 530 can be coupled. The awl handle shaft 514 can slide relative to the awl 530, as described herein. The sliding feature 516 and the corresponding sliding feature 540 can engage, as described herein. The T-shaped handle 502 can rotate relative to the awl 530 to engage the threaded portion 536 of the awl 530 with the threaded bore 508 of the awl handle 500, as described herein. The awl handle 500 and the awl 530 can slide over the k-wire 210 and through the portal 300 as shown in FIG. 72. The proximal surface of the awl handle 500 can be impacted. The awl handle 500 can include an impaction cap 510. The impaction cap 510 can be struck with a mallet to advance the awl into the pedicle. The awl 530 can advance until the awl 530 bottoms out. The latch 310 in the portal 300 can engage the pocket 560 in the awl 530. The portal 300 engages the awl 520 to orient the retriever portion 546 toward the lamina. The offset handle 350 can be removed from the portal 300. The table arm can be attached to the portal 300. The portal 300 can include one or more mount inserts 308. The table arm can be coupled to one of the mount inserts 308. The table arm can provide additional stability for the portal 300. The awl handle 500 can be removed. The k-wire 210 can be removed. The portal 300 can be left in place. The awl 530 can be left in place. The portal 300 and the awl 530 are shown in FIG. 73.

Figure 74:
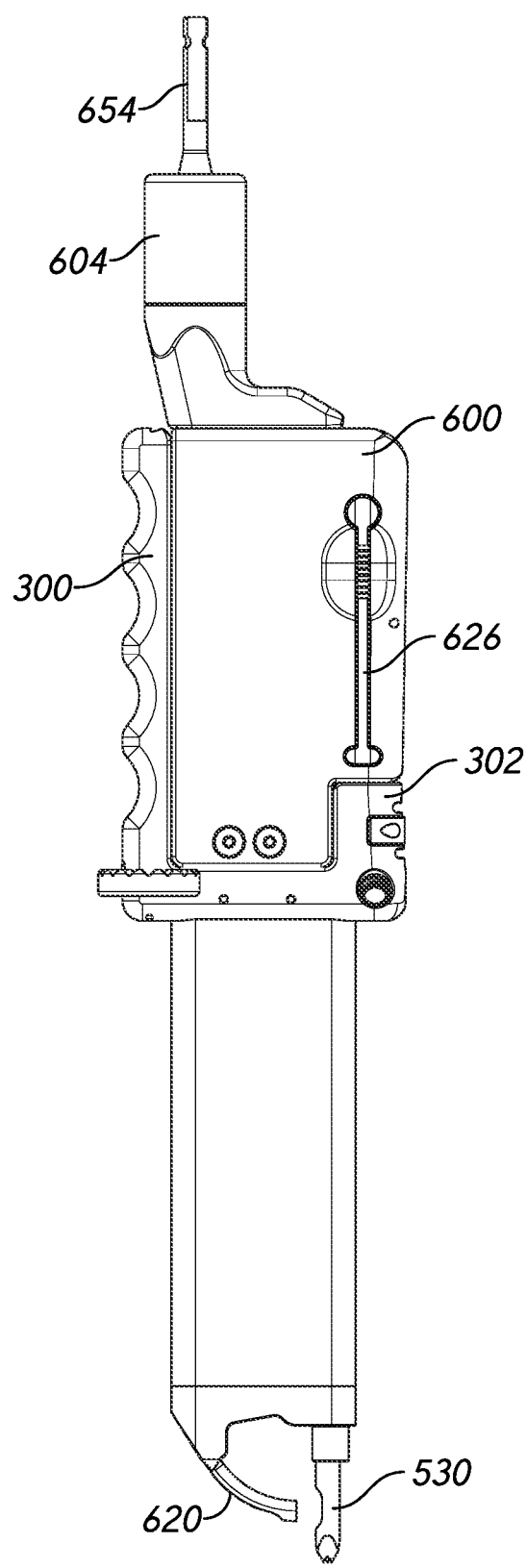

The method can include drilling a curved hole. The drill 600 can be inserted into the portal 300 until it locks in place. The latch arms 626 of the drill 600 can engage the portal handle 302. The method can include attaching a power drill to the drill coupler 654. The drill 600 can include the drill bit 670. The drill bit 670 can be guided by the swing arm 620. The advancer body 604 can be moved proximally and distally to advance and retract the swing arm 620. The swing arm 620 and the drill bit 670 can form a curved lumen. The drill 600 can drill a curved hole from the lamina to the pedicle. The drill 600 can be removed. The awl 530 can be left in place. The portal 300 can be left in place. The drill 600 can be coupled to the portal 300 is shown in FIG. 74. The drill bit tip 672 extends toward the awl 530.

Figure 77:
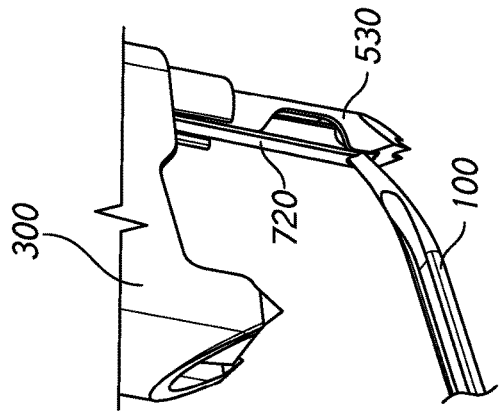
Figure 76:
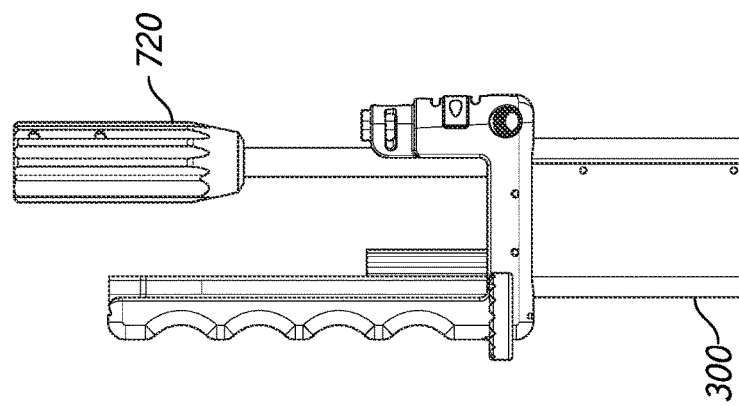
Figure 75:
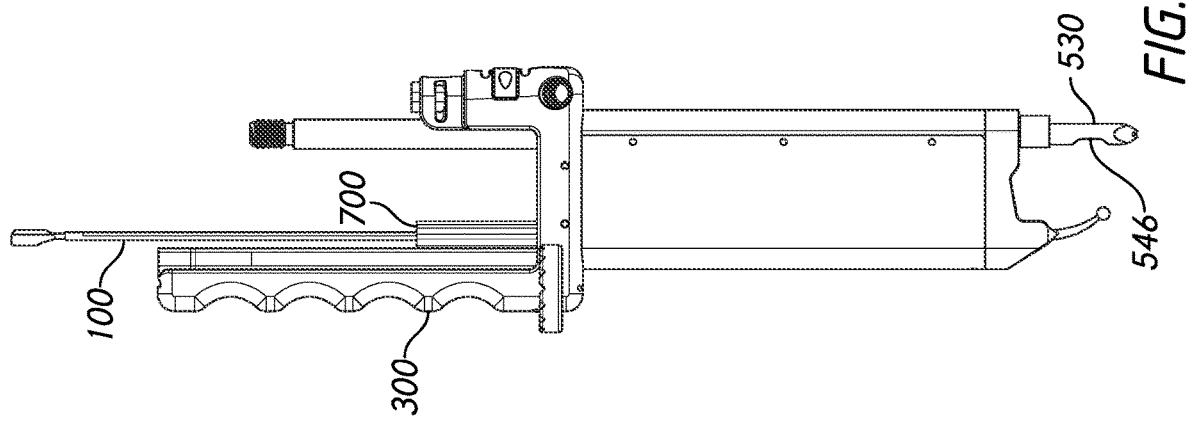

The method can include passing the bone tie 100. The implant shuttle 700 can be inserted into the portal 300. The bone tie 100 can be fed down the implant shuttle 700. The implant shuttle 700 is shown in FIG. 75. The bone tie 100 can be fed through the curved bone lumen. The bone tie 100 can be advanced to the awl 530. The marker 144 can facilitate visualization of the bone tie 100. The head 136 can include the marker 144. The position of the head 136 can be confirmed under fluoroscopy that the marker 144 in the ball 136 is inside the retriever portion 546 of the awl 530. The implant catcher 720 can engage the awl 530. The implant catcher shaft 734 can slide relative to the awl 530. The implant catcher handle 722 can be rotated to engage the threaded portion 536 of the awl with the distal threaded bore 730 of the implant catcher 720. The implant catcher 720, the portal 300, and the awl 530 are shown in FIG. 76. The implant catcher 720, the bone tie 100, and the awl 530 are shown in FIG. 77. The bone tie 100 can be advanced until the head 136 is positioned within the awl 530. The implant catcher 720 can be lowered relative to the awl 530 to capture the head 136 of the bone tie 100. The bone tie 100 can extend through the lumen formed by the drill 600. The portal 300 can be left in place. The awl 530 and the implant catcher 720 can be left in place.

The method can include removing the awl 530 and the implant catcher 720. The awl jack 750 can be positioned around the shaft of the awl 530. The awl jack 750 can be above the portal handle 302. The awl jack 750 can be below the implant catcher handle 722. The handles 752, 754 can be squeezed together to lift the awl 530 and the implant catcher 720 out of the pedicle. The motion of the handles 752, 754 is shown in FIGS. 78 and 79. Once the awl 530 has been released from the pedicle, the awl 530 can be pulled from the portal 300. The implant catcher 720 can be unthreaded from the awl 530. The ball 136 can be released from the retriever portion 546 of the awl 530. The bone tie 100 can remain through the lumen. The bone tie 100 can form an arc through the bone lumen. The implant shuttle 700 can be removed. The bone tie 700 can slide through the passageway 708. The passageway 708 can be open along the length to allow disengagement of the bone tie 100 from the implant shuttle 700.

Figure 80:
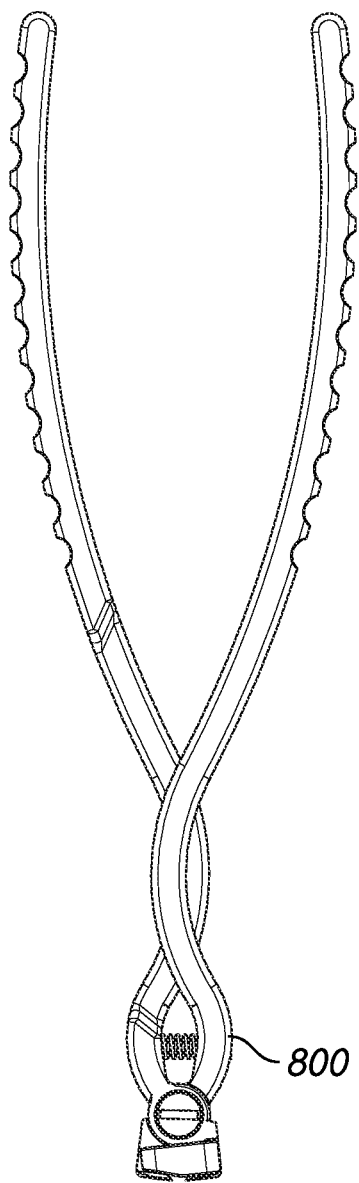
Figure 81:
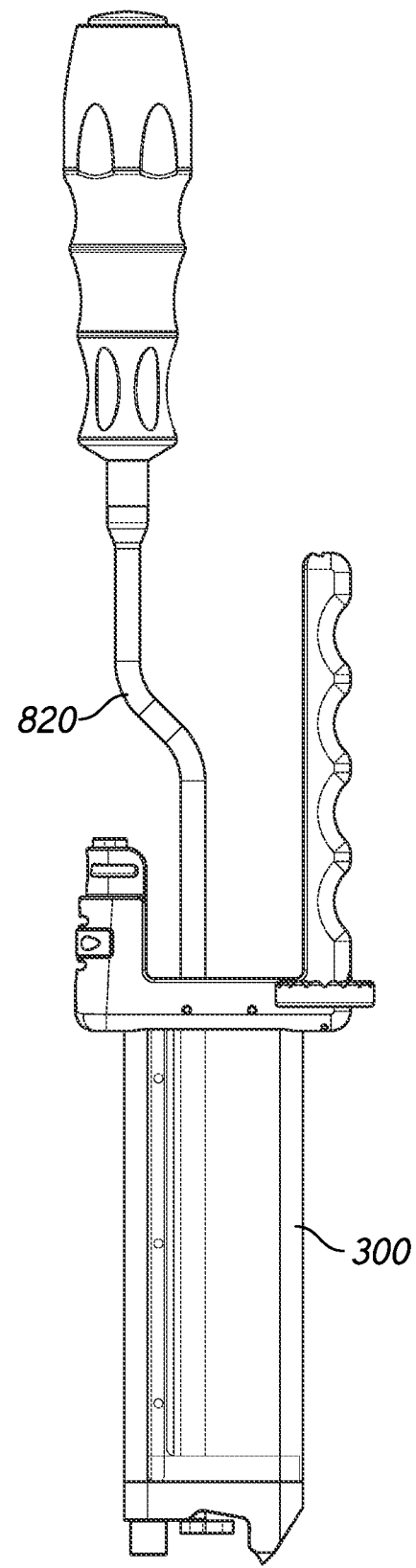

The method can include trimming the bone tie 100. The guarded flush cutter 800 can remove the ball 136 from the bone tie 100. The guarded flush cutter 800 is shown in FIG. 80. The cut end of the bone tie 100 can be fed through the lumen 118 of the fastener section 106. The bone tie 100 can form a loop through the bone lumen. The cut end can pass through the head pusher 820. The head pusher 820 can provisionally tension the bone tie 100 through the portal 300. The head pusher 820 is shown in FIG. 81. The portal 300 can be removed. The bone tie 100 can be left in place. In some embodiments, the portal 300 and the bone tie 100 can be left in place and tensioning and cutting of the bone tie 100 can be performed through the portal 300.

Figure 82:
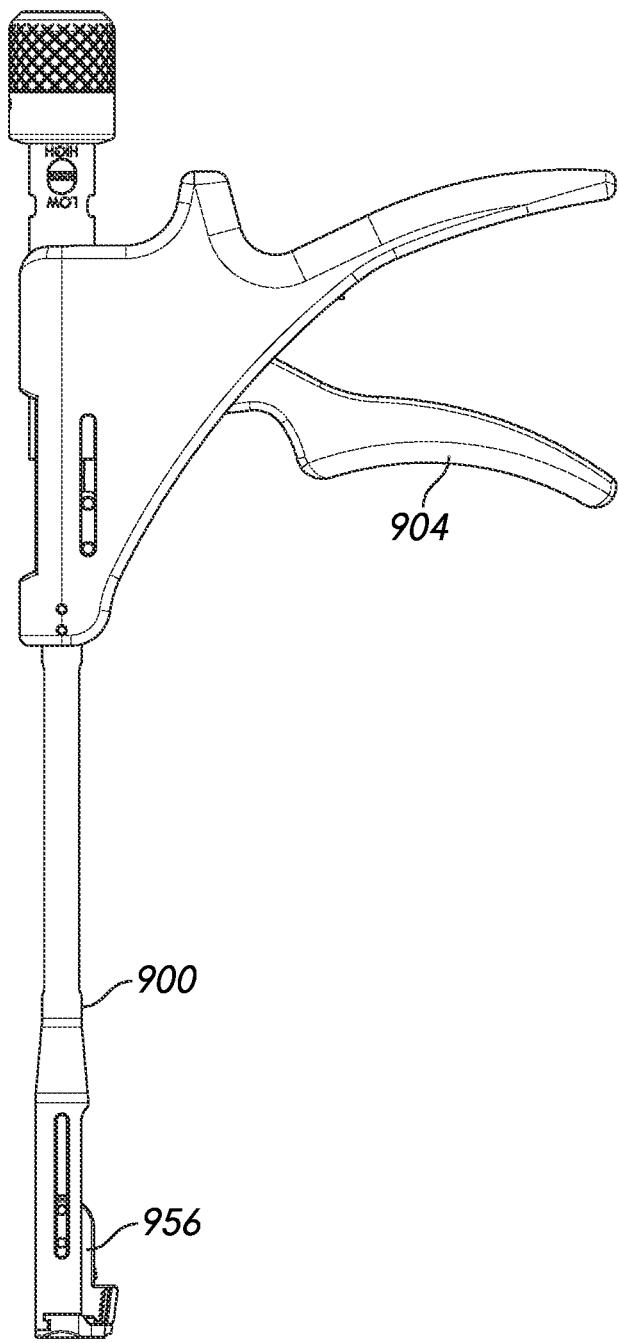
Figure 83:
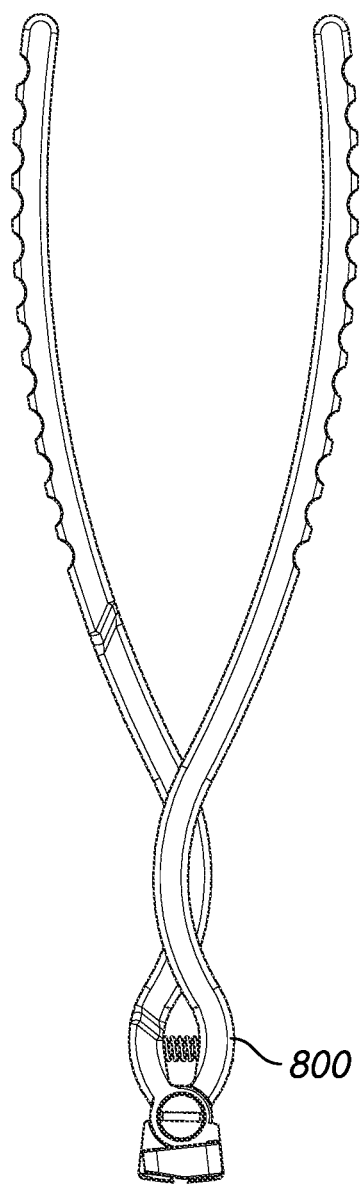
Figure 84:
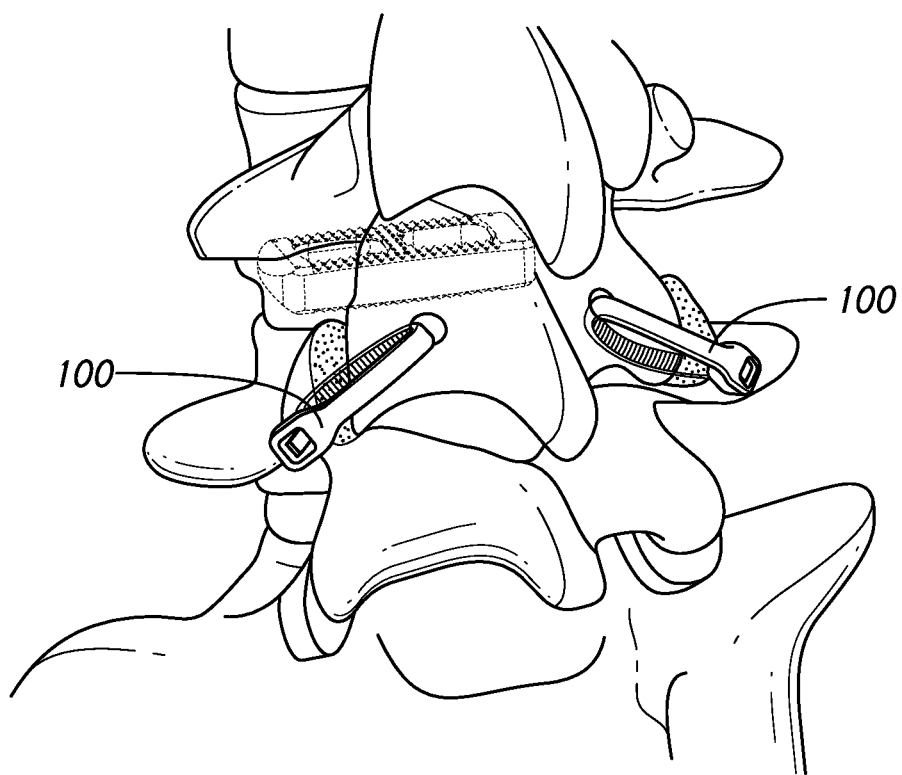

The method can include tensioning the bone tie 100. The method can include using the tensioner 900 to fully tension the bone tie 100. The tensioner 900 is shown in FIG. 82. The tensioner 900 can pull the free end of the bone tie 100 through the lumen 118 of the fastener section 106. The puller 956 can slide proximally to pull the bone tie 100 proximally upon actuation of the pivoting handle 904. The tensioner 900 can adjust the level of tension applied. The tensioner 900 can be actuated until the desired level of tension is applied. The tensioner 900 can include one or more visual cues to indicate that the desired level of tension has been applied. The guarded flush cutter 800 can be used to trip the excess free end of the bone tie 100. The guarded flush cutter 800 is shown in FIG. 83. The placement of the bone tie 100 can be confirmed under fluoroscopy. The incision can be closed. The placement of the bone tie 100 is shown in FIG. 84. One or more bone ties can be placed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A method for treating the spine comprising:
   positioning a k-wire into cannulation of a cannulated needle;
   positioning a portal, wherein the portal comprises a portal body comprising a lumen extending through the portal body from a proximal end of the portal body to a distal end of the portal body, wherein the distal end of the portal body engages the anatomy of a patient;
   inserting a drill into the lumen of the portal body from the proximal end of the portal body toward the distal end of the portal body;
   forming a curved lumen with the drill inserted into the lumen of the portal body, wherein the drill comprises a drill body and a swing arm, wherein the swing arm advances in an arc relative to the drill body;
   removing the drill from the portal while the portal remains engaged with the anatomy of the patient; and
   passing a bone tie through the curved lumen.

2. The method of claim 1, further comprising positioning the cannulated needle into a pedicle.

3. The method of claim 1, further comprising preparing hypertrophic facets.

4. The method of claim 1, further comprising positioning a trephine relative to a k-wire.

5. The method of claim 1, further comprising rotating a trephine to seat a trephine blade on a facet joint.

6. The method of claim 1, further comprising coupling the portal and a tissue splitter.

7. The method of claim 1, further comprising inserting a tissue splitter and the portal until the tissue splitter and the portal bottom out on a pedicle.

8. The method of claim 1, further comprising confirming the position of the portal.

9. A method for treating the spine comprising:
   positioning a portal, wherein the portal comprises a portal body comprising a lumen extending through the portal body from a proximal end of the portal body to a distal end of the portal body, wherein the distal end of the portal body engages the anatomy of a patient;
   sliding an awl through the portal;
   inserting a drill into the lumen of the portal while the awl remains through the portal;

forming a curved lumen with the drill inserted into the lumen of the portal body, wherein the drill comprises a drill body and a swing arm, wherein the swing arm advances in an arc relative to the drill body; and passing a bone tie through the curved lumen while the awl remains through the portal.

10. The method of claim 9, further comprising advancing the awl into a pedicle.

11. The method of claim 9, wherein inserting the drill into the lumen of the portal body further comprises locking the drill relative to the portal.

12. The method of claim 9, wherein forming the curved lumen further comprises forming the curved lumen from a lamina to a pedicle.

13. A method for treating the spine comprising:
positioning a portal, wherein the portal comprises a portal body comprising a lumen extending through the portal body from a proximal end of the portal body to a distal end of the portal body, wherein the distal end of the portal body engages the anatomy of a patient;
inserting a drill into the lumen of the portal body;
forming a curved lumen with the drill inserted into the lumen of the portal body, wherein the drill comprises a drill body and a swing arm, wherein the swing arm advances in an arc relative to the drill body;
removing the drill from the portal and inserting an implant shuttle into the lumen of the portal; and
passing a bone tie through the implant shuttle.

14. The method of claim 13, further comprising feeding the bone tie through the curved lumen.

15. The method of claim 13, further comprising sliding an implant catcher relative to an awl.

16. The method of claim 13, further comprising advancing the bone tie until a head of the bone tie is positioned within an awl.

17. The method of claim 13, further comprising tensioning the bone tie.

18. The method of claim 13, further comprising engaging one or more gears of the bone tie with a ratchet of the bone tie to form a loop.

19. The method of claim 13, further comprising applying tension to a free end of the bone tie after the bone tie forms a loop.

* * * * *

UNITED STATES PATENT AND TRADEMARK OFFICE
CERTIFICATE OF CORRECTION

| | | |
|---|---|---|
| PATENT NO. | : 12,369,952 B2 | Page 1 of 1 |
| APPLICATION NO. | : 18/062979 | |
| DATED | : July 29, 2025 | |
| INVENTOR(S) | : Taylor Semingson | |

It is certified that error appears in the above-identified patent and that said Letters Patent is hereby corrected as shown below:

On the Title Page

Page 6, Column 2 (Item (56) Other Publications), Line 22, delete "Appl. No. 60/749,000; U.S." and insert -- Appl. No. 60/721,909; U.S. --.

Page 6, Column 2 (Item (56) Other Publications), Line 23, delete "No. 60/749,000 and" and insert -- No. 60/750,005 and --.

In the Specification

Column 3, Line 53, delete "splitter of Figure" and insert -- splitter of Figure 20. --.

Column 4, Line 13, delete "bit of Figure" and insert -- bit of Figure 40. --.

In the Claims

Column 52, Claim 4, Line 49, delete "to a k-wire." and insert -- to the k-wire. --.

Signed and Sealed this
Thirtieth Day of September, 2025

John A. Squires
*Director of the United States Patent and Trademark Office*